US012558379B2

(12) United States Patent
Tseng et al.

(10) Patent No.: US 12,558,379 B2
(45) Date of Patent: Feb. 24, 2026

(54) COMPOSITIONS AND METHODS RELATING TO POOLED FETAL SUPPORT TISSUE

(71) Applicant: BIOTISSUE HOLDINGS INC., Miami, FL (US)

(72) Inventors: Scheffer Tseng, Pinecrest, FL (US); Ek Kia Tan, Pinecrest, FL (US); Lorraine Chua, Pinecrest, FL (US)

(73) Assignee: BIOTISSUE HOLDINGS INC., Miami, FL (US)

( * ) Notice: Subject to any disclaimer, the term of this patent is extended or adjusted under 35 U.S.C. 154(b) by 0 days.

(21) Appl. No.: 18/642,534

(22) Filed: Apr. 22, 2024

(65) Prior Publication Data

US 2024/0269195 A1    Aug. 15, 2024

Related U.S. Application Data

(63) Continuation of application No. PCT/US2023/019602, filed on Apr. 24, 2023.

(60) Provisional application No. 63/334,283, filed on Apr. 25, 2022.

(51) Int. Cl.
*A61K 35/50* (2015.01)
*A61K 35/51* (2015.01)
*G01N 33/50* (2006.01)

(52) U.S. Cl.
CPC .............. *A61K 35/50* (2013.01); *A61K 35/51* (2013.01); *G01N 33/5082* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,033,252 A | 7/1991 | Carter | |
| 5,052,558 A | 10/1991 | Carter | |
| 5,323,907 A | 6/1994 | Kalvelage | |
| 6,152,142 A | 11/2000 | Tseng | |
| 6,326,019 B1 | 12/2001 | Tseng | |
| 7,494,802 B2 | 2/2009 | Tseng et al. | |
| 8,128,968 B2 | 3/2012 | Gao et al. | |
| 8,153,162 B2 | 4/2012 | Tseng et al. | |
| 8,182,840 B2 | 5/2012 | Tseng et al. | |
| 8,182,841 B2 | 5/2012 | Tseng et al. | |
| 8,187,639 B2 | 5/2012 | Tseng et al. | |
| 8,420,126 B2 | 4/2013 | Tseng et al. | |
| 8,440,235 B2 | 5/2013 | Tseng et al. | |
| 8,440,240 B2 | 5/2013 | Gao et al. | |
| 8,455,009 B2 | 6/2013 | Tseng et al. | |
| 8,455,015 B2 | 6/2013 | Gao et al. | |
| 8,460,714 B2 | 6/2013 | Tseng et al. | |
| 8,865,232 B2 | 10/2014 | Gao et al. | |
| 8,865,233 B2 | 10/2014 | Gao et al. | |
| 8,940,294 B2 | 1/2015 | Tseng et al. | |
| 9,006,192 B2 | 4/2015 | Tseng et al. | |
| 9,161,954 B2 | 10/2015 | Tseng et al. | |
| 9,161,955 B2 | 10/2015 | Tseng et al. | |
| 9,161,956 B2 | 10/2015 | Tseng et al. | |
| 9,175,066 B2 | 11/2015 | Tseng et al. | |
| 9,198,939 B2 | 12/2015 | Tseng et al. | |
| 9,526,770 B2 | 12/2016 | Tseng et al. | |
| 9,675,733 B2 | 6/2017 | Tseng et al. | |
| 9,682,044 B2 | 6/2017 | Tseng et al. | |
| 9,682,160 B2 | 6/2017 | Tseng et al. | |
| 9,724,370 B2 | 8/2017 | Tseng et al. | |
| 9,750,771 B2 | 9/2017 | Tseng et al. | |
| 9,750,772 B2 | 9/2017 | Tseng et al. | |
| 9,808,491 B2 | 11/2017 | Tseng et al. | |
| 9,931,423 B2 | 4/2018 | Tseng et al. | |
| 9,956,252 B2 | 5/2018 | Tseng et al. | |
| 10,040,821 B2 | 8/2018 | Tseng et al. | |
| 10,253,065 B2 | 4/2019 | Tseng et al. | |
| 10,272,119 B2 | 4/2019 | Tseng et al. | |
| 10,342,831 B2 | 7/2019 | Tseng et al. | |
| 10,426,731 B2 | 10/2019 | Tseng et al. | |
| 10,588,924 B1 * | 3/2020 | Wootten ................ | A61K 47/12 |
| 10,632,155 B2 | 4/2020 | Tseng et al. | |
| 10,717,763 B2 | 7/2020 | Tseng et al. | |
| 11,116,800 B2 | 9/2021 | Tseng et al. | |
| 11,318,169 B2 | 5/2022 | Tseng et al. | |
| 11,518,782 B2 | 12/2022 | Tseng et al. | |
| 11,590,265 B2 | 2/2023 | Tseng et al. | |
| 11,707,492 B2 | 7/2023 | Tseng | |
| 2005/0026279 A1 | 2/2005 | Tseng et al. | |
| 2007/0010008 A1 | 1/2007 | Tseng et al. | |

(Continued)

FOREIGN PATENT DOCUMENTS

| WO | WO-9837903 A1 | 9/1998 |
|---|---|---|
| WO | WO-03077794 A2 | 9/2003 |

(Continued)

OTHER PUBLICATIONS

He et al, Scientific Reports, 2017, 7:43736, 15 pages. (Year: 2017).*
"Tissue." Merriam-Webster.com Dictionary, Merriam-Webster, https://www.merriam-webster.com/dictionary/tissue. Accessed May 2, 2025. (Year: 2025).*
"Cryopreservation." Merriam-Webster.com Dictionary, Merriam-Webster, https://www.merriam-webster.com/dictionary/cryopreservation. Accessed May 2, 2025. (Year: 2025).*
Cooke et al. Comparison of cryopreserved amniotic membrane and umbilical cord tissue with dehydrated amniotic membrane/chorion tissue. J Wound Care 23(10):465-474 (2014).
FDA Guidance: Potency Tests for Cellular and Gene Therapy Products, Jan. 2011.
Lei, Jennifer., et al., Dehydrated Human Amnion/Chorion Membrane (dHACM) Allografts as a Therapy for Orthopedic Tissue Repair. Techniques in Orthopaedics 32(3): 149-157 (2017).
PCT/US2023/019602 International Search Report and Written Opinion dated Jun. 28, 2023.

*Primary Examiner* — Allison M Fox

(74) *Attorney, Agent, or Firm* — WILSON SONSINI GOODRICH & ROSATI

(57) ABSTRACT

Described herein is a composition, methods comprising, pooled fetal support tissue, wherein the pooled fetal support tissue comprises a therapeutically effective amount of native HC-HA/PTX3 complex.

26 Claims, 15 Drawing Sheets

(56)            References Cited

U.S. PATENT DOCUMENTS

| | | |
|---|---|---|
| 2007/0082017 A1 | 4/2007 | Tseng et al. |
| 2007/0128719 A1 | 6/2007 | Tseng et al. |
| 2007/0231297 A1* | 10/2007 | Smith .................... A61K 35/50 |
| | | 424/85.1 |
| 2009/0214676 A1 | 8/2009 | Gao et al. |
| 2012/0141595 A1 | 6/2012 | Tseng et al. |
| 2013/0156863 A1 | 6/2013 | Tseng et al. |
| 2013/0344163 A1 | 12/2013 | Tseng et al. |
| 2014/0106448 A1 | 4/2014 | Chen et al. |
| 2014/0112998 A1* | 4/2014 | Tseng .................... A61K 33/06 |
| | | 424/583 |
| 2015/0203814 A1 | 7/2015 | Tseng et al. |
| 2016/0008295 A1 | 1/2016 | Tseng et al. |
| 2016/0095931 A1 | 4/2016 | Tseng et al. |
| 2016/0106785 A1 | 4/2016 | Tseng et al. |
| 2016/0120912 A1 | 5/2016 | Tseng |
| 2016/0184368 A1 | 6/2016 | Tseng et al. |
| 2016/0243288 A1 | 8/2016 | Tseng et al. |
| 2016/0303171 A1 | 10/2016 | Tseng et al. |
| 2016/0324902 A1 | 11/2016 | Tseng et al. |
| 2016/0339061 A1* | 11/2016 | Tseng .................... A61K 35/51 |
| 2017/0239389 A1 | 8/2017 | Tseng et al. |
| 2018/0008649 A1 | 1/2018 | Aberman et al. |
| 2019/0343890 A1 | 11/2019 | Tseng et al. |
| 2021/0290690 A1 | 9/2021 | Tseng et al. |
| 2021/0386791 A1 | 12/2021 | Tseng et al. |
| 2022/0175849 A1 | 6/2022 | Tseng et al. |
| 2023/0083005 A1 | 3/2023 | Tseng et al. |
| 2023/0172994 A1 | 6/2023 | Tseng et al. |
| 2023/0279048 A1 | 9/2023 | Tseng et al. |
| 2023/0285640 A1 | 9/2023 | Tseng et al. |
| 2023/0310512 A1 | 10/2023 | Tseng et al. |
| 2023/0364155 A1 | 11/2023 | Tseng |
| 2023/0398260 A1 | 12/2023 | Tseng et al. |
| 2024/0000704 A1 | 1/2024 | Tseng et al. |

FOREIGN PATENT DOCUMENTS

| | | |
|---|---|---|
| WO | WO-2004033635 A2 | 4/2004 |
| WO | WO-2005067892 A1 | 7/2005 |
| WO | WO-2006094247 A2 | 9/2006 |
| WO | WO-2007002900 A1 | 1/2007 |
| WO | WO-2007038686 A2 | 4/2007 |
| WO | WO-2008002329 A2 | 1/2008 |
| WO | WO-2008103191 A1 | 8/2008 |
| WO | WO-2009032773 A2 | 3/2009 |
| WO | WO-2010124296 A2 | 10/2010 |
| WO | WO-2011031489 A2 | 3/2011 |
| WO | WO-2012003377 A2 | 1/2012 |
| WO | WO-2012170905 A1 | 12/2012 |
| WO | WO-2013032938 A1 | 3/2013 |
| WO | WO-2014011813 A1 | 1/2014 |
| WO | WO-2015187812 A1 | 12/2015 |
| WO | WO-2016010984 A2 | 1/2016 |
| WO | WO-2016073667 A1 | 5/2016 |
| WO | WO-2016187555 A1 | 11/2016 |
| WO | WO-2017132503 A1 | 8/2017 |
| WO | WO-2020097251 A1 | 5/2020 |
| WO | WO-2020257626 A1 | 12/2020 |
| WO | WO-2021091502 A1 | 5/2021 |
| WO | WO-2021101802 A2 | 5/2021 |
| WO | WO-2021163419 A1 | 8/2021 |
| WO | WO-2021203045 A1 | 10/2021 |
| WO | WO-2022093725 A1 | 5/2022 |
| WO | WO-2023211823 A1 | 11/2023 |

* cited by examiner

**(STEP 2)
DRUG SUBSTANCE**

**(STEP 3)
DRUG PRODUCT**

HC1

SD-1: single donor-1;  SD-2: single donor-2; SD-3:single donor-3; SD-4: single donor-4

PTX3

SD-1: single donor-1;  SD-2: single donor-2; SD-3:single donor-3; SD-4: single donor-4

SD-1: single donor-1;  SD-2: single donor-2; SD-3:single donor-3; SD-4: single donor-4
P1-P3: pooled donor sample 1, 2 or 3

COMPOSITIONS AND METHODS RELATING TO POOLED FETAL SUPPORT TISSUE

CROSS REFERENCE

This application is a continuation of International Application No. PCT/US2023/019602, filed Apr. 24, 2023, which claims the benefit of U.S. Application No. 63/334,283 filed Apr. 25, 2022, all of which are hereby incorporated by reference in their entireties.

BRIEF SUMMARY

Provided herein are compositions and methods relating to pooled fetal support tissue. Because fetal support tissue has shown tremendous potential against numerous clinical indications, there is significant interest in the development of fetal support tissue products. However, the clinical and commercial potential of fetal support tissue products relies on the effective processing of the tissue products as well as uniformity and potency of the end products. Preservation of bioactive components is critical when processing fetal support tissue. For instance, differences in processing methods can alter the structure and biochemical composition of the fetal support tissue and can impair the activity of critical signaling molecules vital for the intended therapeutic activities. Disclosed herein are compositions and methods for the isolation, processing, and generation of fetal support tissue products and/or formulations that preserve the potency and stability of tissue bioactive factors.

In general, conventional protocols do not utilize pooling of cellular, tissues or biological products from more than one human donor because of the risks of communicable diseases and the difficulty of establishing manufacturing and processing/production facilities that meet regulatory standards. The present disclosure advantageously describes pooling of donor fetal support tissues. First, the practice of pooling biological products from multiple donors mitigates variability that is inherently prevalent among different donors. Pooling of donor tissue controls for potency for each individual donor, increases consistency and facilitates the proficiency of further qualification, sampling, and clinical testing. Additionally, pooling of donor samples enriches fetal support tissue components. Disclosed herewith, are methods of generating pooled fetal support tissues from multiple donors. In some embodiments, lyophilization of fetal support tissue significantly reduces degradation of the tissue bioactive components in the fetal support tissue and concentrates bioactive tissue components such as for example, increased stability and concentration of bioactive components contained in fetal support tissue material including HA complex (HC-HA/PTX3), cytokines, growth factor, and any other bioactive factors found in fetal support tissues.

SUMMARY

Described herein in one aspect is a composition comprising, pooled fetal support tissue, wherein the pooled fetal support tissue comprises a therapeutically effective amount of native HC-HA/PTX3 complex. In some embodiments, the composition comprises pooled fetal support tissue, wherein the fetal support tissue comprises a therapeutically effective amount of native HC-HA/PTX3 complex. In some embodiments, wherein the pooled fetal support tissue increases uniformity of the native HC-HA/PTX3 complex in the composition. In some embodiments, the pooled fetal support tissue comprises fetal support tissue from a plurality of donors. In some embodiments, disclosed herein is a composition, wherein the pooled fetal support tissue comprises fetal support tissue from at least three donors. In some embodiments, the pooled fetal support tissue comprises fetal support tissue from at least five donors. In some embodiments, the pooled fetal support tissue comprises fetal support tissue from at least ten donors. In some embodiments, the composition exhibits a therapeutic potency as determined by an assay comprising one or more of an HA content assay, BCA total protein assay, a PTX3 content assay, an ODI-TRAP assay, an M2 polarization assay, or a WST-1 assay.

In some embodiments, the therapeutic potency is determined by the ODI-TRAP assay. In some embodiments, the composition exhibits a statistically significant inhibition of TRAP activity compared to a positive control in the ODI-TRAP assay when an HA content of the composition is at least 200 μg/ml, 250 μg/ml, 300 μg/ml, 400 μg/ml, 500 μg/ml, 600 μg/ml, 700 μg/ml, 800 μg/ml, 900 μg/ml, 1,000 μg/ml.

In some embodiments, the positive control is for the ODI-TRAP is RANKL treatment. In some embodiments, the therapeutic potency is determined by the M2 assay. In some embodiments, the therapeutic potency is determined by the NO assay.

In some embodiments, the therapeutic potency can be determined by various assay, for example and without limitation, by the WST-1 assay.

In some embodiments, the therapeutic potency is determined by the BCA protein assay. In some embodiments, the therapeutic potency is determined by the HA content assay. In some embodiments, an HA content of the composition is at least 75 μg/ml. In some embodiments, an HA content of the composition is at least 90 μg/ml. In some embodiments, a total protein content of the composition is at least 250 μg/ml. In some embodiments, the pooled fetal support tissue is lyophilized. In some embodiments, the pooled fetal support tissue is lyophilized prior to pooling the fetal support tissue. In some embodiments, the pooled fetal support tissue is lyophilized after pooling the fetal support tissue. In some embodiments, the pooled fetal support tissue composition is previously frozen or cryopreserved. In some embodiments, the pooled fetal support tissue comprises a particle size of about 0.01 micrometer (μm) to about 240 μm in diameter. In some embodiments, the pooled fetal support tissue comprises an average particle size of about 0.5 μm. In some embodiments, the pooled fetal support tissue comprises placenta, umbilical cord, placental amniotic membrane umbilical cord amniotic membrane, Wharton's jelly, chorion, or amnion-chorion, or any combination thereof. In some embodiments, the pooled fetal support tissue comprises placental amniotic membrane, umbilical cord, or both. In some embodiments, the pooled fetal support tissue is pulverized before pooling. In some embodiments, the pooled fetal support tissue is pulverized after pooling. In some embodiments, the pooled fetal support tissue is morselized. In some embodiments, the pooled composition is filtered or ultra-filtered. In some embodiments, the pooled fetal support tissue is decellularized. In some embodiments, the pooled fetal support tissue is devitalized. In some embodiments, the pooled fetal support tissue is a gel extract. In some embodiments, the pooled fetal support tissue is powdered. In some embodiments, the pooled fetal support tissue comprises 5% water by weight or more. In some embodiments, the pooled fetal support tissue comprises at most 15% water by weight. In some embodiments, the pooled fetal support tissue is obtained from a frozen or previously frozen fetal support tissue. In some embodiments, the pooled fetal support tissue is substantially free of a vein or artery. In some embodiments, substantially all cells of the pooled fetal support tissue are dead. In some embodiments, the pooled fetal support tissue is terminally sterilized, gamma irradiated, filtered, electron beam sterilized or a combination thereof. In some embodiments, the composition is provided as a pharmaceutical composition and further comprises a pharmaceutically acceptable excipient. In some embodiments, the pharmaceutically acceptable excipient is normal saline.

The current application further discloses a method of treating a degenerative disease in an individual comprising administering the pooled fetal support tissue described herein to the individual.

Described herein is a method of treating inflammation in an individual comprising administering the pooled fetal support tissue described herein to the individual. In yet another aspect, disclosed herein, is a method of promoting wound healing in an individual comprising administering the pooled fetal support tissue described herein to the individual.

Also, disclosed herein in another aspect, is a method of treating osteoarthritis in an individual using a composition comprising, pooled fetal support tissue, the method comprising administering the pooled fetal support tissue to the individual. In some embodiments, disclosed herein, the osteoarthritis may be of the knee. In some embodiments, the osteoarthritis may be a facet joint. In some embodiments, the osteoarthritis may be of an ankle. In some embodiments, the osteoarthritis may be of a hip. In some embodiments, the osteoarthritis may be of a shoulder. In some embodiments, the osteoarthritis may be of an elbow. In some embodiments, the osteoarthritis may be of a wrist. In some embodiments, the osteoarthritis may be of small joints of the hands. In some embodiments, the osteoarthritis may be of small joints of the feet. In some embodiments, the osteoarthritis may be of a cervical spine. In some embodiments, disclosed herein is a method of making composition of pooled fetal support tissue comprising obtaining fetal support tissue from a plurality of donors and pooling the fetal support tissue from the plurality of donors. In some embodiments, the fetal support tissue from the plurality of donors is lyophilized prior to the pooling. In some embodiments, the fetal support tissue from the plurality of donors is lyophilized after the pooling. In some embodiments, the method of making of the lyophilized composition further comprises processing the fetal support tissue from the plurality of donors by morselizing, pulverizing, micronizing, or a combination thereof. In some embodiments, the method further comprises, devitalizing the fetal support tissue from the plurality of donors. In some embodiments, the method further comprises decellularizing the fetal support tissue from the plurality of donors. In some embodiments, the fetal support tissue from the plurality of donors is not dehydrated. In some embodiments, the fetal support tissue from the plurality of donors is not dehydrated to comprise less than 20% water by weight. In some embodiments, the fetal support tissue from the plurality of donors is not dehydrated to comprise less than 15% water by weight.

Disclosed herein, in certain embodiments, is a method of validating a pooled fetal support tissue product the method comprising conducting a validation assay on the pooled fetal support tissue, wherein the validation assay determines an amount and/or therapeutic potency of native HC-HA/PTX3 complex. In some embodiments, the native HC-HA/PTX3 is therapeutically active. In some embodiments, the validation assay comprises one or more of an HA content assay, a PTX3 content assay, an ODI-TRAP assay, BCA protein assay, an M2 polarization assay, NO assay, or a WST-1 assay. In some embodiments, the validation assay comprises the ODI-TRAP assay. In some embodiments, the pooled fetal support tissue product exhibits a statistically significant inhibition of TRAP activity compared to a positive control in the ODI-TRAP assay when an HA content of the composition is at least 200 µg/ml, 250 µg/ml, 300 µg/ml, 400 µg/ml, 500 µg/ml, 600 µg/ml, 700 µg/ml, 800 µg/ml, 900 µg/ml, 1,000 µg/ml. In some embodiments, the positive control is RANKL treatment. In some embodiments, the therapeutic potency is determined by the M2 assay. In some embodiments, the therapeutic potency is determined by the NO assay. In some embodiments, the therapeutic potency is determined by the WST-1 assay. In some embodiments, the therapeutic potency is determined by the BCA protein assay. In some embodiments, the therapeutic potency is determined by the HA content assay. In some embodiments, the therapeutic potency is determined by the PTX3 content assay. In some embodiments, an HA content of the composition is at least 75 µg/ml. In some embodiments, an HA content of the composition is at least 90 µg/ml. In some embodiments, a total protein content of the composition is at least 250 µg/ml.

BRIEF DESCRIPTION OF THE FIGURES

FIG. 8A) and pentraxin (PTX3; FIG. 8B)

polymers/macromolecules that make up the heavy chain 1-hyaluronic acid/pentraxin (HC-HA/PTX3) complex.

Figure 9:
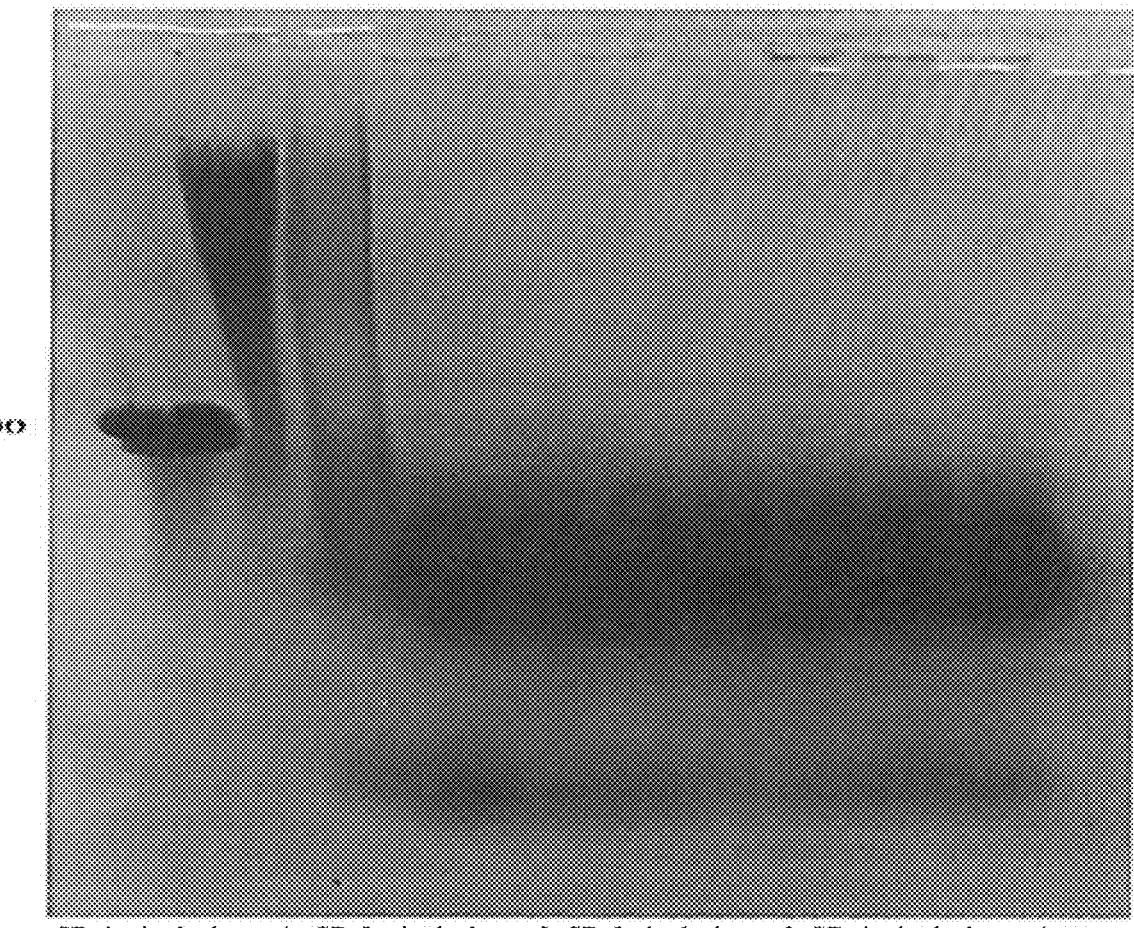

FIG. 9 shows an example of a qualitative analysis of HA evaluated to assess changes in molecular weight in samples from single donor lots (SD-1 to SD-4; non-pooled fetal support tissue in lanes 3-7) and pooled donor lots (P1-P3; pooled fetal support tissue (pFST) in lanes 8-10) agarose gel electrophoresis.

Figure 10A:
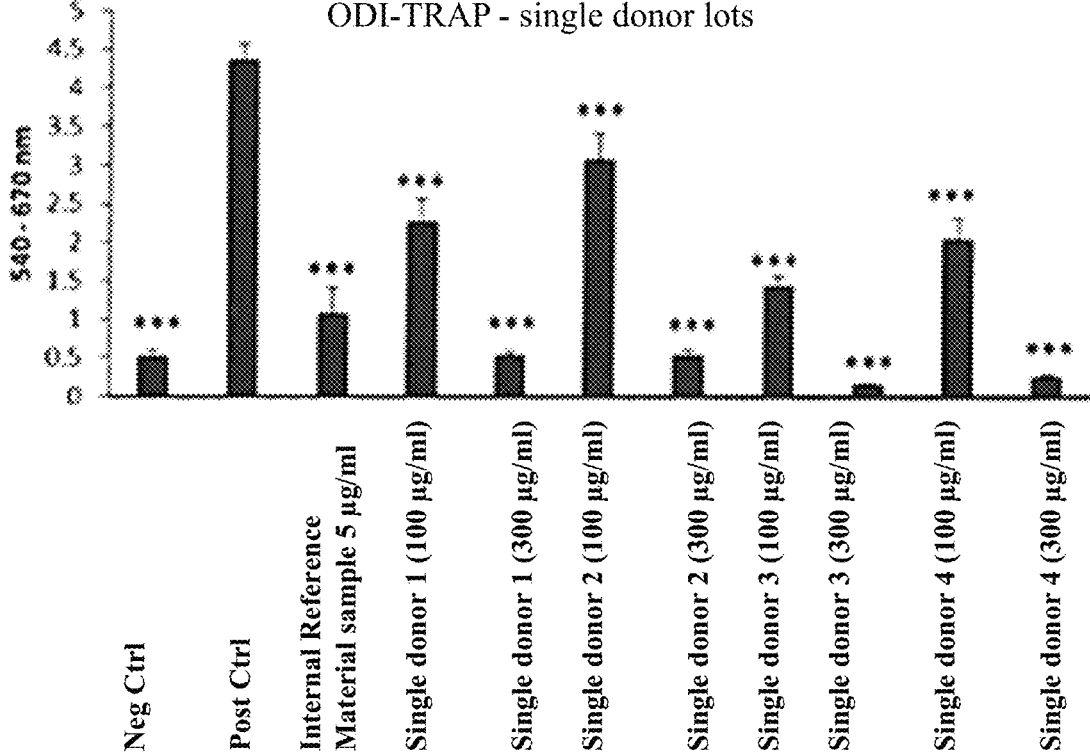
Figure 10B:
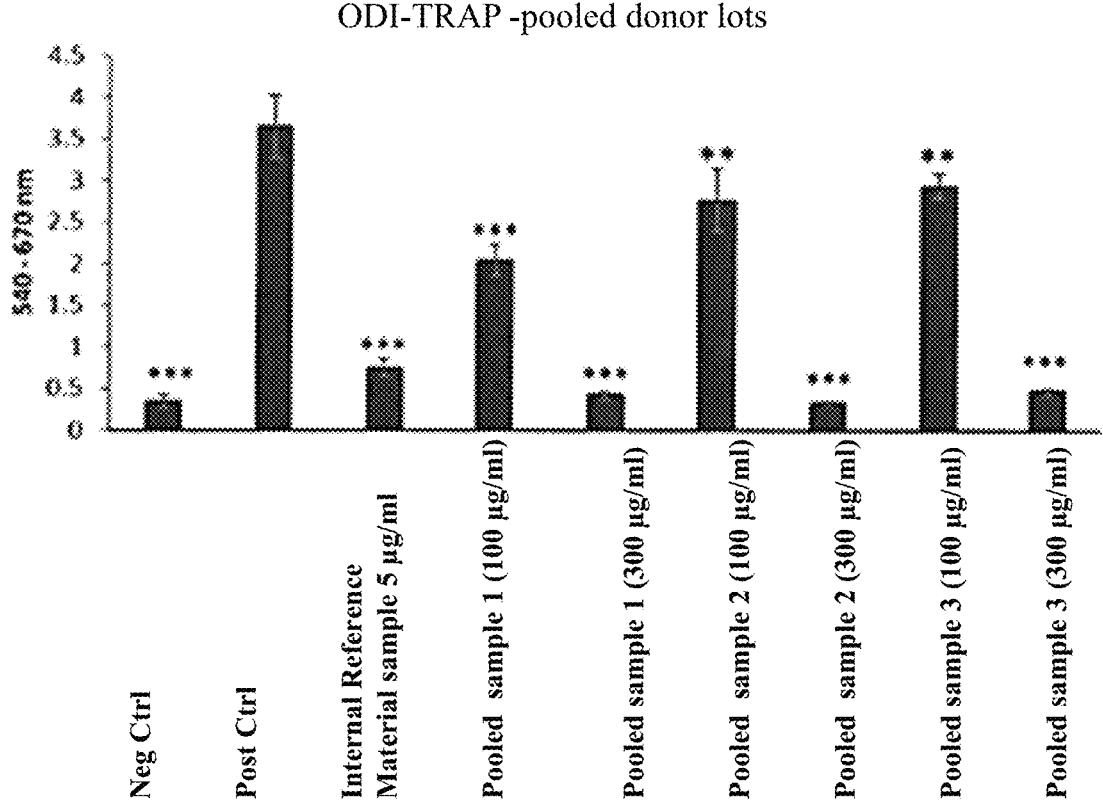

FIG. 10A-10B shows example of an ODI-TRAP quantitative assay conducted on samples from single/individual donor lots (FIG. 10A) and pooled donor lots (FIG. 10B).

Figure 11:
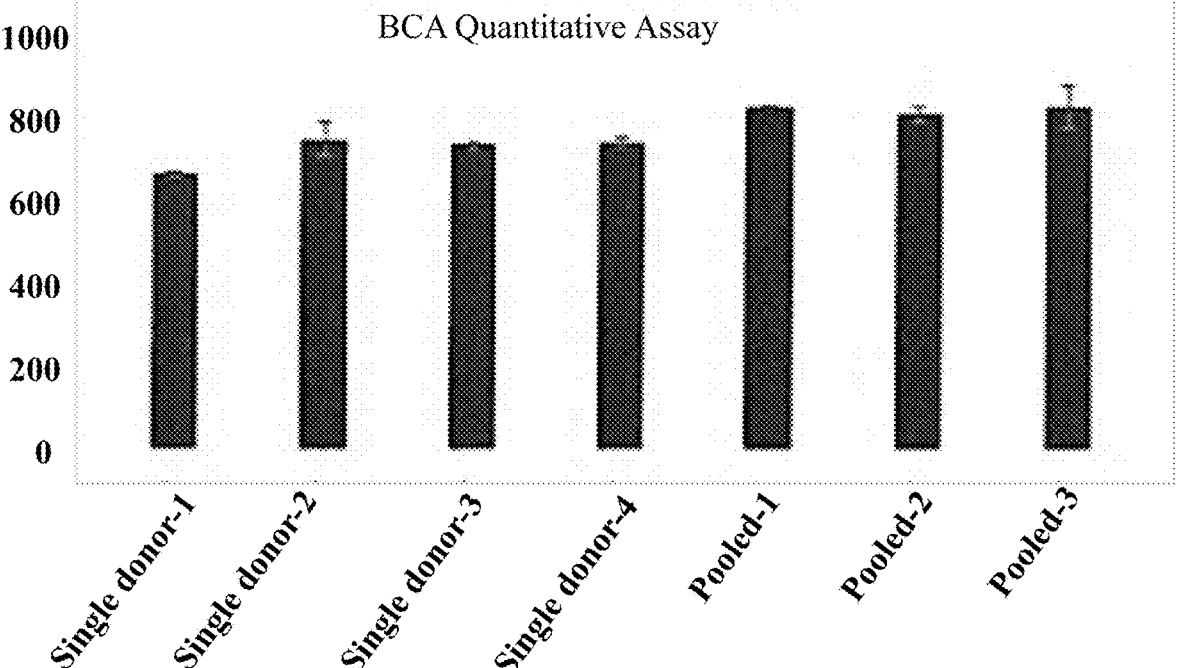

FIG. 11. Shows an example of a bicinchoninic acid (BCA) quantitative assay conducted on samples from single/individual donor lots and pooled donor lots.

DETAILED DESCRIPTION

Certain Definitions

Unless defined otherwise, all technical and scientific terms used herein have the same meaning as is commonly understood by one of skill in the art to which the claimed subject matter belongs.

As used herein, in some embodiments, ranges and amounts are expressed as "about" a particular value or range. About also includes the exact amount. Hence "about 5 µg" means "about 5 µg" and also "5 µg." Generally, the term "about" includes an amount that would be expected to be within experimental error.

As used herein, "fetal support tissue" means any isolated tissue derived from tissue used to support the development of a fetus. Examples of fetal support tissue include, but are not limited to, (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof. In some embodiments, the fetal support tissue is selected from the group consisting of placental amniotic membrane (PAM), umbilical cord amniotic membrane (UCAM), chorion, amnion-chorion, placenta, umbilical cord, and any combinations thereof. In some embodiments, the fetal support tissue comprises umbilical cord. Fetal support tissue includes any form of the fetal support tissue, including fresh, cryopreserved, terminally sterilized, micronized, lyophilized fetal support tissue or powders resulting from grinding fetal support tissue. In some embodiments, the fetal support tissue is ground, pulverized, morselized, a graft, a sheet, a powder, a gel, a homogenate, an extract, cryopulverized, decellularized, sieved, lyophilized, dehydrated or liquified, vaporized, micronized, or a terminally sterilized product.

Fetal support tissue including amniotic membrane and umbilical cord contain several innate biological factors useful for a number of purposes, including reducing inflammation and scarring to promote regenerative wound healing. Biological factors that may be found in fetal support tissue may contain components such as extracellular matrices, growth factors, and cytokines. Among extracellular matrices, hyaluronic acid (HA) and HA-containing complex, i.e., native HC-HA/PTX3 that is uniquely and abundantly present in amniotic membrane (AM) and umbilical cord (UC). The HC-HA/PTX3 complex—high molecular weight (HMW) hyaluronan (HA) covalently linked with heavy chain (HC) 1 from inter-α-trypsin inhibitor and further complexed with pentraxin3 (PTX3)—is one key active component of AM and UC that is responsible for the aforementioned effects to promote regenerative wound healing. Accordingly, production of a fetal support tissue product with a high yield of HC-HA/PTX3, HA, and other proteins of interest is needed. Production of a fetal support tissue product using a process that reduces or prevents the degradation of the HC-HA/PTX3 complex and other proteins of interest is also needed. Preventing degradation of HC-HA/PTX3, HA and other proteins of interest is important because the degradation of such proteins can render a fetal support tissue product unsuitable for use.

As used herein, "powder" means matter in the form of fine dry particles. In some embodiments, the particles are not uniform in size. In some embodiments, the particles are substantially uniform in size.

As used herein, "grinding" means any method of reducing fetal support tissue to small particle or a powder. The term grinding includes pulverizing, homogenizing, filing, milling, grating, pounding, and crushing.

As used herein, "placenta" refers to the organ that connects a developing fetus to the maternal uterine wall to allow nutrient uptake, waste elimination, and gas exchange via the maternal blood supply. The placenta is composed of three layers. The innermost placental layer surrounding the fetus is called amnion. The allantois is the middle layer of the placenta (derived from the embryonic hindgut); blood vessels originating from the umbilicus traverse this membrane. The outermost layer of the placenta, the chorion, comes into contact with the endometrium. The chorion and allantois fuse to form the chorioallantoic membrane.

As used herein, "chorion" refers to the membrane formed by extraembryonic mesoderm and the two layers of trophoblast. The chorion consists of two layers: an outer formed by the trophoblast, and an inner formed by the somatic mesoderm; the amnion is in contact with the latter. The trophoblast is made up of an internal layer of cubical or prismatic cells, the cytotrophoblast or layer of Langhans, and an external layer of richly nucleated protoplasm devoid of cell boundaries, the syncytiotrophoblast. The avascular amnion is adherent to the inner layer of the chorion.

As used herein, "amnion-chorion" refers to a product comprising amnion and chorion. In some embodiments, the amnion and the chorion are not separated (i.e., the amnion is naturally adherent to the inner layer of the chorion). In some embodiments, the amnion is initially separated from the chorion and later combined with the chorion during processing.

As used herein, "umbilical cord" refers to the organ that connects a developing fetus to the placenta. The umbilical cord is composed of Wharton's jelly, a gelatinous substance made largely from mucopolysaccharides. It contains one vein, which carries oxygenated, nutrient-rich blood to the fetus, and two arteries that carry deoxygenated, nutrient-depleted blood away.

As used herein, "placental amniotic membrane" (PAM) refers to amniotic membrane derived from the placenta. In some embodiments, the PAM is substantially isolated.

As used herein, "umbilical cord amniotic membrane" (UCAM) means amniotic membrane that has been extended to be a part of the umbilical cord. UCAM is a translucent membrane. The UCAM has multiple layers: an epithelial layer, a basement membrane; a compact layer; a fibroblast layer; and a spongy layer. It lacks blood vessels or a direct blood supply. In some embodiments, the UCAM comprises Wharton's Jelly. In some embodiments, the UCAM comprises blood vessels and/or arteries. In some embodiments, the UCAM comprises Wharton's Jelly and blood vessels and/or arteries.

As used herein, "human tissue" means any tissue derived from a human body. In some embodiments, the human tissue is a fetal support tissue selected from the group consisting of placental amniotic membrane, umbilical cord, umbilical cord amniotic membrane, chorion, amnion-chorion, placenta, or any combination thereof.

As used herein, "minimal manipulation" means (1) for structural tissue, processing that does not alter the original relevant characteristics of the tissue relating to the tissue's utility for reconstruction, repair, or replacement; and (2) for cells or nonstructural tissues, processing that does not alter the relevant biological characteristics of cells or tissues.

The term "fresh fetal support tissue" refers to fetal support tissue that is less than 72 hours following birth, and which is in substantially the same form as it was following birth. In some embodiments, the fresh fetal support tissue comprises fetal support tissue cells. In some embodiments, at least 50%, at least 60%, at least 70%, at least 80%, at least 90%, or at least 95% of the biological activity of the cell support tissue cells is maintained.

"Substantially isolated" or "isolated" when used in the context of a fetal support tissue means that the fetal support tissue is separated from most other non-fetal support tissue materials (e.g., other tissues, red blood cells, veins, arteries) derived from the original source organism.

As used herein, the phrase "wherein the biological and structural integrity of the isolated fetal support tissue is substantially preserved" means that when compared to the biological activity and structural integrity of fresh fetal support tissue, the biological activity and structural integrity of the isolated fetal support tissue has only decreased by about 5%, about 10%, about 15%, about 20%, about 25%, about 30%, about 35%, about 40%, about 50%, or about 60%.

As used herein, "processing" means any activity performed on a fetal support tissue or a preparation comprising native HC-HA/PTX3, other than recovery, donor screening, donor testing, storage, labeling, packaging, or distribution, such as testing for microorganisms, viruses, preparation, sterilization, steps to inactivate or remove adventitious agents, preservation for storage, and removal from storage. As used herein, "HC-HA/PTX3" denotes Heavy Chain 1-Hyaluronic Acid-Pentraxin 3; "-" denoting covalent linkage and "/" denoting non-covalent tight binding). HC-HA/PTX3 is found in fetal support and birth tissue, i.e., AM and UC.

As used herein, the terms "purified" and "isolated" mean a material (e.g., native HC-HA/PTX3 complex) substantially or essentially free from components that normally accompany it in its native state. In some embodiments, "purified" or "isolated" mean a material (e.g., native HC-HA/PTX3 complex) is about 50% or more free from components that normally accompany it in its native state, for example, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% free from components that normally accompany it in its native state.

As used herein, "biological activity" means the activity of polypeptides and polysaccharides of the fetal support tissue comprising native HC-HA/PTX3 or HA (which exists as native HC-HA/PTX3 in fetal support tissue) or any other component of the fetal support tissue and a combination thereof. In some embodiments, the biological activity of polypeptides and polysaccharides found in the fetal tissue support product is anti-inflammatory, anti-scarring, or anti-adhesion. In some embodiments, the biological activity refers to the in vivo activities of the native HC-HA/PTX3 complex in the fetal support tissue product or physiological responses that result, upon in vivo administration of the fetal support tissue. In some embodiments, the biological activity of native HC-HA/PTX3 complex in the fetal support tissue is substantially preserved. In some embodiments, the activity of polypeptides and polysaccharides found in the fetal tissue support product is to promote regenerative wound healing. In some embodiments, the activity of polypeptides and polysaccharides found in the fetal support tissue is to prevent scarring. In some embodiments, the activity of polypeptides and polysaccharides found in the fetal support tissue is to reduce inflammation. Biological activity, thus, encompasses therapeutic effects and pharmaceutical activity of the fetal support tissue compositions, such as for example, HA, native HC-HA/PTX3 complex and a combination thereof, or any other composition, or components of the fetal support tissue as disclosed herein.

As used herein, "structural integrity" means the integrity of stroma and basement membrane that make up the fetal support tissue.

As used herein, a "purified" native HC-HA/PTX3 (nHC-HA/PTX3) complex refers to an HC-HA/PTX3 complex that is purified from a biological source such as a cell, a tissue, or a biological fluid. In some embodiments, a purified native HC-HA/PTX3 (nHC-HA/PTX3) complex refers to an HC-HA/PTX3 complex that is purified from human fetal support tissues. In some embodiments the nHC-HA/PTX3 is purified from amniotic membrane. In some embodiments the nHC-HA/PTX3 is purified from umbilical cord. In some embodiments, the purified native HC-HA/PTX3 complex is isolated and purified from fetal support tissue before pooling the fetal support tissue. In some embodiments, the purified native HC-HA/PTX3 complex is isolated and purified from fetal support tissue after pooling the fetal support tissue. In some embodiments, the nHC-HA/PTX3 is substantially isolated, wherein the substantially isolated occurs prior to or after pooling the fetal support tissue. In some embodiments, the substantially isolated HC-HA complex is derived from placenta, umbilical cord, chorion, amnion-chorion, placental amniotic membrane (PAM), umbilical cord amniotic membrane (UCAM), or any combinations thereof. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In all or either instances, the isolation of HC-HA complex may occur before or after pooling said fetal support tissue.

As used herein, "hyaluronan," "hyaluronic acid," or "hyaluronate" (HA) are used interchangeably to refer to a substantially non-sulfated linear glycosaminoglycan (GAG) with repeating disaccharide units of D-glucuronic acid and N-acetylglucosamine (D-glucuronosyl-N-acetylglucosamine).

As used herein, the term "tissue having unwanted changes" refers to tissue that is degenerated due to, for example, a degenerative disease (for example, arthritis, multiple sclerosis, Parkinson's disease, muscular dystrophy, and Huntington's disease) or aging; scar tissue; or damaged due to an insult, such as a burn, wound, laceration, injury, ulcer, surgery, or due to ischemia.

As used herein, the term "high molecular weight" or "HMW," as in high molecular weight hyaluronan (HMW HA), is meant to refer to HA that has a weight average molecular weight that is greater than about 500 kilodaltons (kDa), such as, for example, between about 500 kDa and about 10,000 kDa, between about 800 kDa and about 8,500 kDa, between about 1100 kDa and about 5,000 kDa, or between about 1400 kDa and about 3,500 kDa. In some embodiments, the HMW HA has a weight average molecular weight of 3000 kDa or greater. In some embodiments, the HMW HA has a weight average molecular weight of 3000 kDa. In some embodiments, the HMW HA is Healon® with a weight average molecular weight of about 3000 kDa. In some embodiments, HMW HA has a molecular weight of between about 500 kDa and about 10,000 kDa. In some embodiments, HMW HA has a molecular weight of between about 800 kDa and about 8,500 kDa. In some embodiments, HMW HA has a molecular weight of about 3,000 kDa.

As used herein, the term "low molecular weight" or "LMW," as in low molecular weight hyaluronan (LMW HA), is meant to refer to HA that has a weight average molecular weight that is less than 500 kDa, such as for example, less than about 400 kDa, less than about 300 kDa, less than about 200 kDa, less than about 100 kDa, less than about 50 kDa, less than about 40 kDa, less than about 30 kDa, less than about 20 kDa, about 200-300 kDa, about 1-300 kDa, about 15 to about 40 kDa, or about 8-10 kDa.

As used herein, pentraxin 3, or PTX3, protein or polypeptide refers to any PTX3 protein, including but not limited to, a native PTX3 protein, and a PTX3 protein extracted from cells or tissues. PTX3 include multimeric forms (e.g., homomultimer) of PTX3, including, but not limited to, dimeric, trimeric, tetrameric, pentameric, hexameric, octameric, and other multimeric forms.

The terms "effective amount" or "therapeutically effective amount," as used herein, refer to a sufficient amount of an agent or a compound being administered which will relieve to some extent one or more of the symptoms of the disease or condition being treated. In some embodiments, the result is a reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. An "effective amount" of a compound disclosed herein, is an amount effective to achieve a desired effect or therapeutic improvement without undue adverse side effects. It is understood that in some embodiments, "an effective amount" or "a therapeutically effective amount" varies from subject to subject, due to variation in metabolism of the composition, age, weight, general condition of the subject, the condition being treated, the severity of the condition being treated, and the judgment of the prescribing physician. In some embodiments, an effective amount is an amount of a product or compound sufficient to promote vasculogenesis or normal angiogenesis in a tissue.

As used herein, the terms "subject," "individual" and "patient" are used interchangeably. None of the terms are to be interpreted as requiring the supervision of a medical professional (e.g., a doctor, nurse, physician's assistant, orderly, hospice worker). As used herein, the subject is any animal, including mammals (e.g., a human or non-human animal) and non-mammals. In one embodiment of the methods and compositions provided herein, the mammal is a human.

As used herein, the terms "treat," "treating" or "treatment," and other grammatical equivalents, include alleviating, abating or ameliorating one or more symptoms of a disease or condition, ameliorating, preventing or reducing the appearance, severity or frequency of one or more additional symptoms of a disease or condition, ameliorating or preventing the underlying metabolic causes of one or more symptoms of a disease or condition, inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically. In a non-limiting example, for prophylactic benefit, a native HC-HA/PTX3 complex or composition disclosed herein is administered to an individual at risk of developing a particular disorder, predisposed to developing a particular disorder, or to an individual reporting one or more of the physiological symptoms of a disorder.

Compositions

As used herein, the term "composition" refers to all combinations of two or more substances and includes all composite articles, whether resulting from chemical union or of mechanical mixture, or whether they be gases, fluids, powders, or solids. As used herein "compositions" of fetal support tissue can refer to any and all forms of fetal support tissues including isolated fetal support tissue, such as for example, isolated HA, nHC-HA/PTX3, extracts, sheet-form, non-sheet form, powders, gels, solutions, bioactive components of fetal support tissue in any and all forms. Fetal support tissue contains several innate biological factors useful for a number of purposes, including wound healing and reducing inflammation and scarring. Characterization data show that the extracellular matrix (ECM) of AM and UC are enriched in hyaluronic acid (HA) having a critical or key matrix component called, the native HC-HA/PTX3 (nHC-HA/PTX3) complex (HC-HA/PTX3" denotes Heavy Chain 1-Hyaluronic Acid-Pentraxin 3; "-" denoting covalent linkage and "/" denoting non-covalent tight binding) is a unique extracellular matrix from the birth tissue, i.e., AM and UC. Native HC-HA/PTX3 is isolated from the fetal support tissue obtained from a human or animal. Disclosed herewith are pooled fetal support tissue material comprising native HC-HA/PTX3 (nHC-HA/PTX3) complex. The nHC-HA/PTX3 complex—high molecular weight (HMW) hyaluronan (HA) covalently linked with heavy chain (HC) 1 from inter-α-trypsin inhibitor and further complexed with pentraxin3 (PTX3)—is one key active component of umbilical cord and amniotic membrane that is responsible for their therapeutic effects to promote regenerative wound healing. Accordingly, generation of a fetal support tissue product (e.g., an amniotic membrane and umbilical cord extract for use in wound healing) with a high yield of HA complex or nHC-HA/PTX3, is critical. A process that is able to generate fetal support tissue products, compositions, extracts or a combination thereof, while preventing degradation of bioactive components, e.g., HC-HA/PTX3 complex, extra cellular matrices, cytokines, growth factors etcetera is key to the generation of clinically suitable product. Because of the wide clinical application, it is important to find ways to process fetal support tissue extracts or compositions in which donor-to-donor variability is significantly reduced.

Disclosed herein are systems, methods, compositions, or devices to generate fetal support tissue with significantly reduced donor variability. Disclosed herein are fetal support tissue pooled from multiple donors. Pooling of fetal support tissues from multiple donors mitigates donor-to-donor variability. Disclosed herein are pooled fetal support tissues that are processed before or after lyophilization. The process of lyophilization as disclosed herein results in fetal support tissue compositions with reduced degradation. Lyophilization as disclosed herein also increases the concentration of bioactive composition for example, increasing the yield of nHC-HA/PTX3, hyaluronan (HA), growth factors and cytokines, other bioactive factors, while also preserving the stability and potency of the fetal support tissue extracts, composition, or products.

Fetal support tissue is obtained from donors following delivery. In some embodiments, the fetal support tissue may comprise at least 5 grams (g), 10 g, 15 g, 20 g of amniotic membrane per donor (wet weight); or at least 0.3 grams (g), 0.4 g, 0.5 g. 0.6 g, 0.7 g, or 0.8 g dry weight (e.g. lyophilized weight). In some embodiments, the fetal support tissue may comprise at least 20 grams (g), 25 g, 30 g, 35 g, 40 g, 45 g, 50 g of umbilical cord tissue per donor (wet weight); or at least 0.7 grams (g), 0.8 g, 0.9 g. 1.0 g, 1.1 g, or 1.2 g dry weight (e.g. lyophilized weight). The pooled fetal support tissue described herein can be processed to isolate or purify nHC-HA/PTX3 complex.

In some embodiments, the pooled fetal support tissue disclosed herein can have a therapeutically effective amount of nHC-HA/PTX3. In some embodiments a therapeutically effective amount of nHC-HA/PTX3 is about 0.1 mg per 100 mg of pooled fetal support tissue to about 10 mg per 100 mg of pooled fetal support tissue. In some embodiments a therapeutically effective amount of nHC-HA/PTX3 is about 1 mg per 60 g of pooled fetal support tissue. For example, a therapeutically effective amount of nHC-HA/PTX3 is about 1 mg per 10 g of pooled amniotic membrane. In some embodiments a therapeutically effective amount of nHC-HA/PTX3 is about 0.1 mg per 100 mg of pooled fetal support tissue to about 0.5 mg per 100 mg of pooled fetal support tissue, about 0.1 mg per 100 mg of pooled fetal support tissue to about 1 mg per 100 mg of pooled fetal support tissue, about 0.1 mg per 100 mg of pooled fetal support tissue to about 2 mg per 100 mg of pooled fetal support tissue, about 0.1 mg per 100 mg of pooled fetal support tissue to about 3 mg per 100 mg of pooled fetal support tissue, about 0.1 mg per 100 mg of pooled fetal support tissue to about 4 mg per 100 mg of pooled fetal support tissue, about 0.1 mg per 100 mg of pooled fetal support tissue to about 5 mg per 100 mg of pooled fetal support tissue, about 0.1 mg per 100 mg of pooled fetal support tissue to about 10 mg per 100 mg of pooled fetal support tissue, about 0.5 mg per 100 mg of pooled fetal support tissue to about 1 mg per 100 mg of pooled fetal support tissue, about 0.5 mg per 100 mg of pooled fetal support tissue to about 2 mg per 100 mg of pooled fetal support tissue, about 0.5 mg per 100 mg of pooled fetal support tissue to about 3 mg per 100 mg of pooled fetal support tissue, about 0.5 mg per 100 mg of pooled fetal support tissue to about 4 mg per 100 mg of pooled fetal support tissue, about 0.5 mg per 100 mg of pooled fetal support tissue to about 5 mg per 100 mg of pooled fetal support tissue, about 0.5 mg per 100 mg of pooled fetal support tissue to about 10 mg per 100 mg of pooled fetal support tissue, about 1 mg per 100 mg of pooled fetal support tissue to about 2 mg per 100 mg of pooled fetal support tissue, about 1 mg per 100 mg of pooled fetal support tissue to about 3 mg per 100 mg of pooled fetal support tissue, about 1 mg per 100 mg of pooled fetal support tissue to about 4 mg per 100 mg of pooled fetal support tissue, about 1 mg per 100 mg of pooled fetal support tissue to about 5 mg per 100 mg of pooled fetal support tissue, about 1 mg per 100 mg of pooled fetal support tissue to about 10 mg per 100 mg of pooled fetal support tissue, about 2 mg per 100 mg of pooled fetal support tissue to about 3 mg per 100 mg of pooled fetal support tissue, about 2 mg per 100 mg of pooled fetal support tissue to about 4 mg per 100 mg of pooled fetal support tissue, about 2 mg per 100 mg of pooled fetal support tissue to about 5 mg per 100 mg of pooled fetal support tissue, about 2 mg per 100 mg of pooled fetal support tissue to about 10 mg per 100 mg of pooled fetal support tissue, about 3 mg per 100 mg of pooled fetal support tissue to about 4 mg per 100 mg of pooled fetal support tissue, about 3 mg per 100 mg of pooled fetal support tissue to about 5 mg per 100 mg of pooled fetal support tissue, about 3 mg per 100 mg of pooled fetal support tissue to about 10 mg per 100 mg of pooled fetal support tissue, about 4 mg per 100 mg of pooled fetal support tissue to about 5 mg per 100 mg of pooled fetal support tissue, about 4 mg per 100 mg of pooled fetal support tissue to about 10 mg per 100 mg of pooled fetal support tissue, or about 5 mg per 100 mg of pooled fetal support tissue to about 10 mg per 100 mg of pooled fetal support tissue. In some embodiments a therapeutically effective amount of nHC-HA/PTX3 is about 0.1 mg per 100 mg of pooled fetal support tissue, about 0.5 mg per 100 mg of pooled fetal support tissue, about 1 mg per 100 mg of pooled fetal support tissue, about 2 mg per 100 mg of pooled fetal support tissue, about 3 mg per 100 mg of pooled fetal support tissue, about 4 mg per 100 mg of pooled fetal support tissue, about 5 mg per 100 mg of pooled fetal support tissue, or about 10 mg per 100 mg of pooled fetal support tissue. In some embodiments a therapeutically effective amount of nHC-HA/PTX3 is at least about 0.1 mg per 100 mg of pooled fetal support tissue, about 0.5 mg per 100 mg of pooled fetal support tissue, about 1 mg per 100 mg of pooled fetal support tissue, about 2 mg per 100 mg of pooled fetal support tissue, about 3 mg per 100 mg of pooled fetal support tissue, about 4 mg per 100 mg of pooled fetal support tissue, or about 5 mg per 100 mg of pooled fetal support tissue. In some embodiments a therapeutically effective amount of nHC-HA/PTX3 is at most about 0.5 mg per 100 mg of pooled fetal support tissue, about 1 mg per 100 mg of pooled fetal support tissue, about 2 mg per 100 mg of pooled fetal support tissue, about 3 mg per 100 mg of pooled fetal support tissue, about 4 mg per 100 mg of pooled fetal support tissue, about 5 mg per 100 mg of pooled fetal support tissue, or about 10 mg per 100 mg of pooled fetal support tissue.

In some embodiments, a therapeutically effective amount of nHC-HA/PTX3 comprises about 0.1 g per 10 g of wet tissue to about 2 g per 10 g of wet tissue. In some embodiments, a therapeutically effective amount of nHC-HA/PTX3 comprises about 0.1 g per 10 g of wet tissue to about 0.2 g per 10 g of wet tissue, about 0.1 g per 10 g of wet tissue to about 0.5 g per 10 g of wet tissue, about 0.1 g per 10 g of wet tissue to about 1 g per 10 g of wet tissue, about 0.1 g per 10 g of wet tissue to about 2 g per 10 g of wet tissue, about 0.2 g per 10 g of wet tissue to about 0.5 g per 10 g of wet tissue, about 0.2 g per 10 g of wet tissue to about 1 g per 10 g of wet tissue, about 0.2 g per 10 g of wet tissue to about 2 g per 10 g of wet tissue, about 0.5 g per 10 g of wet tissue to about 1 g per 10 g of wet tissue, about 0.5 g per 10 g of wet tissue to about 2 g per 10 g of wet tissue, or about 1 g per 10 g of wet tissue to about 2 g per 10 g of wet tissue. In some embodiments, a therapeutically effective amount of nHC-HA/PTX3 comprises about 0.1 g per 10 g of wet tissue, about 0.2 g per 10 g of wet tissue, about 0.5 g per 10 g of wet tissue, about 1 g per 10 g of wet tissue, or about 2 g per 10 g of wet tissue. In some embodiments, a therapeutically effective amount of nHC-HA/PTX3 comprises at least about 0.1 g per 10 g of wet tissue, about 0.2 g per 10 g of wet tissue, about 0.5 g per 10 g of wet tissue, or about 1 g per 10 g of wet tissue. In some embodiments, a therapeutically effective amount of nHC-HA/PTX3 comprises at most about 0.2 g per 10 g of wet tissue, about 0.5 g per 10 g of wet tissue, about 1 g per 10 g of wet tissue, or about 2 g per 10 g of wet tissue.

Cryopreservation

In some embodiments, the fetal support tissue is pooled then frozen for cryopreservation. In some embodiments, the fetal support tissue is frozen for cryopreservation and pooled after freezing. In some embodiments, cryopreserving the fetal support tissue does not destroy the integrity of the fetal support tissue extracellular matrix. In some embodiments, the fetal support tissue is exposed to a liquid gas (e.g., liquid nitrogen or liquid hydrogen). In some embodiments, the fetal support tissue is exposed to liquid nitrogen. In some embodiments, the fetal support tissue does not contact the liquid gas. In some embodiments, the fetal support tissue is placed in a container and the container is contacted with liquid gas. In some embodiments, the fetal support tissue is exposed to the liquid gas until the fetal support tissue is frozen.

As used herein, "morsel" refers to particles of tissue ranging in size from about 0.1 mm to about 1.0 cm in length, width, or thickness that have been obtained from a larger piece of tissue. A "morsel" as described herein, retains the characteristics of the tissue from which it was obtained and upon inspection is identifiable as said tissue. As used herein, the terms "morselized," "morselizing," and "morselization" refer to actions involving the "morsels" of the present application. In some embodiments, the morselized fetal support tissue, generated prior to pooling the fetal support tissue or after pooling the fetal support tissue, is further processed into a solution, suspension, or emulsion by mixing the morselized fetal support tissue with a carrier. In some embodiments, the morselized fetal support tissue is formulated into a solution, suspension, paste, ointment, oil emulsion, cream, lotion, gel, a patch, sticks, film, paint, or a combination thereof. In some embodiments, the morselized fetal support tissue is contacted with a patch or wound dressing. In some embodiments, the morselized fetal support tissue is formulated for parenteral injection, is administered as a sterile solution, suspension, or emulsion, or is formulated for inhalation.

Disclosed herein are processes for generating fetal support tissue while preserving the biological activity of the fetal support tissue, including components of the fetal support tissue, such as nHC-HA/PTX3, HA, cytokines, growth factors, or other bioactive components. The processing of fetal support tissue to preserve the potency of HC-HA/PTX3 in AM/UC is disclosed throughout the specification and claims. In some embodiments, a fetal support tissue comprising "morselization" also refers to "micronization". Henceforth, as used herein, the term "micronize" is used interchangeably to mean morselize, grind, mince, blend, mix, pulverize, powder, homogenize and any combination thereof of fetal support tissue. In some embodiments, the fetal support tissue which can comprise a mixture of amniotic membrane tissue and umbilical cord tissue in any ratio from 0.001:99.999 w/w % to 99.999:0.001 w/w % is micronized prior to pooling and/or lyophilizing fetal support tissue or micronized after pooling and/or lyophilizing the fetal support tissue that is taken from either fresh or frozen tissue through the use of any micronizing tool known to one of skill in the art such as, for example, tissue grinder, sonicator, bread beater, freezer/mill, blender, mortar/pestle, Roto-stator, kitchen chopper, grater, ruler and scalpel to yield morsels ranging in size from about 0.1 mm to about 1.0 cm in length, width, or thickness. In some embodiments, the resulting morsels are micronized to yield consistently sized particles. In some embodiments, the resulting morsels are used wet, partially dehydrated, or essentially dehydrated by any means known to one of skill in the art such as, for example, centrifuge, ultracentrifuge or lyophilization. In some embodiments, the resulting fetal support tissue is used immediately or stored for later use in any type of contained known to one of skill in the art such as, for example, pouch, jar, bottle, tube, ampule, and pre-filled syringe. In some embodiments, the micronized fetal support tissue is sterilized by any method known to one of skill in the art such as, for example, γ radiation.

As used herein, "pulverized fetal support tissue" means a fetal support tissue comprising "micronized" tissue that has been broken up (or, disassociated) and in some instances, pulverizing is used interchangeably as micronized. In some embodiments, the pulverized pooled fetal support tissue is a dry powder. In some embodiments, the pulverized pooled and/or lyophilized fetal support tissue is a dry powder pooled after the micronizing. In some embodiments, isolated fetal support tissue is used to generate a micronized fetal support tissue. In some embodiments, fetal support tissue is used to generate a micronized fetal support tissue prior to pooling the fetal support tissue. In some embodiments, fetal support tissue is used to generate a micronized fetal support tissue after pooling the fetal support tissue. In some embodiments, fetal support tissue is used to generate a micronized fetal support tissue prior to pooling the fetal support tissue. In some embodiments, fetal support tissue is used to generate a micronized fetal support tissue prior to lyophilizing the fetal support tissue. In some embodiments, fetal support tissue is used to generate a micronized fetal support tissue prior/after lyophilizing the fetal support tissue. In some embodiments, fetal support tissue is used to generate a micronized fetal support tissue prior to pooling the fetal support tissue but before or after lyophilizing the fetal support tissue. In some embodiments, fetal support tissue is used to generate a micronized fetal support tissue after pooling the fetal support tissue but before or after lyophilizing the fetal support tissue. In some embodiments, the micronized fetal support tissue that is processed prior to pooling the fetal support tissue or after pooling the fetal support tissue and before or after lyophilizing the fetal support tissue, is further processed into a solution, suspension, or emulsion by mixing the fetal support tissue powder with a carrier. In some embodiments, the micronized fetal support tissue (generated prior to or after pooling, and/or before or after lyophilizing and/or a combination thereof) is formulated into a solution, suspension, paste, ointment, oil emulsion, cream, lotion, gel, a patch, sticks, film, paint, or a combination thereof. In some embodiments, the micronized fetal support tissue is contacted with a patch or wound dressing. In some embodiments, the micronized fetal support tissue is formulated for parenteral injection, is administered as a sterile solution, suspension, or emulsion, or is formulated for inhalation.

In certain embodiments disclosed herein are methods and processes for generating fetal support tissue while preserving the biological activity of HC-HA/PTX3 from the fetal support tissue. In certain embodiments, the processes comprise pooling steps which reduce variability of the amount or activity of HC-HA/PTX3. In some embodiments, the isolated fetal support tissue is micronized by any suitable method. In some embodiments, the lyophilizing of the fetal support tissue occurs prior to micronizing the pooled fetal support tissue. In some embodiments, the lyophilizing of the fetal support tissue may occur after the micronizing the pooled fetal support tissue. In some embodiments, the isolated fetal support tissue is micronized by use of a pulverizer (e.g., a Bessman Tissue Pulverizer, a Biospec biopulverizer, or a Covaris CryoPrep). In some embodiments, the isolated fetal support tissue is micronized by use of a tissue grinder (e.g., a Potter-Elvehjem grinder or a Wheaton Overhead Stirrer). In some embodiments, the isolated fetal support tissue is micronized by use of a sonicator. In some embodiments, the isolated fetal support tissue is micronized by use of a bead beater. In some embodiments, the isolated fetal support tissue is pulverized by use of a freezer/mill (e.g., a SPEX® SamplePrep Freezer/Mill or a Retsch Ball Mill). In some embodiments, the isolated fetal support tissue is micronized by use of a pestle and mortar. In some embodiments, the isolated fetal support tissue is micronized by manual use of a pestle and mortar. Disclosed herein are processes for generating fetal support tissue while preserving the biological activity of the fetal support tissue, including components of the fetal support tissue, such as HC-HA/PTX3, HA, growth factors, cytokines or other active components as disclosed throughout the specification and claims.

Disclosed herein are processes for generating fetal support tissue while preserving the biological activity of the fetal support tissue, including components of the fetal support tissue, such as HC-HA/PTX3, HA, growth factors, cytokines or other active components as disclosed throughout the specification and claims. In some embodiments, the fetal support tissue can be a sheet or non-sheet form of varying sizes of sheet product. In some embodiments, the pooled fetal support tissue is micronized prior to freezing of the fetal support tissue. In some embodiments, the pooled fetal support tissue is micronized after freezing of the fetal support tissue. In some embodiments, the fetal support tissue is not pooled prior to micronization. In some embodiments, the fetal support tissue is pooled after micronization. In some embodiments, the fetal support tissue is micronized prior to lyophilization and before or after pooling. In some embodiments, the fetal support tissue is micronized after lyophilization and before or after pooling. In some embodiments, pooled fetal support tissue is lyophilized prior to micronization, devitalization, decellularization, cryopulverization, sterilization, cryopreservation, purification of dry or wet fetal support tissue extract, or a combination thereof. In some embodiments, the pooled fetal support tissue is lyophilized after micronization, sieving, centrifugation, filtration, devitalization, decellularization, cryopulverization, sterilization, cryopreservation, purification, of dry or wet fetal support tissue extract, or a combination thereof. In some embodiments, the not pooled fetal support tissue is lyophilized prior to sieving, micronization, devitalization, decellularization, cryopulverization, sterilization, cryopreservation, purification of dry or wet fetal support tissue, or a combination thereof. In some embodiments, the not pooled fetal support tissue is not lyophilized prior to micronization, devitalization, decellularization, cryopulverization, sterilization, sieving, centrifugation, filtration, cryopreservation, purification or of dry or wet fetal support tissue extract, or a combination thereof. In some embodiments, the micronization, devitalization, decellularization, of dry or wet tissue, cryopulverization, sterilization, cryopreservation, purification, or a combination thereof, occurs prior to pooling the fetal support tissue wherein the fetal support tissue can be fresh, or frozen, or not frozen, or previously frozen or undergoing freezing. In some embodiments, the micronization, devitalization, decellularization, of dry or wet tissue, cryopulverization, sterilization, cryopreservation, purification or a combination thereof, occurs on pooled fetal support tissue (i.e. after pooling) and is generated from pooled fresh, pooled frozen, previously pooled then frozen or pooled right before freezing fetal support tissue (decellularization) or is generated from pooled tissue after freezing (decellularization) of the fetal support tissue. In some embodiments, the pooled fetal support tissue can be used to yield an extract, from which native HC-HA/PTX3 complex (nHC-HA/PTX3) can be purified by any suitable method. In some embodiments the pooling strategy described herein can be used to manufacture by purification of nHC-HA/PTX3. In some embodiments, the pooled fetal support tissue product that is purified can be an extract, a composition, or a product in any of the forms disclosed herein, wherein the product or extract is purified through centrifugation. Disclosed herein are processes for generating fetal support tissue while preserving the biological activity of the fetal support tissue, including components of the fetal support tissue, such as HC-HA/PTX3, HA, growth factors, cytokines or other active components as disclosed throughout the specification and claims.

Various Forms of the Fetal Support Tissues

In some embodiments, a fetal support tissue comprises micronized fetal support tissue. In some embodiments, a fetal support tissue can be a fetal support tissue graft, a fetal support tissue sheet, a fetal support tissue homogenate, a fetal support tissue extract. In some embodiments, the fetal support tissue is lyophilized. In some embodiments, the fetal support tissue undergoes centrifugation or ultracentrifugation. In some embodiments, the fetal support tissue is a liquid. In some embodiments the fetal support tissue that is a liquid undergoes filtration. In some embodiments, the fetal support tissue is a powder. In some embodiments, the fetal support tissue that is a powder is sieved. In some embodiments, the fetal support tissue is devitalized or decellularized. In some embodiments, the fetal support tissue is terminally sterilized. In some embodiments, the fetal support tissue is a purified native HC-HA/PTX3 complex. In some embodiments, the fetal support tissue is an extract of a fetal support tissue. In some embodiments, the fetal support tissue is a placental amniotic membrane, umbilical cord, umbilical cord amniotic membrane, chorion, amnion-chorion, placenta, amniotic stroma, amniotic jelly, or any combination thereof.

In some embodiments, the fetal support tissue comprises umbilical cord, an amniotic membrane, or umbilical cord amniotic membrane. In some embodiments, the umbilical cord comprises umbilical cord, amniotic membrane, and at least some Wharton's jelly. In some embodiments, the umbilical cord comprises umbilical cord, amniotic membrane, and Wharton's jelly. In some embodiments, the umbilical cord comprises umbilical cord, amniotic membrane, and is substantially free of Wharton's jelly In some embodiments, the umbilical cord lacks umbilical cord vein and arteries. In some embodiments, the umbilical cord contains umbilical cord vein and arteries.

In some embodiments, the fetal support tissue comprises an extract of a fetal support tissue. In some embodiments, the fetal support tissue comprises native HC-HA/PTX3 complex (nHC-HA/PTX3). In some embodiments, the fetal support tissue consists essentially of nHC-HA/PTX3. In some embodiments, the fetal support tissue comprises other components such as for example, other extracellular matrices, growth factors, cytokines and other bioactive components that can be isolated from fetal support tissue. Disclosed herein are processes for generating fetal support tissue while preserving the biological activity of the fetal support tissue, including components of the fetal support tissue, such as for example, HA, HC-HA/PTX3 growth factors, cytokines, and other active biological components, of which the potency of HC-HA/PTX3 can be monitored to ensure it is adequate preservation as disclosed throughout the specification and claims. In certain embodiments, the HC-HA/PTX3 is biologically active.

Grinding/Cryopulverization

In some embodiments, the fetal support tissue is ground by any suitable method before or after pooling and before or after lyophilization. In some embodiments, the pooling before or after lyophilization of the fetal support tissue occurs on fresh, raw, newly frozen, or previously frozen fetal support tissue. Disclosed herein are exemplary procedures of micronization or cryopulverizing the fetal support tissue. In some embodiments, the fetal support tissue is pooled prior to micronization or prior to cryopulverization. In some embodiments the fetal support tissue is pooled after micronization or after cryopulverization. In some embodiments, grinding the fetal support tissue comprises cryopulverizing the fetal support tissue. In some embodiments, cryopulverizing fetal support tissue comprises pulverizing, micronizing, or otherwise fragmenting the fetal support tissue while the fetal support tissue is in a frozen (e.g., exposed to a temperature below 0° C., −20° C., −40° C., −50° C., −60° C., −70° C., −75° C., −80° C., −90° C., −100° C.) or chilled state. In some embodiments, cryopulverizing the fetal support tissue comprises micronizing the fetal support tissue in a cryogenically controlled environment. In some embodiments, cryopulverizing the fetal support tissue comprises micronizing the fetal support tissue after the fetal support tissue has been immersed in or exposed to (e.g., directly, or indirectly) liquid nitrogen. In some embodiments, cryopulverizing the fetal support tissue comprises micronizing the fetal support tissue while the fetal support tissue is immersed in or exposed to (e.g., directly, or indirectly) liquid nitrogen. In some embodiments, cryopulverizing the fetal support tissue comprises placing the fetal support tissue in a grinding container and immersing the grinding container in liquid nitrogen prior to grinding. In some embodiments, the grinding container is immersed in liquid nitrogen for at least 1 minute of the grinding process. In some embodiments, cryopulverizing fetal support tissue comprises exposing frozen fetal support tissue to a hammer or rotating blade. In some embodiments, cryopulverizing fetal support tissue comprises exposing frozen fetal support tissue to an impactor. In some embodiments, the impactor is driven by electromagnets. In some embodiments, the fetal support tissue is cryopulverized by use of a Freezer Mill. In some embodiments, the fetal support tissue is cryopulverized by use of a mortar and pestle. In some embodiments, the fetal support tissue is cryopulverized by use of a blender. In some embodiments, the fetal support tissue is cryopulverized by use of a BioPulverizer. In some embodiments, cryopulverizing fetal support tissue in liquid nitrogen, as compared to grinding fetal support tissue that has not been frozen, avoids activating in the fetal support tissue protease and/or hyaluronidase, which may degrade proteins and hyaluronan in the fetal support tissue. Disclosed herein are processes for generating fetal support tissue while preserving the biological activity of the fetal support tissue, including components of the fetal support tissue, such as for example, HA, nHC-HA/PTX3, growth factors, cytokines, and other active biological components, of which the potency of HC-HA/PTX3 can be monitored to ensure its adequate preservation as disclosed throughout the specification and claims.

In some embodiments, cryopulverization reduces the fetal support tissue to a powder. In some embodiments, the particles comprising the powder are of uniform size distribution. In some embodiments, the particles comprising the powder are not of uniform size distribution. In some embodiments, the fetal support tissue is reduced to a particle size of less than about 1000 μm, 500 μm, 400 μm, 300 μm, 200 μm, 100 μm, 50 μm, 40 μm, 30 μm, 20 μm, 10 μm, 5 μm, 1 μm, 0.5 μm, 0.4 μm, 0.3 μm, 0.2 μm, or 0.1 μm. In some embodiments, the fetal support tissue is reduced to a particle size of less than 500 μm. In some embodiments, the fetal support tissue is reduced to a particle size of less than about 0.5 μm. In some embodiments, the fetal support tissue is reduced to a particle size of less than 0.3 μm.

Lyophilization

Disclosed herein are processes for generating fetal support tissue while preserving the biological activity of the fetal support tissue, including components of the fetal support tissue, such as nHC-HA/PTX3, HA, growth factors, cytokines or other active components as disclosed throughout the specification and claims. In some embodiments, lyophilization preserves the biological activity of HC-HA/PTX3. In some instances, the cryopreserved fetal support tissue or tissue product is placed in the vacuum chamber of a lyophilization device until all or substantially all fluid (e.g., water) has been removed. In some embodiments, the fetal support tissue is cryopreserved, before or after pooling. In certain embodiments, the pooled fetal support tissue has the water content reduced to 20% or less, 15%, or less, 10% or less, or 5% or less by weight. In certain embodiments the water content of the pooled fetal support tissue is 1% or greater, 2% or greater, 3% or greater, 5% or greater, or 10% or greater by weight. In some embodiments lyophilization is performed on fetal support tissue from individual and/or small pools or donors (e.g., 2, 3, 4 or, 5) before pooling. In some embodiments, the pooled fetal support tissue is lyophilized after pooling. In some embodiments, the pooled fetal support tissue is fresh, or newly frozen or previously stored frozen prior to or after lyophilization. In some embodiments, the pooled fetal support tissue is lyophilized and subsequently micronized, sieved, cryopreserved, sterilized, purified, centrifuged, filtered, or a combination of any of these thereof to allow a yield of different size. In some embodiments, the fetal support tissue is lyophilized before being pooled. In some embodiments, the fetal support tissue is not lyophilized before being pooled. In some embodiments, the fetal support tissue is not lyophilized prior to being pooled. In some embodiments, the fetal support tissue that is micronized, sieved, or cryopreserved, sterilized, purified, centrifuged, filtered, or a combination thereof to allow a yield of different size, occurs before or after being lyophilized. In some embodiments, the fetal support tissue is lyophilized and subsequently pooled after being micronized, sieved, or cryopreserved, sterilized, purified, centrifuged, filtered or a combination thereof, to allow a yield different size. In some embodiments, the pooled fetal support tissue is lyophilized following freezing. In some embodiments, the fetal support tissue is lyophilized then pooled following freezing by any suitable method (e.g., exposure to a liquid gas, placement in a freezer).

As disclosed herein, in some embodiments, fetal support tissue is pooled fetal support tissue, wherein fetal support tissue is pooled before or after lyophilization, wherein the fetal support tissue is pooled before or after micronization, sieving, or cryopulverizing, cryopreservation, centrifugation, filtration, sterilization, decellularization, devitalization, freezing, thawing, cutting, cleaning, or any other process as disclosed herein, and/or a combination thereof.

In some embodiments, the pooled fetal support tissue is frozen by exposure to a temperature below about 0° C. In some embodiments, the pooled fetal support tissue is frozen by exposure to a temperature below about –20° C. In some embodiments, the fetal support tissue is frozen by exposure to a temperature below about –40° C. In some embodiments, the fetal support tissue is frozen by exposure to a temperature below about –50° C. In some embodiments, the fetal support tissue is frozen by exposure to a temperature below about –60° C. In some embodiments, the fetal support tissue is frozen by exposure to a temperature below about –70° C. In some embodiments, the fetal support tissue is frozen by exposure to a temperature below about –75° C. In some embodiments, the fetal support tissue is frozen by exposure to a temperature below about –80° C. In some embodiments, the fetal support tissue is frozen by exposure to a temperature below about –90° C. In some embodiments, the fetal support tissue is frozen by exposure to a temperature below about –100° C. In some embodiments, the fetal support tissue is frozen by exposure to a liquid gas. For example, a liquid nitrogen gas. In some embodiments, the fetal support tissue is placed in a vacuum chamber of a lyophilization device until all or substantially all fluid (e.g., water) has been removed. In some embodiments, a cryopreserved fetal support tissue is lyophilized.

Generation of Fetal Support Tissues

In some embodiments, the fetal support tissue is derived from an umbilical cord (UC) tissue. In some embodiments, the fetal support tissue is derived from an amniotic membrane (AM) tissue. In some embodiments, the fetal support tissue is derived from an umbilical cord amniotic membrane tissue or in combination with any of the above. In some embodiments, the fetal support tissue comprises isolated fetal support tissue that does not comprise a vein or an artery. In some embodiments, the fetal support tissue comprises isolated fetal support tissue that does not comprise a vein or an artery, a cell with metabolic activity, wherein the natural structural integrity of the fetal support tissue is substantially preserved after initial procurement. In some embodiments, the fetal support tissue comprises isolated fetal support tissue that comprises a vein or an artery. In some embodiments, the fetal support tissue comprises isolated fetal support tissue that comprises a vein or an artery, a cell with metabolic activity, wherein the natural structural integrity of the fetal support tissue is substantially preserved after initial procurement. In some embodiments, the fetal support tissue comprises umbilical cord amniotic membrane and Wharton's Jelly. In some embodiments, the biological activity of various bioactive components such as, for example, HA, nHC-HA/PTX3 complex or composition in the fetal support tissue is substantially preserved. In some embodiments, the biological activity of the bioactive components, HA, and/or nHC-HA/PTX3 complex in the fetal support tissue is substantially preserved when processed (washed, cut, centrifuges, etc.) and frozen at 72 hours after delivery. Tissue that has been frozen can be frozen for at least 1 day, 5, days, 10 days, 20 days, 30 days or longer. In some embodiments, the biological activity of bioactive components, HA, or nHC-HA/PTX3 complex in the fetal support tissue is substantially preserved when processed (washed, cut etcetera) and frozen no more than 72 hours after delivery. In some embodiments, the biological activity of bioactive components, HA, or nHC-HA/PTX3 complex in the fetal support tissue is substantially preserved for at least 15 days. In some embodiments, the biological and structural integrity of the fetal support tissue is substantially preserved for at least 20 days after initial procurement. In some embodiments, the biological and structural integrity of the fetal support tissue is substantially preserved for at least 25 days after initial procurement. In some embodiments, the biological and structural integrity of the fetal support tissue is substantially preserved for at least 30 days after initial procurement. In some embodiments, the biological and structural integrity of the fetal support tissue is substantially preserved for at least 35 days after initial procurement. In some embodiments, the biological and structural integrity of the fetal support tissue is substantially preserved for at least 40 days after initial procurement. In some embodiments, the biological and structural integrity of the fetal support tissue is substantially preserved for at least 45 days after initial procurement. In some embodiments, the biological and structural integrity of the fetal support tissue is substantially preserved for at least 50 days after initial procurement. In some embodiments, the biological and structural integrity of the fetal support tissue is substantially preserved for at least 55 days after initial procurement. In some embodiments, the biological and structural integrity of the fetal support tissue is substantially preserved for at least 60 days after initial procurement. In some embodiments, the biological and structural integrity of the fetal support tissue is substantially preserved for at least 65 days after initial procurement. In some embodiments, the biological and structural integrity of the fetal support tissue is substantially preserved for at least 70 days after initial procurement. In some embodiments, the biological and structural integrity of the fetal support tissue is substantially preserved for at least 75 days after initial procurement. In some embodiments, the biological and structural integrity of the fetal support tissue is substantially preserved for at least 80 days after initial procurement. In some embodiments, the biological and structural integrity of the fetal support tissue is substantially preserved for at least 85 days after initial procurement. In some embodiments, the biological and structural integrity of the fetal support tissue is substantially preserved for at least 90 days after initial procurement. In some embodiments, the biological and structural integrity of the fetal support tissue is substantially preserved for at least 95 days after initial procurement. In some embodiments, the biological and structural integrity of the fetal support tissue is substantially preserved for at least 100 days after initial procurement. In some embodiments, the biological and structural integrity of the fetal support tissue is substantially preserved for at least 180 days after initial procurement. In some embodiments, the biological and structural integrity of the fetal support tissue is substantially preserved for at least 1 year after initial procurement. In some embodiments, the biological and structural integrity of the fetal support tissue is substantially preserved for at least 2 years after initial procurement. In some embodiments, the biological and structural integrity of the fetal support tissue is substantially preserved for at least 3 years after initial procurement. In some embodiments, the biological and structural integrity of the fetal support tissue is substantially preserved for at least 4 years after initial procurement. In some embodiments, the biological and structural integrity of the fetal support tissue is substantially preserved for at least 5 years after initial procurement. In some embodiments, the biological and structural integrity of the fetal support tissue is substantially preserved for one or more days to at least 5 years after initial procurement. In some embodiments, the fetal support tissue is obtained from an animal, a mammal e.g., a human or a non-human animal, such as for example, a primate, a cow, or a pig.

In some embodiments, the fetal support tissue is kept below 0° C. until donor and specimen eligibility has been determined. In some embodiments, the fetal support tissue is kept from between 0° C. to –80° C. until donor and specimen eligibility has been determined. In some embodiments, storing the fetal support tissue at –80° C. kills substantially all cells found in the fetal support tissue. In some embodiments, storing the fetal support tissue at –80° C. kills substantially all cells found in the fetal support tissue while maintaining or increasing the biological activity of the fetal support tissue (e.g., its anti-inflammatory, anti-scarring, anti-antigenic, and anti-adhesion properties) relative to fresh (i.e., non-frozen) fetal support tissue. In some embodiments, storing the fetal support tissue at –80° C. results in the loss of metabolic activity in substantially all cells found in the fetal support tissue. In some embodiments, the loss of metabolic activity may result in cell death. In some embodiments, the cells may lack metabolic activity while maintaining the biological activity of the fetal support tissue or any biomolecules present therein, including without limitation HC-HA/PTX3. In some embodiments, the fetal support tissue is dried. In some embodiments, the fetal support tissue is not dehydrated. Disclosed herein are processes for generating fetal support tissue while preserving the biological activity of the fetal support tissue, including components of the fetal support tissue, such as HC-HA/PTX3, HA, growth factors, cytokines or other active components as disclosed throughout the specification and claims.

Processing a Fetal Support Tissue

Figure 1A:
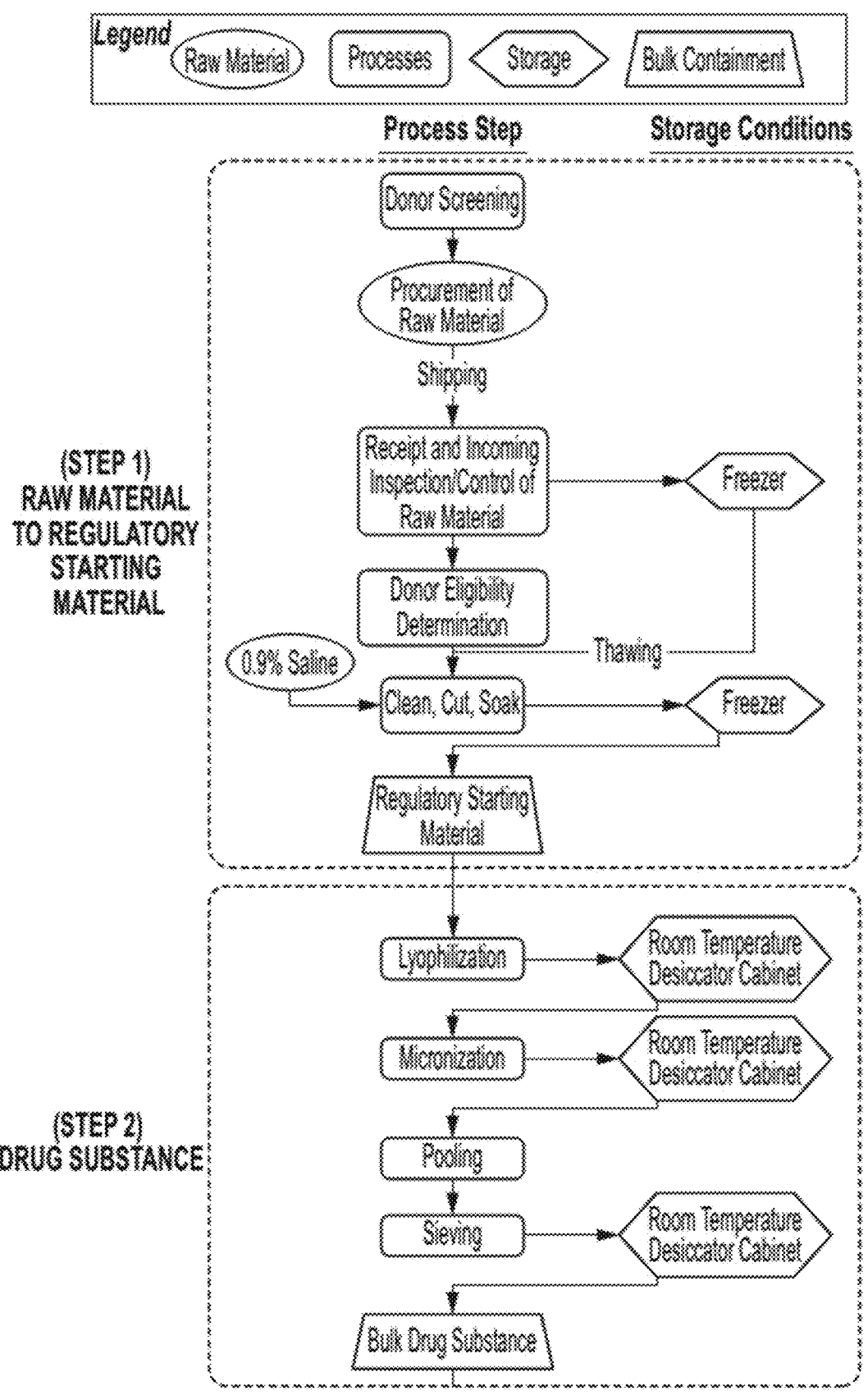
FIGS. 1A-1B show a flow chart illustrating an example of a process flow or method of producing a fetal support tissue product. The process flow shows the process steps from procurement of donor samples, cleaning, and processing (FIG. 1A) to the primary packaging (FIG. 1B) for powder or micronized forms processed by pooling multiple donors to decrease sample variability, increase consistency, increase yield, increased efficacy and uniform potency as disclosed herein.
Figure 1B:
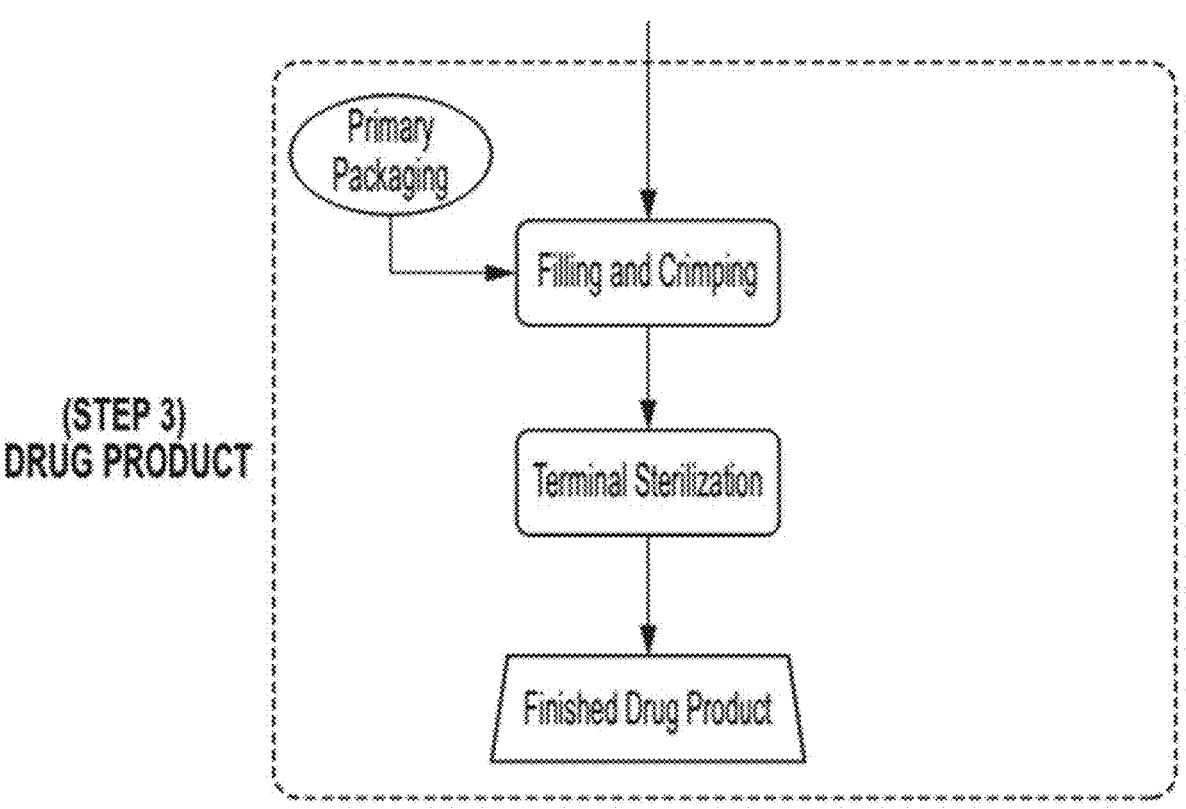
Figure 2A:
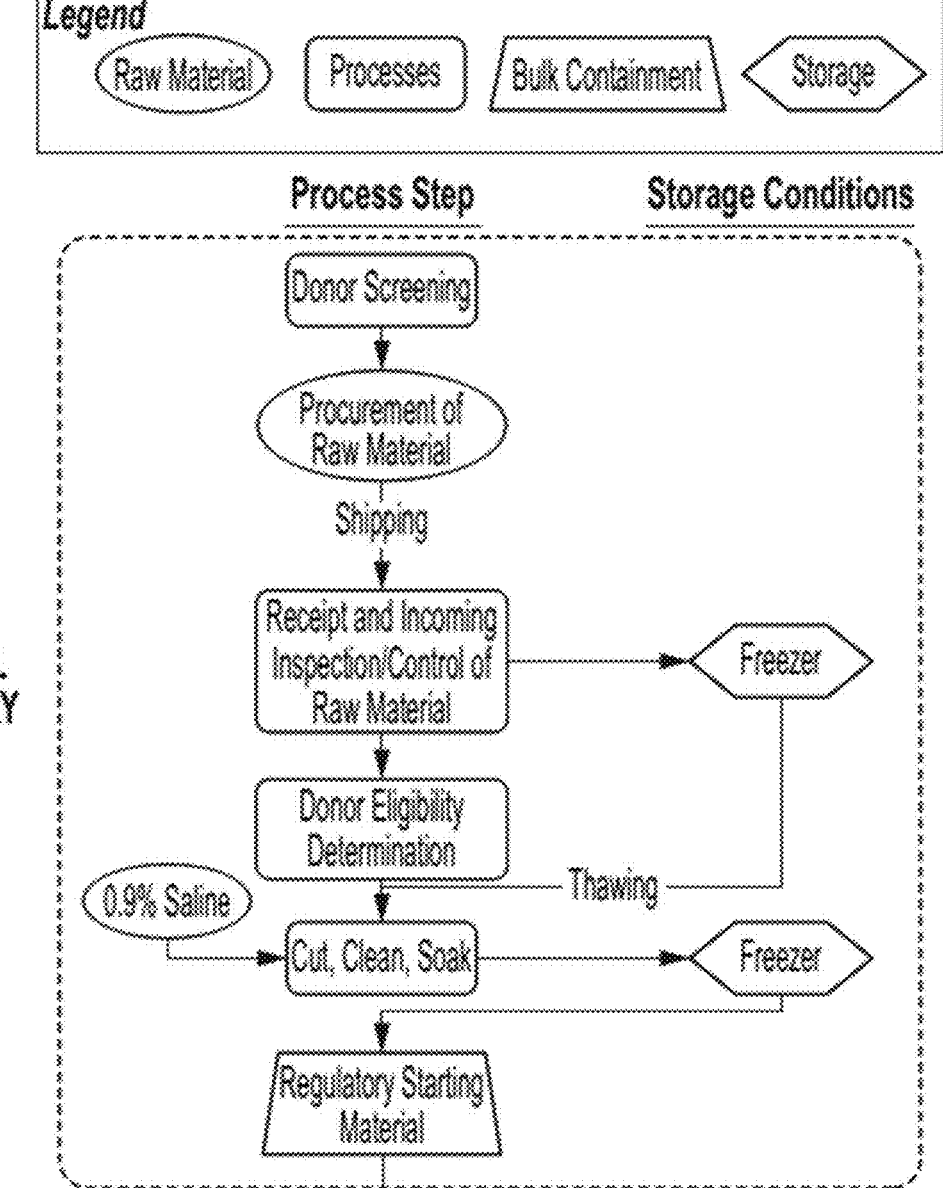
FIGS. 2A-2C show a flow chart illustrating an example of a process flow or method of producing a fetal support tissue product (drug substance process) in a liquid form by pooling multiple donors to increase yield and uniform potency. Illustrated is the process of sample receivership and cleaning (FIG. 2A), sample processing and pooling process flow (FIG. 2B) and receipt, storage and packaging of the drug product (FIG. 2C).
Figure 2B:
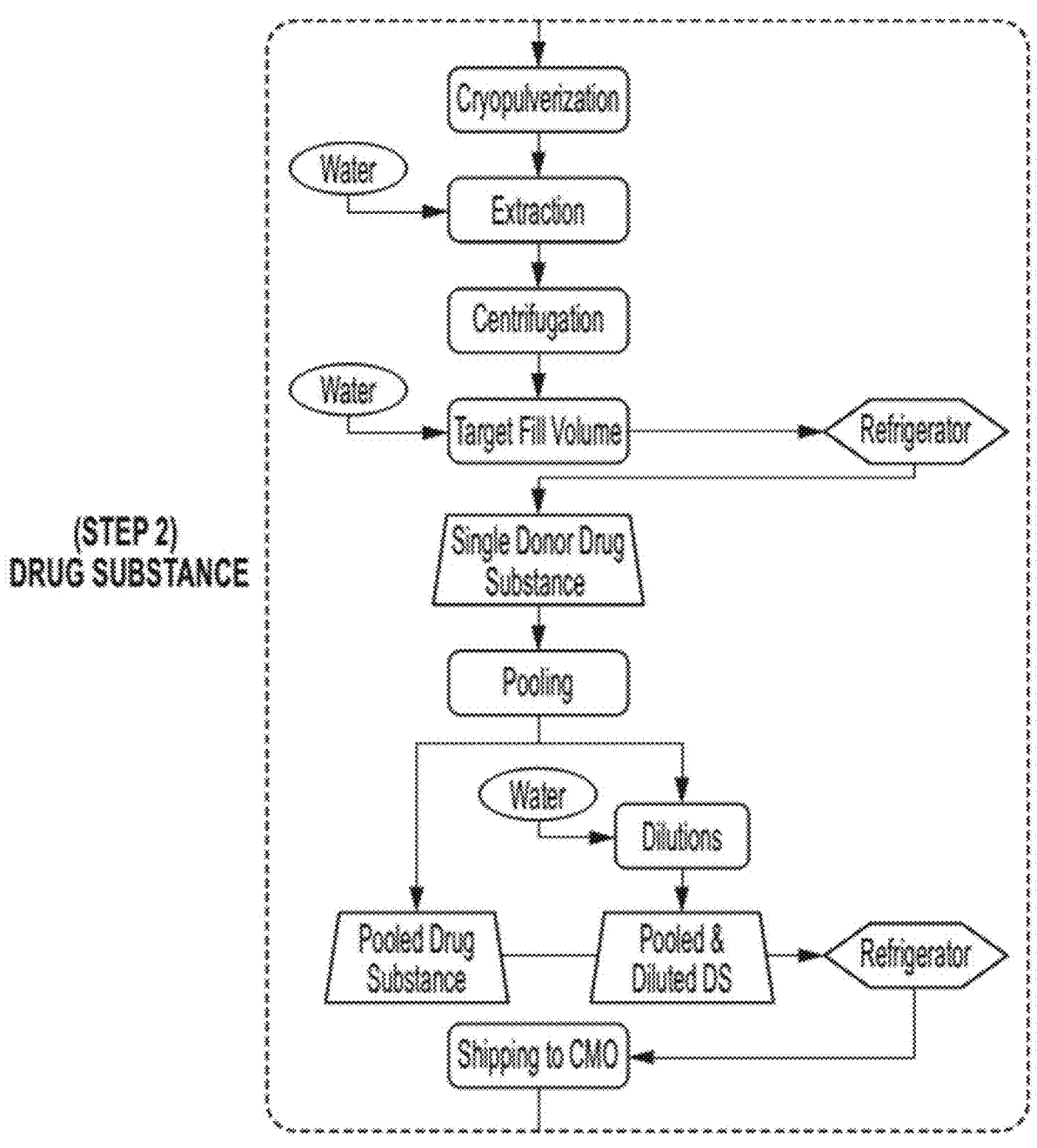
Figure 2C:
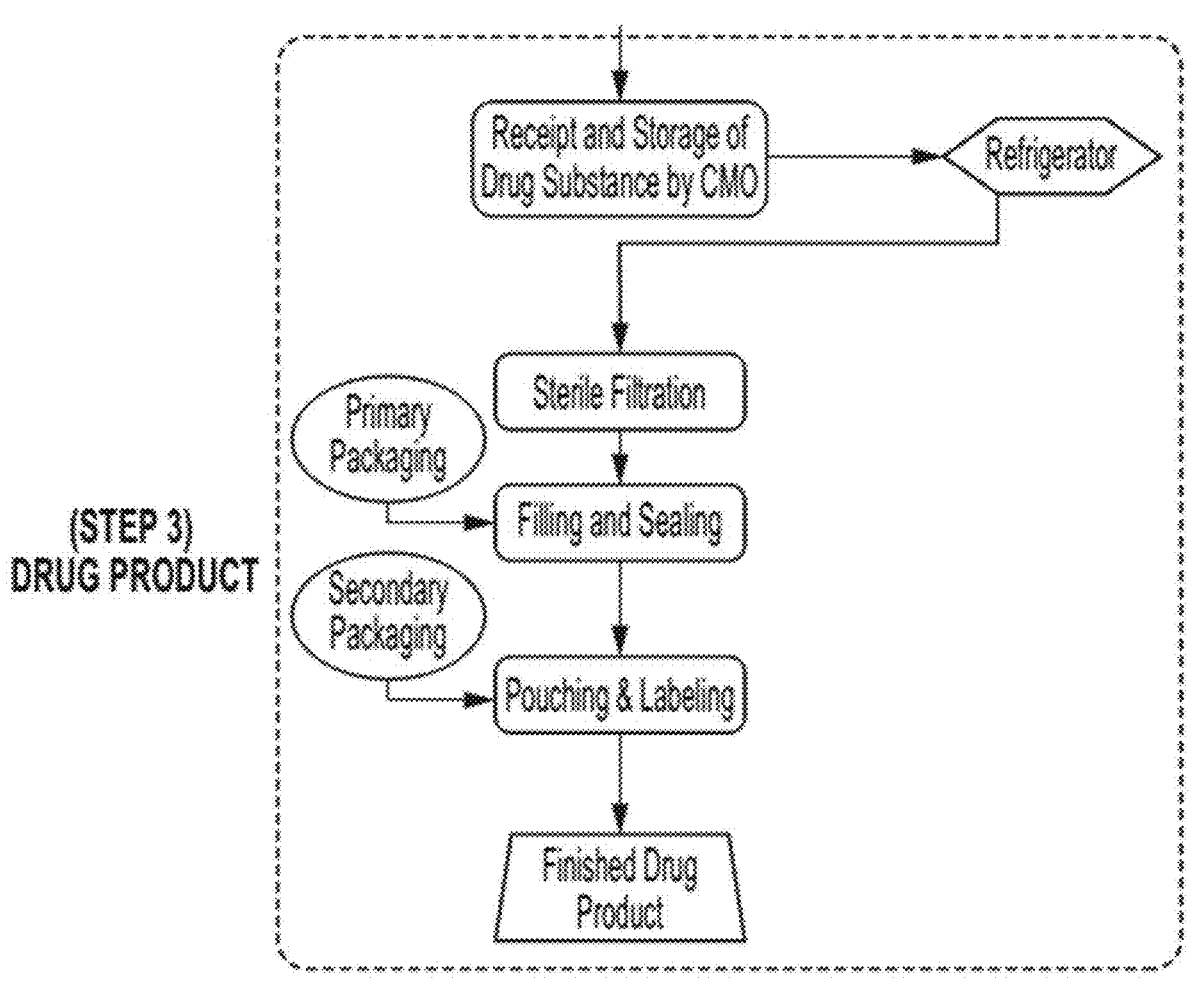

Disclosed herewith and throughout the disclosure are the fetal support tissue procurement and processing steps or protocols shown in detail in FIGS. 1A-1B and in FIGS. 2A, 2B and 2C. Whenever fetal support tissue is disclosed herein, it should be taken, though without limitations, that the fetal support tissue can be pooled fetal support tissue, wherein the pooling occurs prior to the prescribed fetal support tissue processing step or can be pooled fetal support tissue wherein the pooling occurs after the prescribed fetal support tissue processing steps shown in FIGS. 1A-1B and FIGS. 2A-2B and 2C.

In some embodiments, processing is done following Good Tissue Practices (GTP) to prevent introduction, transmission, contamination, or cross-contamination of potentially communicable diseases from donors.

In some embodiments, the fetal support tissue is tested for active viral infections such as for example, active HIV-1, HIV-2, HTLV-1, hepatitis B and C, West Nile virus, Cytomegalovirus and *Treponema pallidum* using FDA licensed screening test. In some embodiments, any indication that the tissue is contaminated with active viral infections such as HIV-1, HIV-2, HTLV-1, hepatitis B and C, West Nile virus, or Cytomegalovirus results in the immediate quarantine and subsequent destruction of the tissue specimen. In some embodiments, the donor's medical records are examined for risk factors for and clinical evidence of hepatitis B, hepatitis C, or HIV infection.

In some embodiments, the fetal support tissue is frozen before pooling. In some embodiments the fetal support tissue is frozen after pooling. In some embodiments, the pooled fetal support tissue is not frozen. In some embodiments, the fetal support tissue that is not frozen is not pooled. If the fetal support tissue is not frozen, but it is first pooled and then it is processed as described below immediately prior to freezing. In some embodiments, if the fetal support tissue is not frozen, but it is processed immediately prior to pooling or freezing as described below.

In some embodiments, substantially all of the blood is removed from the fetal support tissue before pooling (e.g., from any arteries and veins found in the fetal support tissue, and blood that has infiltrated into the tissue). In some embodiments, substantially all of the blood is removed prior to pooling and before the fetal support tissue is frozen. In some embodiments, substantially all of the blood is removed prior to pooling and after the fetal support tissue is frozen. In some embodiments, substantially all of the blood is not removed from the fetal support tissue before pooling (e.g., from any arteries and veins found in the fetal support tissue, or blood that has infiltrated into the tissue). In some embodiments, pooling of fetal support tissue occurs after removing substantially all of the blood from the fetal support tissue. In some embodiments, pooling of fetal support tissue occurs before removing substantially all of the blood from the fetal support tissue. For example, the blood is not removed prior to pooling and before the fetal support tissue is frozen. In some embodiments, substantially all of the blood is not removed prior to pooling or after the fetal support tissue is frozen. In some embodiments, blood is removed from the fetal support tissue before pooling. In some embodiments, blood is not removed from the fetal support tissue before pooling. In some embodiments, blood is removed from the fetal support tissue after pooling. In some embodiments, blood is not removed from the fetal support tissue after pooling. In some embodiments, blood is not removed from the fetal support tissue can be pooled after removal of blood. In some embodiments, blood is removed from the fetal support tissue before the fetal support tissue is pooled but before the fetal support tissue is frozen. In some embodiments, blood is not removed from the fetal support tissue after the fetal support tissue is pooled and before the fetal support tissue is frozen. In some embodiments, the blood is substantially removed prior to pooling the fetal support tissue, after the fetal support tissue has been frozen. In some embodiments, the blood is substantially removed after pooling the fetal support tissue, after the fetal support tissue has been frozen.

In some embodiments, the fetal support tissue is washed with buffer with optionally with agitation to remove excess blood and tissue prior to pooling. In some embodiments, the fetal support tissue is washed with buffer with agitation to remove excess blood and tissue after pooling the fetal support tissue. In some embodiments, the fetal support tissue is pooled first prior to removing excess blood by buffer agitation. In some embodiments, the fetal support tissue is not soaked with buffer with agitation to remove excess blood and tissue prior to pooling. In some embodiments, the fetal support tissue is not soaked with buffer with agitation to remove excess blood and tissue after pooling the fetal support tissue.

In some embodiments, the fetal support tissue is a fetal support tissue graft. In some embodiments, isolated fetal support tissue is used to generate a fetal support tissue graft prior to pooling. In some embodiments, the fetal support tissue is cut into multiple sections (e.g., using a scalpel). The size of the sections depends on the desired use of the fetal support tissue graft derived from the fetal support tissue. In some embodiments, the cut fetal support tissue is optionally washed again with buffer to further remove excess blood and tissue.

The umbilical cord (UC) comprises two arteries (the umbilical arteries) and one vein (the umbilical vein). In some embodiments, the vein and arteries are removed from the UC. In some embodiments, the vein and the arteries are not removed from the UC. In certain instances, the vein and arteries are surrounded (or suspended or buried) within the Wharton's Jelly. In some embodiments, the vein and arteries are removed concurrently with the partial removal of the Wharton's Jelly.

The desired thickness of the fetal support tissue determines how the fetal support tissue is processed. In some embodiments, the desired thickness of the fetal support tissue determines how much of the Wharton's Jelly is removed. In some embodiments, the fetal support tissue is contacted with a buffer to facilitate separation of the Wharton's Jelly and the umbilical cord amniotic membrane. In some embodiments, the Wharton's jelly is removed using peeling, a rotoblator (i.e., a catheter attached to a drill with a diamond coated burr), a liposuction, a liquid under high pressure, a brush (e.g., a mechanized brush rotating under high speed), or a surgical dermatome. In some embodiments, the Wharton's Jelly is not removed from the fetal support tissue. In some embodiments, Wharton's Jelly and the umbilical vein and arteries are not removed. In some embodiments, Wharton's Jelly is not removed, and the umbilical vein and arteries are removed from the fetal support tissue before or after pooling.

In some embodiments, the fetal support tissue comprises isolated umbilical cord amniotic membrane (UCAM). Disclosed herein are processes for generating fetal support tissue while preserving the biological activity of the fetal support tissue, including components of the fetal support tissue, such as HC-HA/PTX3, HA, growth factors, cytokines or other active components as disclosed throughout the specification and claims. In some embodiments, the UCAM is isolated by partially removing some of the Wharton's Jelly and umbilical vessels from the UC, leaving the UCAM. After substantially pure UCAM has been obtained, the UCAM is optionally washed with buffer to remove excess blood and tissue. In some embodiments, the UCAM comprises Wharton's Jelly. In some embodiments, the UCAM comprises Wharton's Jelly and the umbilical vein and arteries. In some embodiments, the UCAM comprises Wharton's Jelly and not the umbilical vein and arteries.

In some embodiments, the fetal support tissue is in any suitable shape (e.g., a square, a circle, a triangle, a rectangle). In some embodiments, the fetal support tissue is generated from a sheet of fetal support tissue. In some embodiments, the sheet is flat. In some embodiments, the sheet is tubular.

In some embodiments, the fetal support tissue is cut into multiple sections (e.g., using a scalpel). In some embodiments, the fetal support tissue is divided into sections that are about 1.0 cm×about 0.25 cm, 0.5 cm, 0.75 cm, 1.0 cm, 2.0 cm, 3.0 cm, 4.0 cm, 5.0 cm, or 6 cm. In some embodiments, the fetal support tissue is divided into sections that are about 2 cm×about 2 cm, 3 cm, 4 cm, 5 cm, or 6 cm. In some embodiments, the fetal support tissue is divided into sections that are about 3 cm×about 3 cm, 4 cm, 5 cm, or 6 cm. In some embodiments, the fetal support tissue is divided into sections that are about 4 cm×about 4 cm, 5 cm, or 6 cm. In some embodiments, the fetal support tissue is divided into sections that are about 5 cm×about 5 cm or 6 cm. In some embodiments, the fetal support tissue is divided into sections that are about 6 cm×about 6 cm. In some embodiments, the fetal support tissue is divided into sections that are about 8 cm×about 1 cm, 2 cm, 3 cm, 4 cm, 5 cm, 6 cm, 7 cm, or 8 cm. In some embodiments, the fetal support tissue is divided into sections that are about 10 cm×about 10 cm. In some embodiments, the fetal support tissue is divided into sections that are about 12 cm×about 10 cm. In some embodiments, the fetal support tissue is divided into sections that are about 15 cm×about 10 cm. In some embodiments, the fetal support tissue is divided into sections that are about 20 cm×about 10 cm. In some embodiments, the fetal support tissue is divided into sections that are about 25 cm×about 10 cm. In some embodiments, the fetal support tissue is divided into sections that are about 30 cm×about 10 cm.

In some embodiments, the fetal support tissue is contacted with buffer under agitation to remove substantially all remaining red blood cells. In some embodiments, the fetal support tissue is contacted with a buffer for 10 minutes, 15 minutes, 20 minutes, 25 minutes, 30 minutes, 40 minutes, 1 hour, 2 hours, 3 hours, 4 hours, 5 hours, 6 hours, 12 hours, 18 hours, 24 hours, or more than 24 hours. In some embodiments, the UC product is contacted with a buffer for 2 days, 3 days, 4 days, 5 days, 6 days, 7 days, 1 week, 2 weeks, 3 weeks, 4 weeks, or more than 4 weeks. The fetal support tissue can be washed 1×, 2×, 3×, 4×, 5× or more. The fetal support tissue may be translucent after watching with no visible traces of blood.

Pooling of Multiple Donors

Provided herein, in certain embodiments, are methods of producing a pooled fetal support tissue product. The process of pooling the fetal support tissue leads to reduced sample to sample variability as would be seen in single donor products and because of high variability in single donor products. It is also difficult to perform, develop a control strategy, and validate the potency assay for single donor products to ensure consistency. However, pooling donor samples was shown to generate increased HA protein content, reduce sample-to-sample variability, improve sample uniformity suggesting pooling of donor fetal support tissue increases consistency and uniformity of the fetal support tissue product or extract generated. In some embodiments, pooling fetal support tissue leads to a reduction in sample-to-sample variability. For example, the resultant standard deviation or percent coefficient of variation obtained after processing single donor samples may be higher than the one obtained from processing of pooled samples. In some embodiments, the variation between single donor sample processes versus pooled donor tissue sample processing may be statistically significant. The variation obtained following processing single donor samples compared to variation following processing pooled tissue samples may be order of magnitude higher. For example, assays performed using pooled donor samples may have at least about a 2-fold, 3-fold, 4-fold, 5-fold, 6-fold, 7-fold or more reduction in variability than for assays conducted using single donor samples. As disclosed herein, pooling fetal tissue samples from a plurality or multiple donors allows scale up of production processes and manufacturing, without sacrificing product potency, consistency, stability, uniformity, or purity, while also allowing efficient assessment and management of quality control processes. In some embodiments, disclosed herein is pooling of fetal support tissue at various stages of processing of fetal support tissue while using parameters as recommended for large-scale processing and commercialization. Pooling of fetal support tissue products occurs at each step of productions in order to significantly eliminate issues that can arise during single donor manufacturing and processing (some of the issues are described above and as known in the art).

In some embodiments, the quantity of HA obtained from pooled fetal support tissues may be higher on average, than the average HA obtained from a collection of single donor samples. For example, the quantity of HA for two or more pooled donor samples may range from at least 5 μg/mL, 10 μg/mL, 15 μg/mL, 20 μg/mL, 30 μg/mL, 40 μg/mL, 50 μg/ml, 60 μg/ml, 70 μg/ml, 80 μg/ml, 90 μg/ml 100 μg/ml, 120 μg/ml 130 μg/ml 140 μg/ml, 150 μg/ml, 160 μg/ml, 170 μg/ml, 180 μg/ml, 190 μg/ml, 200 μg/ml, 210 μg/ml 220 μg/ml, 230 μg/ml, 240 μg/ml, 250 μg/ml, 260 μg/ml, 270 μg/ml, 280 μg/ml, 290 μg/ml, 300 μg/ml, 310 μg/ml, 320 μg/ml, 330 μg/ml, 340 μg/ml, 350 μg/ml, 360 μg/ml, 370 μg/ml, 380 μg/ml, 390 μg/ml, 400 μg/ml, 410 μg/ml, 420 μg/ml, 430 μg/ml, 440 μg/ml, 450 μg/ml, 460 μg/ml, 470 μg/ml, 480 μg/ml, 490 μg/ml to about 500 μg/ml, 510 μg/ml, 520 μg/ml, 530 μg/ml, 540 μg/ml, 550 μg/ml, 560 μg/ml, 570 μg/ml, 580 μg/ml, 590 μg/ml to about 600 μg/ml. In some embodiments, the quantity of protein obtained from two or more pooled donor samples may be from at least 5 μg/mL, 10 μg/mL, 15 μg/mL, 20 μg/mL, 30 μg/mL, 40 μg/mL, 50 μg/ml, 100 μg/ml, 120 μg/ml 130 μg/ml 140 μg/ml, 150 μg/ml, 160 μg/ml, 170 μg/ml, 180 μg/ml, 190 μg/ml, 200 μg/ml, 220 μg/ml, 230 μg/ml, 240 μg/ml, 250 μg/ml, 260 μg/ml, 270 μg/ml, 280 μg/ml, 290 μg/ml, 300 μg/ml, 310 μg/ml, 320 μg/ml, 330 μg/ml, 340 μg/ml, 350 μg/ml, 360 μg/ml, 370 μg/ml, 380 μg/ml, 390 μg/ml, 400 μg/ml, 410 μg/ml, 420 μg/ml, 430 μg/ml, 440 μg/ml, 450 μg/ml, 460 μg/ml, 470 μg/ml, 480 μg/ml, 490 μg/ml to about 500 μg/ml, 510 μg/ml, 520 μg/ml, 530 μg/ml, 540 μg/ml, 550 μg/ml, 560 μg/ml, 570 μg/ml, 580 μg/ml, 590 μg/ml, 600 μg/ml, 650 μg/ml, 700 μg/ml, 750 μg/ml, 800 μg/ml, 850 μg/ml, 900 μg/ml, 950 μg/ml, 1000 μg/ml to about 2000 μg/ml.

In some embodiments, pooling of fetal support tissue increases the amount of protein content of generated from the fetal support tissue. In some embodiments, the quantity of total protein obtained from pooled fetal support tissue may be higher on average, than the average total protein from single donors. In some embodiments, the quantity of total protein obtained from two or more pooled donor samples may be from about 5 μg/mL, 10 μg/mL, 15 μg/mL, 20 μg/mL, 30 μg/mL, 40 μg/mL, 50 μg/ml, 100 μg/ml, 120 μg/ml 130 μg/ml 140 μg/ml, 150 μg/ml, 160 μg/ml, 170 μg/ml, 180 μg/ml, 190 μg/ml, 200 μg/ml, 220 μg/ml, 230 μg/ml, 240 μg/ml, 250 μg/ml, 260 μg/ml, 270 μg/ml, 280 μg/ml, 290 μg/ml, 300 μg/ml, 310 μg/ml, 320 μg/ml, 330 μg/ml, 340 μg/ml, 350 μg/ml, 360 μg/ml, 370 μg/ml, 380 μg/ml, 390 μg/ml, 400 μg/ml, 410 μg/ml, 420 μg/ml, 430 μg/ml, 440 μg/ml, 450 μg/ml, 460 μg/ml, 470 μg/ml, 480 μg/ml, 490 μg/ml to about 500 μg/ml, 510 μg/ml, 520 μg/ml, 530 μg/ml, 540 μg/ml, 550 μg/ml, 560 μg/ml, 570 μg/ml, 580 μg/ml, 590 μg/ml, 600 μg/ml, 650 μg/ml, 700 μg/ml, 750 μg/ml, 800 μg/ml, 850 μg/ml, 900 μg/ml, 950 μg/ml, 1000 μg/ml to over 2000 μg/ml depending on the number of donors samples pooled.

In some instances, the methods of producing the pooled fetal support tissue product comprises any method of producing a fetal support tissue product described herein and a pooling step. In some instances, the pooling step comprises pooling the fetal support tissue derived from multiple donors. In some instances, the pooling step comprises pooling fetal support tissue products derived from multiple donors to produce a pooled composition (e.g., a pooled drug substance). In some instances, the fetal support tissue products are produced by methods described herein, which may comprise the processing including (a) micronizing or cryopulverizing a fetal support tissue to generate a micronized or cryopulverized fetal support tissue; (b) extracting the micronized or cryopulverized fetal support tissue in an excipient to generate an extract; and (c) sterilizing by filtration (liquid extract) or sieving (powder extract) the extract to produce the fetal support tissue product. In some embodiments, the processing of the fetal support tissue (a) may occur before or after pooling the fetal support tissue. In some embodiments, the processing of the fetal support tissue (a) may occur before lyophilization of the fetal support tissue. In some embodiments, the processing of the fetal support tissue (a) may occur after lyophilization of the fetal support tissue. In some embodiments, the lyophilizing of the fetal support tissue may occur before or after the micronizing or cryopulverizing; or may occur before or after the pooling of the donor fetal support tissue. In some instances, a donor lot is an incoming placenta, or any other fetal support tissue material from a single donor. In some instances, the pooling step comprises pooling fetal support tissue products derived from multiple donor lots to produce a pooled composition (e.g., a pooled drug substance). In some instances, the pooling step comprises pooling fetal support tissues (e.g., fetal support tissue products) from (e.g., derived from) at least 15 donors to produce the pooled composition. In some instances, the pooling step comprises pooling fetal support tissues (e.g., fetal support tissue products) from at least 30 donors to produce the pooled composition. In some instances, the pooling step comprises pooling fetal support tissues (e.g., fetal support tissue products) from at least 45 donors to produce the pooled composition. In some instances, the pooling step comprises pooling fetal support tissues (e.g., fetal support tissue products) from at least 10, 15, 20, 25, 30, 35, 40, 45, 50, 55, 60, 65, 70, 75, 80, 85, 90, 95, 100, or more than 100 donors to produce the pooled composition. In some instances, the pooling step comprises pooling fetal support tissues (e.g., fetal support tissue products) from at most 5 donors. In some instances, the pooling step comprises pooling fetal support tissues (e.g., fetal support tissue products) from at most 9, 8, 7, 6, 5, 4, 3, or 2 donors. In some instances, the pooling step comprises pooling fetal support tissue products from 2 or more donors. In some instances, the pooling step comprises pooling multiple batches of a fetal support tissue product to produce a pooled composition. In some embodiments, the pooling step comprises pooling 2, 3, 4, 5, 6, 7, 8, 9, 10, 11, 12, 13, 14, or 15 batches. In some embodiments, no more than three batches are pooled to produce the pooled composition. In some embodiments, a batch is a fetal support tissue composition pooled from fetal support tissue products derived from multiple donors. In some instances, a batch may comprise fetal support tissue products derived from 15 donors. In some embodiments, a batch is pooled from at least 10, 15, 20, 25, 30, 35, 40, 45, 50, 55, 60, 65, 70, 75, 80, 85, 90, 95, 100, or more than 100 donors. In some instances, a batch is pooled from at most 9, 8, 7, 6, 5, 4, 3, or 2 donors. In some instances, pooling comprises pooling three batches, and each batch comprises fetal support tissue from 15 donors. In the steps of the pooling the fetal support tissue described herein, the pooling can be carried out before or after lyophilizing the fetal support tissue wherein the lyophilizing of fetal support tissue occurs before or after the pooling.

Timing of the Pooling Process

Disclosed herein are descriptions of exemplary procedures showing time of processing and pooling of the fetal support tissue material (FIGS. 1A-1B and FIGS. 2A-2C), as processed, and manufactured under commercial production conditions. As indicated in the FIGS. 1A-1B and FIGS. 2A-2C, potential donors are screened; raw material (fetal support tissue) are collected from donors and shipped to the processing facility for receivership and inspection control to determine donor eligibility. In some embodiments, the biological samples are frozen at −80° C. prior to pooling or processing by cleaning, cutting, and soaking in 0.9% saline. In some embodiments, the processing of the biological samples is performed by cleaning, cutting, and soaking in 0.9% saline prior to freezing. Exemplary steps or procedures for processing and pooling of the fetal support tissue including the parameters and in-process controls and the critical quality attributes are as shown in FIGS. 1A-1B and FIGS. 2A-2C. Upon completion of evaluations to assess the critical quality attributes listed, the biological samples (fetal support tissue material) become a regulatory starting material (RSM).

In some embodiments, the regulatory starting material (RSM) or the fetal support tissue material is pooled and processed to generate sheet form or non-sheet form products. In some embodiments, the regulatory starting material or the fetal support tissue material is processed into sheet form product and non-sheet forms prior to pooling. In some embodiments, the pooled fetal support tissue is processed by micronization. In some embodiments, the micronization is used to generate gel products. In some embodiments, pooled fetal support tissue that is micronized into a dry powder and liquified can be further filtered before or after terminal sterilization. In some embodiments, the micronized fetal support tissue that is in liquid form can be centrifuged before or after terminal sterilization e.g., using gamma sterilization or a combination thereof. In some embodiments, filtration controls for sterilization of the liquid form of the fetal support tissue extract wherein a filter pore size of equal to or about less than 0.2 um is utilized. In some embodiments, the micronization of the fetal support tissue resulting in a dry powder form is not liquified but is sieved and either used immediately or frozen at −80° C. In some embodiments, the micronization and sieving of the fetal support tissue extract controls for particle size. In some embodiments, terminal sterilization of the dry powder extract occurs through the process of for example, gamma sterilization. In some embodiments, the fetal support tissue may be cryopulverized resulting in fine powder extract, or liquified. In some embodiments, the cryopulverized fetal support tissue that is a powder extract can further be sieved resulting in different sized particles. In some embodiments, the cryopulverized fetal support tissue that is a fine powder can be terminally sterilized e.g., with the use of gamma sterilization. In some embodiments, the fetal support tissue extract may be liquified, and it can be filtered, centrifuged, a combination thereof to either sterilize it (filer pore size equal to or about less than 0.2 um) or to control for particle size. In some embodiments, the fetal support tissue can undergo decellularization, devitalization, micronization, cryopulverization or a combination thereof. In some embodiments, the micronized, cryopulverized or decellularized, devitalized fetal support tissue extract can further be filtered, centrifuged (liquid form), or sieved (dry powder) variously (or a combination thereof), resulting into fetal support tissue products of varying particle sizes. In some embodiments, fetal support tissue may not be pooled prior to being processed (by micronization, cryopulverization, decellularization, devitalization, centrifugation, sterilization e.g., gamma sterilization, sieving filtration or a combination thereof) to result into fetal support tissue products of varying particle sizes.

In some embodiments, fetal support tissue may be lyophilized and processed by micronization, cryopulverization, decellularization, or devitalization, or a combination thereof prior to pooling. For examples, the fetal support tissue may be lyophilized to being micronized, cryopulverized, decellularized or devitalized, or a combination thereof further undergo sieving (dry powder) or centrifugation, filtration (liquid form) terminal sterilization e.g., gamma irradiation, or a combination thereof, to result into fetal support tissue products of varying particle sizes prior to pooling. In some embodiments, the fetal support tissue may be lyophilized and pooled prior to being processed by micronization, cryopulverization, decellularization, devitalization, or a combination thereof. In some embodiments, the fetal support tissue may be lyophilized and pooled prior to being micronized, cryopulverized, decellularized, devitalized, or a combination thereof, can undergo sieving (dry powder) and various terminal sterilization procedures or if liquid form can be centrifuged, filtered, a combination thereof, to result into filter-sterilized fetal support tissue products or fetal support tissue products of varying particle sizes.

In some embodiments, pooled fetal support tissue may be lyophilized prior to being processed by micronization, cryopulverization, decellularization, devitalization, or a combination thereof and may be lyophilized prior to sieving and/or sterilizing of dry powder fetal support tissue extract or centrifugation, sterilization, filtration of liquid form fetal support tissue extract/product, or a combination thereof, to result into fetal support tissue products of varying particle sizes. In some embodiments, pooled fetal support tissue may not be lyophilized prior to being processed by micronization, cryopulverization, decellularization, devitalization, or a combination thereof. In some embodiments, fetal support tissue may not be lyophilized prior to sieving and/or sterilizing of dry powder fetal support tissue extract, or centrifugation, filtration of liquid form fetal support tissue extract/product, or a combination thereof, to result into fetal support tissue products of varying particle sizes.

In some embodiments, the particle sizes of processed pooled fetal support tissue product can be less than 5 μm. In some embodiments, the particle sizes of pooled processed fetal support tissue product can be less than about 5 μm. In some embodiments, the particle size of the pooled processed fetal support tissue can be about 5 to about 10 μm. In some embodiments, the particle size of the pooled processed fetal support tissue product can be less than 1 μm, about less than 1 μm, about less than 10 to about 15 μm. In some embodiments, the pooled fetal support tissue has a particle size of any range as disclosed in the specification and claims of the disclosure, and any combination thereof.

In some embodiments, the particle size of the fetal support tissue product prior to pooling can be less than 5 μm. In some embodiments, the particle sizes of processed fetal support tissue product can be less than about 5 μm prior to pooling. In some embodiments, the particle size of processed fetal support tissue can be about 5 to about 10 μm prior to pooling. In some embodiments, the particle size of the processed fetal support tissue product can be less than 1 μm, about less than 1 μm, about less than 10 to about 15 μm prior to pooling. In some embodiments, the fetal support tissue has a particle size of any range as disclosed in the specification and claims of the disclosure, and any combination thereof, prior to pooling. In some embodiments, the fetal support tissue has a particle size of any range as disclosed in the specification and claims of the disclosure, and any combination thereof, after pooling the fetal support tissue. In some embodiments, the particle size of pooled fetal support tissue product can be less than 5 μm. In some embodiments, the particle sizes of pooled processed fetal support tissue product can be less than about 5 μm. In some embodiments, the particle size of the pooled processed fetal support tissue can be about 5 to about 10 μm. In some embodiments, the particle size of the pooled processed fetal support tissue product can be less than 1 μm, about less than 1 μm, about less than 10 to about 15 μm. In some embodiments, the pooled fetal support tissue has a particle size of any range as disclosed in the specification and claims of the disclosure, and any combination thereof.

In some instances, the pooling step comprises a sieving step. In some embodiments, the sieving step controls the maximum particle size of a pooled composition (e.g., a bulk drug substance). In some embodiments, the sieve has an average pore size of about 0.1-0.2 μm or less, 0.2-0.3 μm or less, 0.3-0.4 μm or less, 0.4-0.5 μm or less, 0.5-0.6 μm or less, 0.6-0.7 μm or less, 0.7-0.8 μm or less, 0.8-0.9 μm or less, 0.9-1 μm or less, 1-2 μm or less, 2-3 μm or less, 3-4 μm or less, 4-5 μm or less, 5-10 μm or less, 10-20 μm or less, 20-30 μm or less, 30-40 μm or less, 40-50 μm or less, 50-100 μm or less, 100-150 μm or less, 150-200 μm or less, 200-250 μm or less, or 250-300 μm or less. In some instances, the pooling step produces a composition with a high yield of HC-HA/PTX3, HA, and other proteins of interest, improved stability, reduced variability, improved potency, uniformity, consistency, or a combination thereof, as compared to a composition produced by the same method, but without being subject to a pooling step.

In some embodiments, the particle size is strictly adhered to when the fetal support tissue extract is administered via inhalation, or intravenously as disclosed herein. Disclosed herein are processes for generating fetal support tissue while preserving the biological activity of the fetal support tissue, including components of the fetal support tissue, such as HC-HA/PTX3, HA, growth factors, cytokines or other active components as disclosed throughout the specification and claims.

Preparation of Pooled Compositions

In some aspect, a pooled composition disclosed herein may be prepared from pooling fetal support tissue from multiple donors and compared to a non-pooled composition (termed FLO). Prior to pooling, micronized drug substance of each of the individual pools may be analyzed for hyaluronic acid content, total protein, and ODI-TRAP. Exemplary results from such a procedure in which results are combined to give a weighted average of each result prior to pooling can be seen in FIGS. 1A-1B, in which the pooling process from multiple donors is depicted. In some embodiments, the stability study may be conducted with a composition manufactured through the pooling of donor fetal support tissue samples. As disclosed herein, the results from this procedure met acceptance criteria for T=0, 1, 3 and 6 months. The data range for each of the CQA are shown in Table 1 and Table 2.

Extraction and Centrifugation

In some embodiments, the extraction step yield either dry powder or a liquid form of the pooled fetal support tissue product. In some embodiments, the liquid form is centrifuged and purified to control for particle sizes, for example, to control the particle size of the fetal support tissue that contains HC-HA/PTX3, HA, growth factors, cytokines, and other bioactive components. In some embodiments, the aforementioned extract, liquid or powder, of the fetal support tissue may be used to purify the nHC-HA/PTX3 complex by centrifugation (e.g., ultracentrifugation, gradient centrifugation), chromatography (e.g., ion exchange, affinity, size exclusion, and hydroxyapatite chromatography), gel filtration, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference).

In some embodiments, nHC-HA/PTX3 is isolated from an extract of pooled fetal support tissue. In some embodiments, the extract is prepared from an amniotic membrane extract. In some embodiments, the extract is prepared from an umbilical cord extract. In some embodiments, the umbilical cord extract comprises umbilical cord stroma and/or Wharton's jelly or a combination thereof. In some embodiments, the nHC-HA/PTX3 complex is contained in an extract that is prepared by ultracentrifugation. In some embodiments, the nHC-HA/PTX3 complex is contained in an extract that is prepared by ultracentrifugation using a CsCl/4-6M guanidine HCl gradient. In some embodiments, the extract is prepared by at least 2 rounds of ultracentrifugation. In some embodiments, the extract is prepared by more than 2 rounds of ultracentrifugation (i.e., nHC-HA/PTX3 $2^{nd}$). In some embodiments, the extract is prepared by at least 4 rounds of ultracentrifugation (i.e., nHC-HA/PTX3 $4^{th}$). In some embodiments, the nHC-HA/PTX3 complex comprises a small leucine-rich proteoglycan. In some embodiments, the nHC-HA/PTX3 complex comprises HC1, HA, PTX3 and/or a small leucine-rich proteoglycan.

In some embodiments, extraction is performed on the fetal support tissue. In some embodiments, extraction comprises separating proteins of interest from other components of the fetal support tissue. In some embodiments, extraction is performed on the cryopulverized fetal support tissue. In some embodiments, extraction comprises separating proteins of interest from other components of the cryopulverized fetal support tissue. In some embodiments, such extraction with or without centrifugation aims to preserve or retain HA, which is also present in nHC-HA/PTX3.

In some embodiments, the extract is prepared by extraction in an excipient. In some embodiments, the excipient is saline, water, structured water, water for injection (WFI), or a combination thereof. In some embodiments, the excipient is WFI. In some embodiments, use of WFI as an excipient produces a higher recovery rate of HA and total proteins as compared to saline, or structured water. In some embodiments, extraction in saline or WFI extracts a majority of nHC-HA/PTX3.

In some embodiments, the extraction is performed for about 0 to 1 hours, about 1 to 2 hours, about 2 to 3 hours, about 3 to 4 hours, about 4 to 5 hours, about 5 to 6 hours, about 6 to 12 hours, about 12 hours to 24 hours, about 24 hours to 48 hours or about 48 hours to 72 hours. In some embodiments, the extraction is performed for about 1 hour. In some embodiments, the extraction is performed in WFI for about 0 to 1 hours, about 1 to 2 hours, about 2 to 3 hours, about 3 to 4 hours, about 4 to 5 hours, about 5 to 6 hours, about 6 to 12 hours, about 12 hours to 24 hours, about 24 hours to 48 hours or about 48 hours to 72 hours. In some embodiments, the extraction is performed in WFI for about 1 hour. In some embodiments, the extraction is performed in saline for about 0 to 1 hours, about 1 to 2 hours, about 2 to 3 hours, about 3 to 4 hours, about 4 to 5 hours, about 5 to 6 hours, about 6 to 12 hours, about 12 hours to 24 hours, about 24 hours to 48 hours or about 48 hours to 72 hours. In some embodiments, the extraction is performed in saline for about 1 hour.

In some embodiments the extraction is performed at a temperature of about 4° C. In some embodiments, the extraction is performed at a temperature of about 3° C., 4° C., 5° C., or 6° C. In some embodiments, the extraction is performed in WFI at a temperature of about 3° C., 4° C., 5° C., or 6° C. In some embodiments the extraction is performed in WFI at a temperature of about 4° C. In some embodiments, the extraction is performed in WFI for about 1 hour at a temperature of about 4° C. In some embodiments, the extraction is performed in WFI for about for about 0 to 1 hours, about 1 to 2 hours, about 2 to 3 hours, about 3 to 4 hours, about 4 to 5 hours, about 5 to 6 hours, about 6 to 12 hours, about 12 hours to 24 hours, about 24 hours to 48 hours or about 48 hours to 72 hours, at a temperature of about 4° C. In some embodiments, the extraction is performed in saline at a temperature of about 3° C., 4° C., 5° C., or 6° C. In some embodiments the extraction is performed in saline at a temperature of about 4° C. In some embodiments, the extraction is performed in saline for about for about 0 to 1 hours, about 1 to 2 hours, about 2 to 3 hours, about 3 to 4 hours, about 4 to 5 hours, about 5 to 6 hours, about 6 to 12 hours, about 12 hours to 24 hours, about 24 hours to 48 hours or about 48 hours to 72 hours, at a temperature of about 4° C. In some embodiments, the extraction is performed in saline for about 1 hour at a temperature of about 4° C.

In some embodiments, the ratio of fetal support tissue to extraction excipient is about 1:6, 1:5, 1:4, 1:3, 1:2, 1:1, 1:0.75, 1:0.5, or 1:0.25 (weight:volume). In some embodiments, the ratio of fetal support tissue to extraction excipient is about 6:1, 5:1, 4:1, 3:1, 2:1, 1:1, 0.75:1, 0.5:1, or 0.25:1 (weight:volume). In some embodiments, the ratio of fetal support tissue to extraction excipient is about 1:4. In some embodiments, the extraction is performed in WFI or saline. In some embodiment, the extraction is performed in WFI. In some embodiments, the extraction is performed for about 0 to 1 hours, about 1 to 2 hours, about 2 to 3 hours, about 3 to 4 hours, about 4 to 5 hours, about 5 to 6 hours, about 6 to 12 hours, about 12 hours to 24 hours, about 24 hours to 48 hours or about 48 hours to 72 hours. In some embodiments, the extraction is performed for about 1 hour. In some embodiments, the extraction is performed for at a temperature of about 3° C., 4° C., 5° C., or 6° C. In some embodiments, the extraction is performed for at a temperature of about 4° C. In some embodiments, the extraction is performed in WFI for about 1 hour at a temperature of about 4° C. at a ratio of fetal support tissue to excipient of about 1:4. In some embodiments, the extraction is performed in saline for about 1 hour at a temperature of about 4° C. at a ratio of fetal support tissue to excipient of about 1:4.

In some embodiments, the extraction is performed using a tube rotator. In some embodiments, the tube rotator rotates at a range of speed from about 5-10 rpm, 10-20 rpm, 20-30 rpm, 30-40 rpm, or 40-50 rpm. In some embodiments, the tube rotator rotates at a speed of about 20 rpm. In some embodiments, the tube rotator rotates for about 0 to 1 hours, about 1 to 2 hours, about 2 to 3 hours, about 3 to 4 hours, about 4 to 5 hours, about 5 to 6 hours, about 6 to 12 hours, about 12 hours to 24 hours, about 24 hours to 48 hours or about 48 hours to 72 hours. In some embodiments, the tube rotator rotates for about 1 hour. In some embodiments, the tube rotator rotates at a temperature of about 3° C., 4° C., 5° C., or 6° C. In some embodiments, the tube rotator rotates at a temperature of about 4° C. In some embodiments, the excipient used is saline or WFI. In some embodiments, the excipient used is WFI. In some embodiments, the ratio of fetal support tissue to extraction excipient is about 1:6, 1:5, 1:4, 1:3, 1:2, 1:1, 1:0.75, 1:0.5, or 1:0.25 (weight:volume). In some embodiments, the ratio of fetal support tissue to extraction excipient is about 1:4. In some embodiments, the ratio of fetal support tissue to extraction excipient is about 6:1, 5:1, 4:1, 3:1, 2:1, 1:1, 0.75:1, 0.5:1, or 0.25:1 (weight: volume). In some embodiments, the extraction is performed in WFI for about 1 hour at a temperature of about 4° C. using a tube rotator at a speed of about 20 rpm. In some embodiments, the extraction is performed in saline for about 1 hour at a temperature of about 4° C. using a tube rotator at a speed of about 20 rpm.

In some embodiments, centrifugation is performed on the extract produced by the extraction step. In some embodiments, extract is centrifuged for about 5 to 10 minutes, about 10 to 15 minutes, about 15 to 20 minutes, about 20 to 30 minutes, about 30 minutes to 1 hour, or about 1 to 2 hours. In some embodiments, the extract is centrifuged for about 30 minutes. In some embodiments, the extract is centrifuged at a speed of about 3,200 rcf to 10,000 rcf, about 10,000 to 14,000 rcf, about 14,000 to 32,000 rcf, or about 32,000 to about 48,000 rcf. In some embodiments, the extract is centrifuged at a speed of about 14,000 rcf or higher. In some embodiments, the extract is centrifuged at a speed of about 14,000 rcf. In some embodiments, the extract is centrifuged at a speed of about 14,000 rcf for about 30 minutes. In some embodiments, the centrifugation does not affect or minimally effects the content of the protein of interest in the extract.

In some embodiments the extraction produces an extract comprising hyaluronan, which is present in nHC-HA/PTX3. In some embodiments, the extraction in saline or WFI results in less damage to the nHC-HA/PTX3 complex than extraction using a different excipient, for example structured water. In some embodiments, the extraction in saline or WFI results in a greater yield of HA or nHC-HA/PTX3 complex than extraction using a different excipient, for example structured water. In some embodiments, the extract contains greater than about 900 μg/g HA to extract (wet). In some embodiments, the extract contains greater than about 1000 μg/g HA to extract (wet). In some embodiments, the extract contains greater than about 1100 μg/g HA to extract (wet). In some embodiments, the extract contains greater than about 1200 μg/g HA to extract (wet). Disclosed herein are processes for generating fetal support tissue while preserving the biological activity of the fetal support tissue, including components of the fetal support tissue, such as HC-HA/PTX3, HA, growth factors, cytokines or other active components as disclosed throughout the specification and claims.

Dilution

Described herein, in certain embodiments, are methods for processing a fetal support tissue, wherein the methods comprise a dilution step to yield different doses of the fetal support tissue product. In some embodiments, the dilution step is performed on the fetal support tissue after it has been subject to the extraction and centrifugation steps. In some embodiments, the dilution step is performed on the fetal support tissue after it has been subjected to the extraction and centrifugation step and before it is sterile filtered. In some embodiments, diluting the extract (e.g., reducing the concentration of proteins of interest in the extract) is achieved by mixing the extract with an excipient. In some embodiments, the excipient is saline, water, structured water, water for injection (WFI), or a combination thereof.

In some embodiments, the excipient is WFI. In some embodiments, the extract is mixed with the excipient at a dilution factor of about 1 to 1.5, about 1.5 to 2, about 2 to 2.5, about 2.5 to 3, about 3-3.5 about 3.5 to 4, about 4 to 5, about 5 to 6, about 6 to 7, about 7 to 8, about 8 to 9, or about 9 to 10. In some embodiments, the dilution factor is greater than 5. In some embodiments, the dilution factor is greater than 10. In some embodiments, the dilution factor is about 2. In some embodiments, the excipient is WFI, and the dilution factor is 2. In some embodiments, the excipient is saline, and the dilution factor is 2. In some embodiments, methods described herein further comprise mixing the extract and the excipient for about 10 to 30 minutes, about 30 minutes to 1 hour, or for about 1 hour to 2 hours. In some embodiments the extract and excipient are mixed for about 30 minutes. In some embodiments, the extract and excipient are mixed at a speed of about 5-10 rpm, 10-20 rpm, 20-30 rpm, 30-40 rpm, or 40-50 rpm. In some embodiments, the extract and excipient are mixed at a speed of about 20 rpm. In some embodiments, the extract and excipient are mixed at a speed of about 20 rpm for about 1 hour. In some embodiments, the extract and excipient are mixed at a temperature of about 4° C. In some embodiments, the extract and excipient are mixed at a speed of about 20 rpm for about 1 hour at about 4° C. In some embodiments, the extract is diluted prior to a filtration step. In some embodiments, the extract is diluted after a filtration step.

In some embodiments, dilution increases the speed of filtration or the recovery rate of one or more proteins of interest after filtration, the recovery rate of one or more proteins of interest, or the potency of the extract (e.g., as measured by an ODI-TRAP assay, an M2 assay, an NO assay and/or a WST-1 assay), or a combination thereof, as compared to an undiluted extract comprising the same fetal support tissue and excipient. In some embodiments, diluted fetal support tissue comprises from about 1 μg/ml-to about 150 μg/ml of Hyaluronan (HA). In some embodiments, diluted fetal support tissue comprises from about 1 μg/ml-to about 90 μg/ml of Hyaluronan (HA). In some embodiments, diluted fetal support tissue comprises from about 90 μg/ml-to about 150 μg/ml of Hyaluronan (HA).

Figure 3:
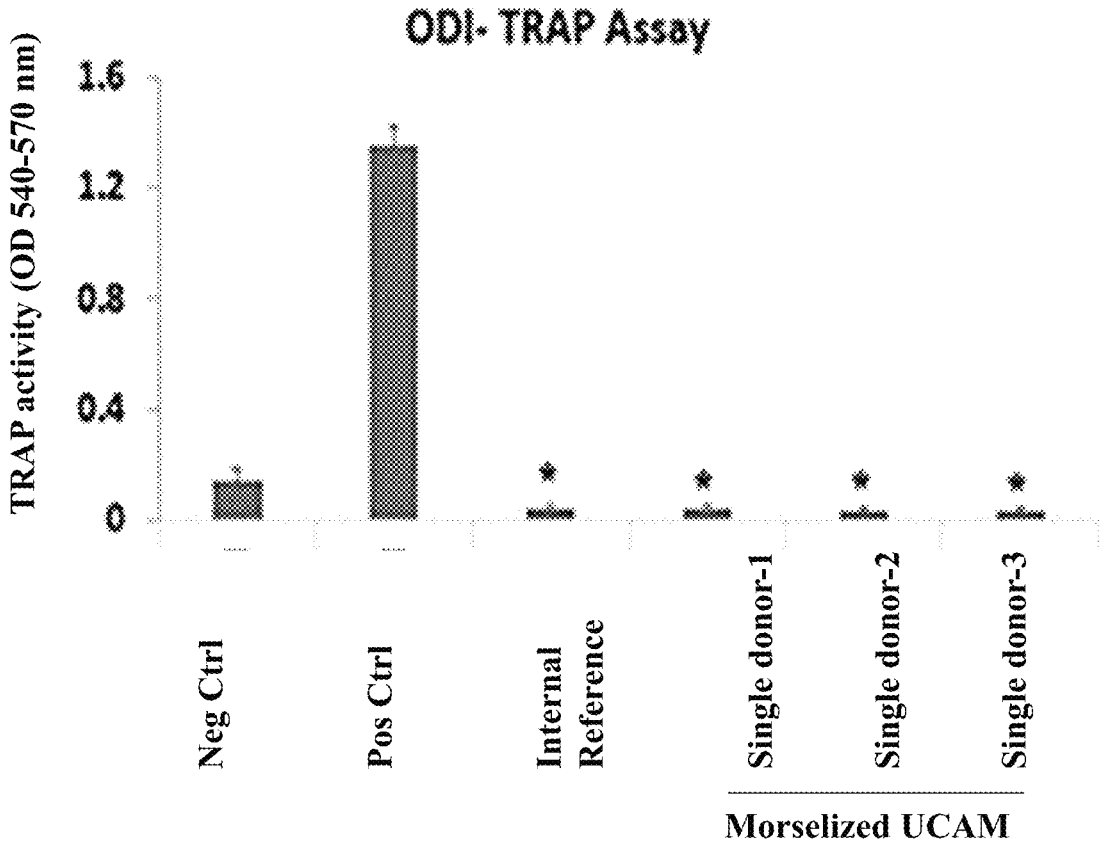
FIG. 3 shows an example of a cell morphology analysis and ODI-TRAP assay of fetal support tissue products.
Figure 4:
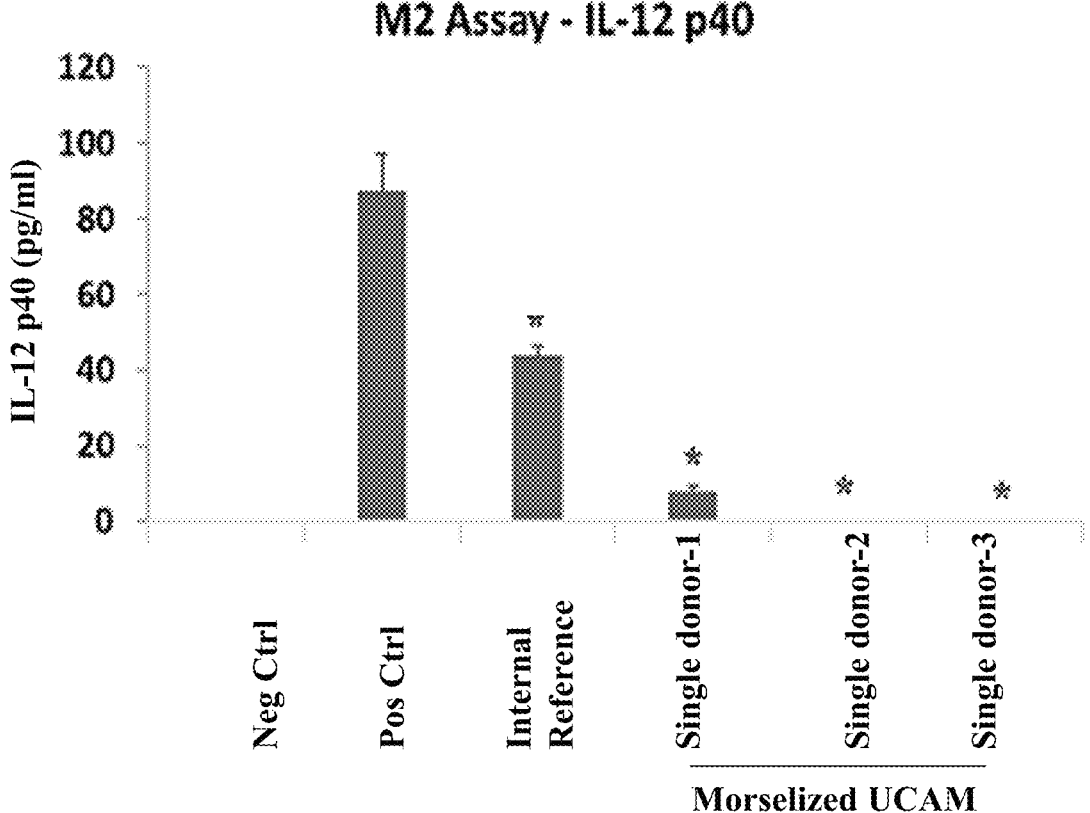
FIG. 4 shows an example of a cell morphology analysis and M2 IL-12 assay of fetal support tissue products.
Figure 5:
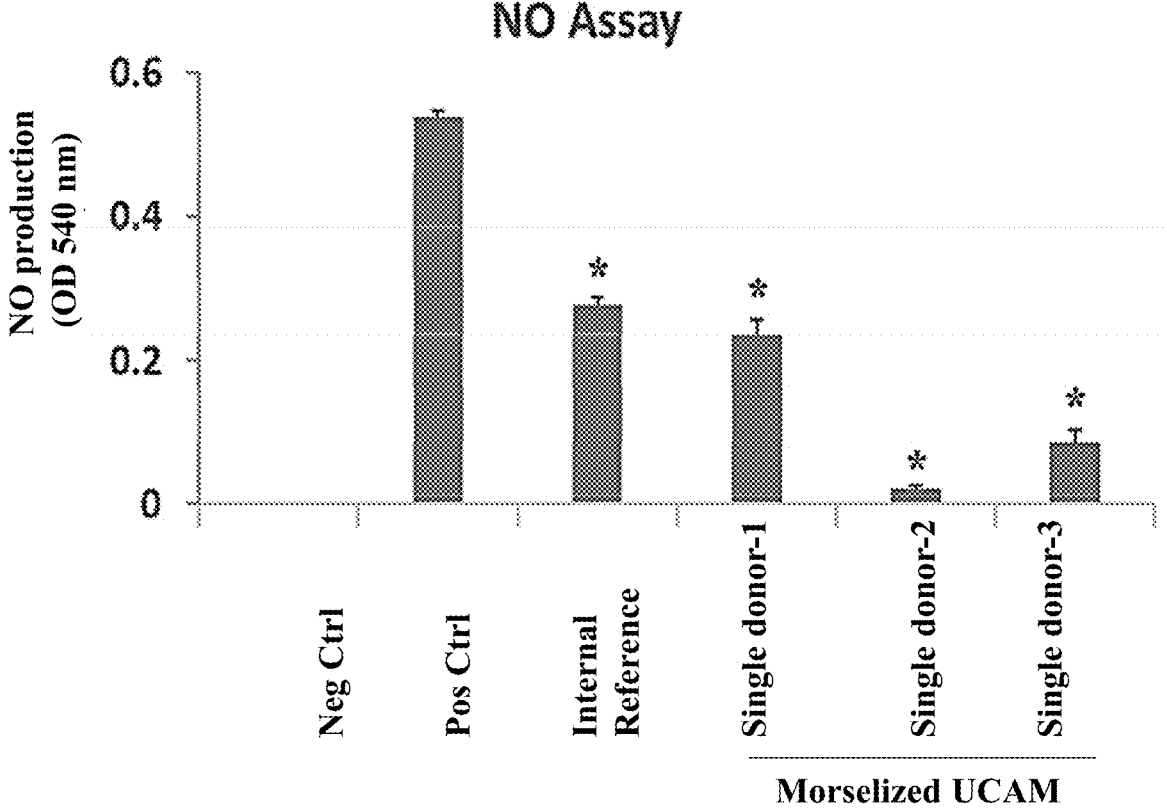
FIG. 5 shows an example of a cell morphology analysis and an exemplary M2 NO assay of fetal support tissue products.

Validation Assays: In some embodiments, the methods disclosed herein are used in assays to validate a pooled fetal support tissue product. In some embodiments, the assays to validate the pooled fetal support tissue products, extracts, compositions, or a combination thereof, is an assay or method comprising conducting a validation assay on the pooled fetal support tissue, wherein the validation assay determines an amount of native HC-HA/PTX3 complex and/or its activity. In some embodiments, assays disclosed herein validate the range of concentrations, potency, the identity, the preservation, the presence of nHC-HA/PTX3, proteoglycans, cytokines, growth factors and other biological components in fetal support tissue. In some embodiments, are methods, assays for determining degradation of nHC-HA/PTX3 complex, or any other components of the pooled fetal support tissues. In some embodiments, methods to monitor degradation of the nHC-HA/PTX3 complex or any other factors in fetal support tissues, can be performed for example, when the degradation assay monitors degradation of nHC-HA/PTX3, or degradation of any component of fetal support tissue. Such validation assays as described herein including ODI-TRAP (e.g., FIG. 3), NO production/release (e.g., FIG. 5), M2-IL-12 release (e.g., FIG. 4) or total HA content (e.g., FIG. 7), can be used to monitor nHC-HA/PTX3 presence, potency and/or activity at any stage of processing, including but not limited to, before pooling, after pooling, before lyophilization, after lyophilization, before micronization, after micronization or after storage of a finished product to monitor stability or potency.

Assay Matrix: WST-1 Assay: Potency of HC-HA/PTX3 Complex and HC-HA/PTX3 Extracts Against Cancer In some embodiments, the composition exhibits a statistically significant inhibition of TRAP activity compared to a positive control in the ODI-TRAP assay when an HA content of the composition is at least 200 μg/ml. In some embodiments, the composition exhibits a statistically significant inhibition of TRAP activity compared to a positive control in the ODI-TRAP assay when an HA content of the composition is at least 250 μg/ml. In some embodiments, the composition exhibits a statistically significant inhibition of TRAP activity compared to a positive control in the ODI-TRAP assay when an HA content of the composition is at least 300 μg/ml. In some embodiments, the composition exhibits a statistically significant inhibition of TRAP activity compared to a positive control in the ODI-TRAP assay when an HA content of the composition is at least 400 μg/ml. In some embodiments, the composition exhibits a statistically significant inhibition of TRAP activity compared to a positive control in the ODI-TRAP assay when an HA content of the composition is at least 500 μg/ml. In some embodiments, the composition exhibits a statistically significant inhibition of TRAP activity compared to a positive control in the ODI-TRAP assay when an HA content of the composition is at least 600 μg/ml μg/ml. In some embodiments, the composition exhibits a statistically significant inhibition of TRAP activity compared to a positive control in the ODI-TRAP assay when an HA content of the composition is at least 700 μg/ml. In some embodiments, the composition exhibits a statistically significant inhibition of TRAP activity compared to a positive control in the ODI-TRAP assay when an HA content of the composition is at least 800 μg/ml. In some embodiments, the composition exhibits a statistically significant inhibition of TRAP activity compared to a positive control in the ODI-TRAP assay when an HA content of the composition is at least 900 μg/ml. In some embodiments, the composition exhibits a statistically significant inhibition of TRAP activity compared to a positive control in the ODI-TRAP assay when an HA content of the composition is at least 1,000 μg/ml.

In some embodiments, disclosed herein is a composition wherein an HA content of at least 50 μg/ml, 60 μg/ml, 70 μg/ml, 80 μg/ml, 90 μg/ml, 100 μg/ml, 150 μg/ml, 200 μg/ml, 250 μg/ml, 300 μg/ml, 350 μg/ml, 400 μg/ml or at least 500 μg/ml significant inhibit TRAP activity, wherein the inhibition is at least 70% inhibition of TRAP activity. In some embodiments, disclosed herein is a composition wherein the significant inhibition of TRAP activity is at least 80% inhibition of TRAP activity. In some embodiments, disclosed herein is a composition wherein the significant inhibition of TRAP activity is at least 85% inhibition of TRAP activity. In some embodiments, the HA content of the composition is at least 200 μg/ml. In some embodiments, the HA content of the composition is at least 250 μg/ml. In some embodiments, the HA content of the composition is at least 300 μg/ml. In some embodiments, the HA content of the composition is at least 350 μg/ml. In some embodiments, the HA content of the composition is about 300 μg/ml.

In some embodiments, the therapeutic potency is determined by the WST-1 assay. For example, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded between 1 µg/ml-1,500 µg/ml. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 1 µg/ml. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 10 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 50 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 100 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 200 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 250 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 300 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 350 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 400 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 500 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 550 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 600 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 650 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 700 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 750 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 800 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 850 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 900 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 950 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at least 1,000 µg/ml or less. In some embodiments, the pooled fetal support tissue extract comprising HC-HA/PTX3 or HC-HA/PTX3-containing tissue extract, e.g., umbilical cord extract but not HA, can inhibit cancer or inhibit tumor metabolic acidity (p<0.05) compared to positive control when the extract is loaded at about 90 µg/ml, 100 µg/ml, 200 µg/ml, 300 µg/ml, 500 µg/ml or more than 1,500 µg/ml.

Identity and potency of fetal support tissue composition using ODI-TRAP assay matrix. In an aspect, described herein, the pooled composition of fetal support tissue comprises a potency as determined by ODI-TRAP. The cell-based ODI-TRAP assay is a quantitative biological test that measures the specific activity of pooled fetal support tissue based on its activity in inhibiting TRAP activity. Inhibitory activity can be evaluated in a comparative assay to evaluate and detect inhibition by ODI-TRAP in general (e.g., FIG. 6B), or to set up assays to perform comparative TRAP inhibition detection among single donor sample lots (e.g., FLO; FIG. 10A) versus inhibition detected in pooled sample lots (FIG. 10B). In certain embodiments, the pooled fetal support tissue possesses adequate potency if a statistically significant difference in a TRAP assay compared to positive control is exhibited for fetal support tissue with an HA content of at least 5 µg/ml, 10 µg/ml, 15 µg/ml, 20 µg/ml, 30 µg/ml, 40 µg/ml, 50 µg/ml, 100 µg/ml, 150 µg/ml, 200 µg/ml, 250 µg/ml, 300 µg/ml, 350 µg/ml, 400 µg/ml, 450 µg/ml, 500 µg/ml, 600 µg/ml, 700 µg/ml, 800 µg/ml, 900 µg/ml, 1,000 µg/ml. In certain embodiments, the pooled fetal support tissue possesses adequate potency if a statistically significant difference compared to positive control is exhibited for fetal support tissue with an HA content of at least 5 µg/ml. In certain embodiments, the pooled fetal support tissue possesses adequate potency if a statistically significant difference compared to positive control is exhibited for fetal support tissue with an HA content of at least 10 µg/ml. In certain embodiments, the pooled fetal support tissue possesses adequate potency if a statistically significant difference compared to positive control is exhibited for fetal support tissue with an HA content of at least 15 µg/ml. In certain embodiments, the pooled fetal support tissue possesses adequate potency if a statistically significant difference compared to positive control is exhibited for fetal support tissue with an HA content of at least 20 µg/ml. In certain embodiments, the pooled fetal support tissue possesses adequate potency if a statistically significant difference compared to positive control is exhibited for fetal support tissue with an HA content of at least 30 µg/ml. In certain embodiments, the pooled fetal support tissue possesses adequate potency if a statistically significant difference compared to positive control is exhibited for fetal support tissue with an HA content of at least 40 µg/ml. In certain embodiments, the pooled fetal support tissue possesses adequate potency if a statistically significant difference compared to positive control is exhibited for fetal support tissue with an HA content of at least 50 µg/ml. In certain embodiments, the pooled fetal support tissue possesses adequate potency if a statistically significant difference compared to positive control is exhibited for fetal support tissue with an HA content of at least 100 µg/ml. In certain embodiments, the pooled fetal support tissue possesses adequate potency if a statistically significant difference compared to positive control is exhibited for fetal support tissue with an HA content of at least 150 µg/ml. In certain embodiments, the pooled fetal support tissue possesses adequate potency if a statistically significant difference compared to positive control is exhibited for fetal support tissue with an HA content of at least 200 µg/ml. In certain embodiments, the pooled fetal support tissue possesses adequate potency if a statistically significant difference compared to positive control is exhibited for fetal support tissue with an HA content of at least 250 µg/ml. In certain embodiments, the pooled fetal support tissue possesses adequate potency if a statistically significant difference compared to positive control is exhibited for fetal support tissue with an HA content of at least 300 µg/ml. In certain embodiments, the pooled fetal support tissue possesses adequate potency if a statistically significant difference compared to positive control is exhibited for fetal support tissue with an HA content of at least 350 µg/ml. In certain embodiments, the pooled fetal support tissue possesses adequate potency if a statistically significant difference compared to positive control is exhibited for fetal support tissue with an HA content of at least 400 µg/ml. In certain embodiments, the pooled fetal support tissue possesses adequate potency if a statistically significant difference compared to positive control is exhibited for fetal support tissue with an HA content of at least 500 µg/ml. In certain embodiments, the pooled fetal support tissue possesses adequate potency if a statistically significant difference compared to positive control is exhibited for fetal support tissue with an HA content of at least 600 µg/ml. In certain embodiments, the pooled fetal support tissue possesses adequate potency if a statistically significant difference compared to positive control is exhibited for fetal support tissue with an HA content of at least 700 µg/ml. In certain embodiments, the pooled fetal support tissue possesses adequate potency if a statistically significant difference compared to positive control is exhibited for fetal support tissue with an HA content of at least 800 µg/ml. In certain embodiments, the pooled fetal support tissue possesses adequate potency if a statistically significant difference compared to positive control is exhibited for fetal support tissue with an HA content of at least 900 µg/ml. In certain embodiments, the pooled fetal support tissue possesses adequate potency if a statistically significant difference compared to positive control is exhibited for fetal support tissue with an HA content of at least 1,000 µg/ml.

In some embodiments, the pooled fetal support tissue demonstrates adequate TRAP potency if at least about 100 µg/ml of HA exerts at least 60%, 65%, 70%, 75%, 80%, 85%, 90%, 95%, 97%, 98%, 99% TRAP inhibitory effect. In some embodiments, the pooled fetal support tissue demonstrates adequate TRAP potency if at least about 100 µg/ml of HA exerted at least 60%, TRAP inhibitory effect. In some embodiments, the pooled fetal support tissue demonstrates adequate TRAP potency if at least about 100 µg/ml of HA exerted at least 65% TRAP inhibitory effect. In some embodiments, the pooled fetal support tissue demonstrates adequate TRAP potency if at least about 100 µg/ml of HA exerted at least 70% TRAP inhibitory effect. In some embodiments, the pooled fetal support tissue demonstrates adequate TRAP potency if at least about 100 µg/ml of HA exerted at least 75% TRAP inhibitory effect. In some embodiments, the pooled fetal support tissue demonstrates adequate TRAP potency if at least about 100 µg/ml of HA exerted at least 80% TRAP inhibitory effect. In some embodiments, the pooled fetal support tissue demonstrates adequate TRAP potency if at least about 100 µg/ml of HA exerted at least 85% TRAP inhibitory effect. In some embodiments, the pooled fetal support tissue demonstrates adequate TRAP potency if at least about 100 µg/ml of HA exerted at least 90% TRAP inhibitory effect. In some embodiments, the pooled fetal support tissue demonstrates adequate TRAP potency if at least about 100 µg/ml of HA exerted at least 95% TRAP inhibitory effect. In some embodiments, the pooled fetal support tissue demonstrates adequate TRAP potency if at least about 100 µg/ml of HA exerted at least 97% TRAP inhibitory effect. In some embodiments, the pooled fetal support tissue demonstrates adequate TRAP potency if at least about 100 µg/ml of HA exerted at least 98% TRAP inhibitory effect. In some embodiments, the pooled fetal support tissue demonstrates adequate TRAP potency if at least about 100 µg/ml of HA exerted at least 99% TRAP inhibitory effect.

In some embodiments, the pooled fetal support tissue demonstrates adequate TRAP potency if at least about 300 µg/ml of HA exerted at least 60%, 65%, 70%, 75%, 80%, 85%, 90%, 95%, 97%, 98%, 99% TRAP inhibitory effect. In some embodiments, the pooled fetal support tissue demonstrates adequate TRAP potency if at least about 300 µg/ml of HA exerted at least 60% TRAP inhibitory effect. In some embodiments, the pooled fetal support tissue demonstrates adequate TRAP potency if at least about 300 µg/ml of HA exerted at least 65% TRAP inhibitory effect. In some embodiments, the pooled fetal support tissue demonstrates adequate TRAP potency if at least about 300 µg/ml of HA exerted at least 70% TRAP inhibitory effect. In some embodiments, the pooled fetal support tissue demonstrates adequate TRAP potency if at least about 300 µg/ml of HA exerted at least 75% TRAP inhibitory effect. In some embodiments, the pooled fetal support tissue demonstrates adequate TRAP potency if at least about 300 µg/ml of HA exerted at least 80% TRAP inhibitory effect. In some embodiments, the pooled fetal support tissue demonstrates adequate TRAP potency if at least about 300 µg/ml of HA exerted at least 85% TRAP inhibitory effect. In some embodiments, the pooled fetal support tissue demonstrates adequate TRAP potency if at least about 300 µg/ml of HA exerted at least 90% TRAP inhibitory effect. In some embodiments, the pooled fetal support tissue demonstrates adequate TRAP potency if at least about 300 µg/ml of HA exerted at least 95% TRAP inhibitory effect. In some embodiments, the pooled fetal support tissue demonstrates adequate TRAP potency if at least about 300 µg/ml of HA exerted at least 97% TRAP inhibitory effect. In some embodiments, the pooled fetal support tissue demonstrates adequate TRAP potency if at least about 300 µg/ml of HA exerted at least 98% TRAP inhibitory effect. In some embodiments, the pooled fetal support tissue demonstrates adequate TRAP potency if at least about 300 µg/ml of HA exerted at least 99% TRAP inhibitory effect.

In some embodiments, the pooled fetal support tissue demonstrates adequate TRAP potency if at least about 300 µg/ml of HA exerted greater than 60%, 65%, 70%, 75%, 80%, 85%, 90%, 95% TRAP inhibitory effect. In some embodiments, the pooled fetal support tissue demonstrates adequate TRAP potency if at least about 300 µg/ml of HA exerted greater than 60% TRAP inhibitory effect. In some embodiments, the pooled fetal support tissue demonstrates adequate TRAP potency if at least about 300 µg/ml of HA exerted greater than 65% TRAP inhibitory effect. In some embodiments, the pooled fetal support tissue demonstrates adequate TRAP potency if at least about 300 µg/ml of HA exerted greater than 70% TRAP inhibitory effect. In some embodiments, the pooled fetal support tissue demonstrates adequate TRAP potency if at least about 300 µg/ml of HA exerted greater than 75% TRAP inhibitory effect. In some embodiments, the pooled fetal support tissue demonstrates adequate TRAP potency if at least about 300 µg/ml of HA exerted greater than 80% TRAP inhibitory effect. In some embodiments, the pooled fetal support tissue demonstrates adequate TRAP potency if at least about 300 µg/ml of HA exerted greater than 85% TRAP inhibitory effect. In some embodiments, the pooled fetal support tissue demonstrates adequate TRAP potency if at least about 300 µg/ml of HA exerted greater than 90% TRAP inhibitory effect. In some embodiments, the pooled fetal support tissue demonstrates adequate TRAP potency if at least about 300 µg/ml of HA exerted greater than 95% TRAP inhibitory effect.

HA Assay: Hyaluronic Acid (HA) is a major extracellular matrix in both AM and UC and is a component of the HC-HA/PTX3 complex. The HA assay disclosed herein is validated and tested to assess stability of the fetal support tissue extract, such as, HC-HA/PTX3. The HA assay can be central to the release of a composition or drug of a fetal support tissue wherein the HA assay is an identity and potency measure. In certain embodiments, the hyaluronic acid (HA) in pooled fetal support tissue and/or products possesses adequate potency if the HA content obtained is at least 90 µg/ml. In some embodiments the pooled fetal support tissue extract and/or composition possesses adequate HA potency when the HA test kit has an "no less than" (NLT) content of at least 50 µg/ml, 60 µg/ml, 70 µg/ml, 80 µg/ml, 90 µg/ml, 100 µg/ml, 110 µg/ml, 120 µg/ml, 130

µg/ml, 140 µg/ml, 150 µg/ml. In some embodiments the pooled fetal support tissue extract and/or composition possesses adequate HA potency when the HA test kit has an "no less than" (NLT) content of at least 50 µg/ml, 60 µg/ml, 70 µg/ml, 80 µg/ml, 90 µg/ml, 100 µg/ml, 110 µg/ml, 120 µg/ml, 130 µg/ml, 140 µg/ml, 150 µg/ml, 160 µg/ml, 170 µg/ml, 180 µg/ml, 190 µg/ml, 200 µg/ml, 250 µg/ml, 300 µg/ml, 350 µg/ml, 400 µg/ml, 450 µg/ml, 500 µg/ml, 550 µg/ml, 600 µg/ml, 650 µg/ml, 700 µg/ml, 750 µg/ml, 800 µg/ml, 850 µg/ml, 900 µg/ml, 950 µg/ml, 1,000 µg/ml, 2,000 µg/ml, 3,000 µg/ml. In some embodiments the pooled fetal support tissue extract and/or composition possesses adequate HA potency when the HA test kit has an "no less than" (NLT) content of at least 50 µg/ml. In some embodiments the pooled fetal support tissue extract and/or composition possesses adequate HA potency when the HA test kit has an NLT content of at least 60 µg/ml. In some embodiments the pooled fetal support tissue extract and/or composition possesses adequate HA potency when the HA test kit has an NLT content of at least 70 µg/ml. In some embodiments the pooled fetal support tissue extract and/or composition possesses adequate HA potency when the HA test kit has an NLT content of at least 80 µg/ml. In some embodiments the pooled fetal support tissue extract and/or composition possesses adequate HA potency when the HA test kit has an NLT content of at least 90 µg/ml. In some embodiments the pooled fetal support tissue extract and/or composition possesses adequate HA potency when the HA test kit has an NLT content of at least 100 µg/ml. In some embodiments the pooled fetal support tissue extract and/or composition possesses adequate HA potency when the HA test kit has an NLT content of at least 110 µg/ml. In some embodiments the pooled fetal support tissue extract and/or composition possesses adequate HA potency when the HA test kit has an NLT content of at least 120 µg/ml. In some embodiments the pooled fetal support tissue extract and/or composition possesses adequate HA potency when the HA test kit has an NLT content of at least 130 µg/ml. In some embodiments the pooled fetal support tissue extract and/or composition possesses adequate HA potency when the HA test kit has an NLT content of at least 140 µg/ml. In some embodiments the pooled fetal support tissue extract and/or composition possesses adequate HA potency when the HA test kit has an NLT content of at least 150 µg/ml. In some embodiments the pooled fetal support tissue extract and/or composition possesses adequate HA potency when the HA test kit has an NLT content of at least 160 µg/ml. In some embodiments the pooled fetal support tissue extract and/or composition possesses adequate HA potency when the HA test kit has an NLT content of at least 170 µg/ml. In some embodiments the pooled fetal support tissue extract and/or composition possesses adequate HA potency when the HA test kit has an NLT content of at least 180 µg/ml. In some embodiments the pooled fetal support tissue extract and/or composition possesses adequate HA potency when the HA test kit has an NLT content of at least 190 µg/ml. In some embodiments the pooled fetal support tissue extract and/or composition possesses adequate HA potency when the HA test kit has an NLT content of at least 200 µg/ml. In some embodiments the pooled fetal support tissue extract and/or composition possesses adequate HA potency when the HA test kit has an NLT content of at least 250 µg/ml. In some embodiments the pooled fetal support tissue extract and/or composition possesses adequate HA potency when the HA test kit has an NLT content of at least 300 µg/ml. In some embodiments the pooled fetal support tissue extract and/or composition possesses adequate HA potency when the HA test kit has an NLT content of at least 350 μg/ml. In some embodiments the pooled fetal support tissue extract and/or composition possesses adequate HA potency when the HA test kit has an NLT content of at least 400 μg/ml. In some embodiments the pooled fetal support tissue extract and/or composition possesses adequate HA potency when the HA test kit has an NLT content of at least 450 μg/ml. In some embodiments the pooled fetal support tissue extract and/or composition possesses adequate HA potency when the HA test kit has an NLT content of at least 500 μg/ml. In some embodiments the pooled fetal support tissue extract and/or composition possesses adequate HA potency when the HA test kit has an NLT content of at least 550 μg/ml. In some embodiments the pooled fetal support tissue extract and/or composition possesses adequate HA potency when the HA test kit has an NLT content of at least 600 μg/ml. In some embodiments the pooled fetal support tissue extract and/or composition possesses adequate HA potency when the HA test kit has an NLT content of at least 650 μg/ml. In some embodiments the pooled fetal support tissue extract and/or composition possesses adequate HA potency when the HA test kit has an NLT content of at least 700 μg/ml. In some embodiments the pooled fetal support tissue extract and/or composition possesses adequate HA potency when the HA test kit has an NLT content of at least 750 μg/ml. In some embodiments the pooled fetal support tissue extract and/or composition possesses adequate HA potency when the HA test kit has an NLT content of at least 800 μg/ml. In some embodiments the pooled fetal support tissue extract and/or composition possesses adequate HA potency when the HA test kit has an NLT content of at least 850 μg/ml. In some embodiments the pooled fetal support tissue extract and/or composition possesses adequate HA potency when the HA test kit has an NLT content of at least 900 μg/ml. In some embodiments the pooled fetal support tissue extract and/or composition possesses adequate HA potency when the HA test kit has an NLT content of at least 1,000 μg/ml.

Bicinchoninic Acid (BCA) Protein Assay (BCA): The BCA assay is a quantitative and analytical assay to measure total protein content of fetal support tissue and/or product including, HC-HA/PTX3 complex, tissue matrix, growth factors/cytokines and other bioactive factors found in the tissue or drug substance. The BCA assay is one of the initial product release tests to assess identity and potency. The BCA assay disclosed herein is validated and tested to assess stability of the fetal support tissue extract, such as, HC-HA/PTX3. The BCA assay can be central to the release of a composition or drug of a fetal support tissue wherein the BCA assay is an identity and potency measure. In certain embodiments, the total protein content in pooled fetal support tissue and/or products has adequate potency if the BCA assay detects total protein content of "no less than" (NLT) at least 20 μg/ml, 30 μg/ml, 40 μg/ml, 50 μg/ml, 60 μg/ml, 70 μg/ml, 80 μg/ml, 90 μg/ml, 100 μg/ml, 110 μg/ml, 120 μg/ml, 130 μg/ml, 140 μg/ml, 150 μg/ml, 160 μg/ml, 170 μg/ml, 180 μg/ml, 190 μg/ml, 200 μg/ml, 220 μg/ml, 230 μg/ml, 240 μg/ml, 250 μg/ml, 260 μg/ml, 270 μg/ml, 280 μg/ml, 290 μg/ml, 300 μg/ml, 310 μg/ml, 320 μg/ml, 330 μg/ml, 340 μg/ml, 350 μg/ml, 360 μg/ml, 370 μg/ml, 380 μg/ml, 390 μg/ml, 400 μg/ml, 450 μg/ml, 500 μg/ml, 550 μg/ml, 600 μg/ml, 650 μg/ml, 700 μg/ml, 750 μg/ml, 800 μg/ml, 850 μg/ml, 900 μg/ml, 950 μg/ml, 970 μg/ml, 1,000 μg/ml, 2,000 μg/ml, 3,000 μg/ml, 4,000 μg/ml, 5,000 μg/ml. In certain embodiments, the total protein content in pooled fetal support tissue and/or products has adequate potency if the BCA assay detects total protein content of NLT at least 30 μg/ml. In certain embodiments, the total protein content in pooled fetal support tissue and/or products has adequate if the BCA assay detects total protein content of NLT at least 40 μg/ml. In certain embodiments, the total protein content in pooled fetal support tissue and/or products has adequate potency if the BCA assay detects total protein content of NLT at least 50 μg/ml. In certain embodiments, the total protein content in pooled fetal support tissue and/or products has adequate potency if the BCA assay detects total protein content of NLT at least 60 μg/ml. In certain embodiments, the total protein content in pooled fetal support tissue and/or products has adequate potency if the BCA assay detects total protein content of NLT at least 70 μg/ml. In certain embodiments, the total protein content in pooled fetal support tissue and/or products has adequate if the BCA assay detects total protein content of NLT at least 80 μg/ml. In certain embodiments, the total protein content in pooled fetal support tissue and/or products has adequate potency if the BCA assay detects total protein content of NLT than at least 90 μg/ml. In certain embodiments, the total protein content in pooled fetal support tissue and/or products has adequate potency if the BCA assay detects total protein content of NLT at least 100 μg/ml. In certain embodiments, the total protein content in pooled fetal support tissue and/or products has adequate potency if the BCA assay detects total protein content of NLT at least 110 μg/ml. In certain embodiments, the total protein content in pooled fetal support tissue and/or products has adequate potency if the BCA assay detects total protein content of NLT at least 120 μg/ml. In certain embodiments, the total protein content in pooled fetal support tissue and/or products has adequate potency if the BCA assay detects total protein content of NLT at least 130 μg/ml. In certain embodiments, the total protein content in pooled fetal support tissue and/or products has adequate potency if the BCA assay detects total protein content of NLT at least 140 μg/ml. In certain embodiments, the total protein content in pooled fetal support tissue and/or products has adequate potency if the BCA assay detects total protein content of NLT at least 150 μg/ml. In certain embodiments, the total protein content in pooled fetal support tissue and/or products has adequate potency if the BCA assay detects total protein content of NLT at least 160 μg/ml. In certain embodiments, the total protein content in pooled fetal support tissue and/or products has adequate potency if the BCA assay detects total protein content of NLT at least 170 μg/ml. In certain embodiments, the total protein content in pooled fetal support tissue and/or products has adequate potency if the BCA assay detects total protein content of NLT at least 180 μg/ml. In certain embodiments, the total protein content in pooled fetal support tissue and/or products has adequate if the BCA assay detects total protein content of NLT at least 190 μg/ml. In certain embodiments, the total protein content in pooled fetal support tissue and/or products has adequate potency if the BCA assay detects total protein content of NLT at least 200 μg/ml. In certain embodiments, the total protein content in pooled fetal support tissue and/or products has adequate potency if the BCA assay detects total protein content of NLT at least 210 μg/ml. In certain embodiments, the total protein content in pooled fetal support tissue and/or products has adequate potency if the BCA assay detects total protein content of NLT at least 220 μg/ml. In certain embodiments, the total protein content in pooled fetal support tissue and/or products has adequate potency if the BCA assay detects total protein content of NLT at least 230 μg/ml. In certain embodiments, the total protein content in pooled fetal support tissue and/or products has adequate potency if the BCA assay detects total protein content of NLT at least 240 μg/ml. In certain embodiments, the total protein content in pooled fetal support tissue and/or products has adequate potency if the BCA assay detects total protein content of NLT at least 250 µg/ml. In certain embodiments, the total protein content in pooled fetal support tissue and/or products has adequate potency if the BCA assay detects total protein content of NLT at least 260 µg/ml. In certain embodiments, the total protein content in pooled fetal support tissue and/or products has adequate potency if the BCA assay detects total protein content of NLT at least 270 µg/ml. In certain embodiments, the total protein content in pooled fetal support tissue and/or products has adequate potency if the BCA assay detects total protein content of NLT at least 280 µg/ml. In certain embodiments, the total protein content in pooled fetal support tissue and/or products has adequate potency if the BCA assay detects total protein content of an NLT at least 290 µg/ml. In certain embodiments, the total protein content in pooled fetal support tissue and/or products has adequate potency if the BCA assay detects total protein content of an NLT at least 300 µg/ml. In certain embodiments, the total protein content in pooled fetal support tissue and/or products has adequate potency if the BCA assay detects total protein content of NLT at least 310 µg/ml. In certain embodiments, the total protein content in pooled fetal support tissue and/or products has adequate potency if the BCA assay detects total protein content of NLT at least 320 µg/ml. In certain embodiments, the total protein content in pooled fetal support tissue and/or products has adequate potency if the BCA assay detects total protein content of NLT at least 330 µg/ml. In certain embodiments, the total protein content in pooled fetal support tissue and/or products has adequate potency if the BCA assay detects total protein content of NLT at least 340 µg/ml. In certain embodiments, the total protein content in pooled fetal support tissue and/or products has adequate potency if the BCA assay detects total protein content of an NLT at least 350 µg/ml. In certain embodiments, the total protein content in pooled fetal support tissue and/or products has adequate potency if the BCA assay detects total protein content of NLT at least 360 µg/ml. In certain embodiments, the total protein content in pooled fetal support tissue and/or products has adequate potency if the BCA assay detects total protein content of an NLT at least 370 µg/ml. In certain embodiments, the total protein content in pooled fetal support tissue and/or products has adequate if the BCA assay detects total protein content of NLT at least 380 µg/ml. In certain embodiments, the total protein content in pooled fetal support tissue and/or products has adequate potency if the BCA assay detects total protein content of NLT at least 390 µg/ml. In certain embodiments, the total protein content in pooled fetal support tissue and/or products has adequate potency if the BCA assay detects total protein content of NLT at least 400 µg/ml. In certain embodiments, the total protein content in pooled fetal support tissue and/or products has adequate potency if the BCA assay detects total protein content of NLT at least 450 µg/ml. In certain embodiments, the total protein content in pooled fetal support tissue and/or products has adequate potency if the BCA assay detects total protein content of NLT at least 500 µg/ml. In certain embodiments, the total protein content in pooled fetal support tissue and/or products has adequate potency if the BCA assay detects total protein content of NLT at least 550 µg/ml. In certain embodiments, the total protein content in pooled fetal support tissue and/or products has adequate potency if the BCA assay detects total protein content of NLT at least 600 µg/ml. In certain embodiments, the total protein content in pooled fetal support tissue and/or products has adequate potency if the BCA assay detects total protein content of NLT at least 650 µg/ml. In certain embodiments, the total protein content in pooled fetal support tissue and/or products has adequate potency if the BCA assay detects total protein content of NLT at least 700 µg/ml. In certain embodiments, the total protein content in pooled fetal support tissue and/or products has adequate potency if the BCA assay detects total protein content of NLT at least 750 µg/ml. In certain embodiments, the total protein content in pooled fetal support tissue and/or products has adequate potency if the BCA assay detects total protein content of NLT at least 800 µg/ml. In certain embodiments, the total protein content in pooled fetal support tissue and/or products has adequate potency if the BCA assay detects total protein content of NLT at least 850 µg/ml. In certain embodiments, the total protein content in pooled fetal support tissue and/or products has adequate potency if the BCA assay detects total protein content of NLT at least 900 µg/ml. In certain embodiments, the total protein content in pooled fetal support tissue and/or products has adequate potency if the BCA assay detects total protein content of NLT at least 950 µg/ml. In certain embodiments, the total protein content in pooled fetal support tissue and/or products has adequate potency if the BCA assay detects total protein content of NLT at least 970 µg/ml. In certain embodiments, the total protein content in pooled fetal support tissue and/or products has adequate potency if the BCA assay detects total protein content of NLT at least 1,000 µg/ml.

M2 Polarization Assay based on NO measurement: Lipopolysaccharide (LPS) and interferon gamma (IFNγ) can stimulate murine macrophage cell line RAW264.7 cells to polarize into M1 macrophages, a pro-inflammatory phenotype, and produce high nitric oxide (NO) through upregulation of inducible NO synthase (iNOS), a pro-inflammatory mediator, while M2 macrophages, an anti-inflammatory phenotype, produce low NO. Therefore, inhibition of NO production indicates an anti-inflammatory efficacy via downregulation of M1 macrophages. Disclosed herein in some embodiments, a NO assay can demonstrate the anti-inflammatory effectiveness of HC-HA/PTX3 or HC-HA/PTX3-containing tissue extracts of the pooled fetal support tissue (e.g., FIG. 5). In some embodiments, the pooled fetal support tissue possesses adequate potency if a statistically significant difference compared to positive control is exhibited for fetal support tissue.

Filtration of Liquid Extracts: Sterilization and Particle Separation

In some embodiments, the fetal support tissue is subject to sterilization by any suitable method. Fetal support tissues, in some embodiments, are sterilized by irradiation, such as for example, sterilization by gamma radiation, by exposure to chemical sterilant, by heat, by filtration, by exposure to ethylene oxide gas, by membrane filtration with appropriate pore sizes, by electron beam (E-beam) radiation, or by any process which makes the fetal support tissue free of contamination by living microorganisms while preserving the biological activity of bioactive components disclosed herein.

In some embodiments, filtration using different filters with different pore sizes can be used to control the particle size as a purpose or to sterilize the liquid tissue extract. In some embodiments, the fetal support tissue is sterilized by filtration. In some embodiments, sterilizing the fetal support tissue by filtration comprises passing the fetal support tissue through a filter. In some embodiments, the filter pore size is selected to prevent bacteria, yeasts, molds, or viruses from passing through the filter. In some instances where the sterilization by filtration is used to sterilize a liquid form, the filtration process used a filter with the pore size less than or equal to 0.2 um.

In some embodiments, the fetal support tissue extract is filtered to control for particle sizes. In some embodiments, the filter comprises pores having an average size of about 0.1-0.2 μm or less, 0.2-0.3 μm or less, 0.3-0.4 μm or less, 0.4-0.5 μm or less, 0.5-0.6 μm or less, 0.6-0.7 μm or less, 0.7-0.8 μm or less, 0.8-0.9 μm or less, 0.9-1 μm or less, 1-2 μm or less, 2-3 μm or less, 3-4 μm or less, 4-5 μm or less, 5-10 μm or less, 10-20 μm or less, 20-30 μm or less, 30-40 μm or less, 40-50 μm or less, 50-100 μm or less. In some embodiments, the filter has an average pore size of about. 05-0.2 μm. In some embodiments, the filter comprises pores having an average size of about 0.4 μm or less. In some embodiments, the filter comprises pores having an average size of about 0.3 μm or less. In some embodiments, the filter comprises pores having an average size of about 0.2 μm or less. In some embodiments, the filter comprises pores having an average size of about 0.2 μm. In some embodiments, sterilization by filtration comprises passing the fetal support tissue through a first filter and a second filter. In some embodiments the first filter comprises an average pore size that is larger than the average pore size of the second filter. In some embodiments, either the first or second filter have an average pore size of about 0.1-0.2 μm or less, 0.2-0.3 μm or less, 0.3-0.4 μm or less, 0.4-0.5 μm or less, 0.5-0.6 μm or less, 0.6-0.7 μm or less, 0.7-0.8 μm or less, 0.8-0.9 μm or less, 0.9-1 μm or less, 1-2 μm or less, 2-3 μm or less, 3-4 μm or less, 4-5 μm or less, 5-10 μm or less. In some embodiments each of the first and second filters have an average pore size of about 0.05-0.2 μm. In some embodiments, the first filter has an average pore size of about 0.6 μm or less and the second filter has an average pore size of about 0.4 μm or less. In some embodiments, the first filter has an average pore size of about 0.5 μm or less and the second filter has an average pore size of about 0.3 μm or less. In some embodiments, the first filter has an average pore size of about 0.45 μm or less and the second filter has an average pore size of about 0.2 μm or less. In some embodiments, the first filter has an average pore size of about 0.45 μm and the second filter has an average pore size of about 0.2 μm.

In some embodiments, the any of the filters described herein is housed in a sterilization unit. In some embodiments, any of the filters described herein are membranes comprising polyethersulfone (PES), polyvinylidene fluoride (PVDF), polytetrafluorethylene (PTFE), polypropylene, polyethylene, polyamide, cellulose, cellulose nitrate, nylon, or a combination thereof. In some embodiments, any of the filters described herein have been sterilized by gamma irradiation. In some embodiments, the filtration pressure during filtration is about 0-10 psi, about 10-20 psi, about 20-30 psi, about 30-40 psi, about 40-50 psi, about 50-60 psi, about 60-70 psi, about 70-80 psi, about 80-90 psi or about 90-100 psi. In some embodiments, the effective filtration area of any of the filters described herein is from about 0-20 cm², about 20-40 cm², about 40-60 cm², about 60-80 cm², about 80-100 cm², about 100-120 cm², about 120-140 cm², about 140-160 cm², about 160-180 cm², or about 180-200 cm². In some embodiments, the overall diameter of the filter is about 0-10 mm, about 20-20 mm, about 20-30 mm, about 30-40 mm, about 40-50 mm, about 50-60 mm, about 60-70 mm, about 70-80 mm, about 80-90 mm, about 90-100 mm, about 100-200 mm, about 200-300 mm, about 300-400 mm, about 400-500 mm, about 500-600 mm, about 600-700 mm, about 700-800 mm, about 800-900 mm, or about 900-1000 mm. In some embodiments, the overall diameter of the filter is about 67 mm. In some embodiments, the overall diameter of the filter is about 68 mm. In some embodiments, the overall height of the filter is about 0-10 mm, about 20-20 mm, about 20-30 mm, about 30-40 mm, about 40-50 mm, about 50-60 mm, about 60-70 mm, about 70-80 mm, about 80-90 mm, about 90-100 mm, about 100-200 mm, about 200-300 mm, about 300-400 mm, about 400-500 mm, about 500-600 mm, about 600-700 mm, about 700-800 mm, about 800-900 mm, or about 900-1000 mm. In some embodiments, the overall height of the filter is about 82 mm. In some embodiments, the overall height of the filter is about 83 mm. In some embodiments, the filter has successfully passed a manufacturing forward flow test. In some embodiments, the forward flow rate limit for the filter is about 0.1, 0.2, 0.3, 0.4, 0.5, 0.6, 0.7, 0.8, 0.9, 1.0, or more than 1.0 mL/minute. In some embodiments, the forward flow rate limit for the filter is about 0.3, 0.4, 0.5, 0.6, 0.7, 0.8, 0.9, 1.0, or more than 1.0 mL/minute at a test pressure of about 2400, 2450, 2500, 2550, 2600, 2650, 2700, 2750, 2800, 2850, 2900, or more than 2900 mbar when fully wetted with water. In some embodiments, the forward flow limit for the filter is about 0.58 mL/minute, at a test pressure of about 2760 mbar when fully wetted with water. In some embodiments, the forward flow limit for the filter is about 0.40-0.50 mL/minute, 0.50-0.60 mL/minute, or 0.60-0.70 mL/minute at a test pressure of about 2700-2800 mbar when fully wetted with water. In some embodiments, the forward flow test limit has been validated for bacterial removal by correlation of the forward flow limit with a microbiological challenge test. In some embodiments, the fetal support tissue is test for retention of an acceptable challenge microorganism to validate the bacterial retention of the filter using procedures in conformance with the applicable Food and Drug Administration guidelines.

In some embodiments, a fetal support tissue powder product disclosed herein is subject to terminal sterilization by any suitable (e.g., medically acceptable) method. In some embodiments, a fetal support tissue powder product is disclosed herein is exposed to gamma radiation for a period of time sufficient to sterilize the fetal support tissue powder product disclosed herein.

In some embodiments, a fetal support tissue powder product disclosed herein is exposed to gamma radiation at about 10 to about 75 kilogray (kGy) for a period of time sufficient to sterilize the fetal support tissue powder product. In some embodiments, a fetal support tissue powder product disclosed herein is exposed to gamma radiation at about 10 to about 30 kGy for a period of time sufficient to sterilize the fetal support tissue. In some embodiments, a fetal support tissue powder product disclosed herein is exposed to gamma radiation at about 15 to about 30 kGy for a period of time sufficient to sterilize the fetal support tissue. In some embodiments, a fetal support tissue powder product disclosed herein is exposed to gamma radiation at about 25 kGy for a period of time sufficient to sterilize the fetal support tissue. In some embodiments, a fetal support tissue powder product disclosed herein is exposed to gamma radiation at about 17.5 kGy for a period of time sufficient to sterilize the fetal support tissue powder product.

In some embodiments the fetal support tissue powder product disclosed herein is subject to electron beam (E-Beam) sterilization. In some embodiments, a fetal support tissue disclosed herein is exposed to E-Beam radiation at about 10 to about 75 kilogray for a period of time sufficient to sterilize the fetal support tissue. In some embodiments, a fetal support tissue disclosed herein is exposed to E-Beam radiation at about 10 to about 30 kGy for a period of time sufficient to sterilize the fetal support tissue. In some embodiments, a fetal support tissue disclosed herein is exposed to E-Beam radiation at about 15 to about 30 kGy for a period of time sufficient to sterilize the fetal support tissue. In some embodiments, a fetal support tissue disclosed herein is exposed to E-Beam radiation at about 25 kGy for a period of time sufficient to sterilize the fetal support tissue. In some embodiments, a fetal support tissue disclosed herein is exposed to E-Beam radiation at about 17.5 kGy for a period of time sufficient to sterilize the fetal support tissue.

In some embodiments, a fetal support tissue powder product disclosed herein is exposed to an electron beam for a period of time sufficient to sterilize the fetal support tissue powder product. In some embodiments, a fetal support tissue powder product disclosed herein is exposed to X-ray radiation for a period of time sufficient to sterilize the fetal support tissue powder product. In some embodiments, a fetal support tissue powder product disclosed herein is exposed to UV radiation for a period of time sufficient to sterilize the fetal support tissue powder product.

Provided herein, in certain embodiments, are methods for preparing a fetal support tissue, wherein the methods result in an improved percentage of HA recovered. In some embodiments, at least or about 50%, 55%, 60%, 65%, 70%, 75% 80%, 85%, 90%, 95%, 99%, or more than 99% of the HA is recovered. In some embodiments, at least or about 50%, 55%, 60%, 65%, 70%, 75% 80%, 85%, 90%, 95%, 99%, or more than 99% of the HA is recovered. In some embodiments, at least or about 50%, 55%, 60%, 65%, 70%, 75% 80%, 85%, 90%, 95%, 99%, or more than 99% of the HA is recovered. In some embodiments, at least or about 50% of the HA is recovered. In some embodiments, at least or about 55% of the HA is recovered. In some embodiments, at least or about 60% of the HA is recovered. In some embodiments, at least or about 65% of the HA is recovered. In some embodiments, at least or about 70% of the HA is recovered. In some embodiments, at least or about 75% of the HA is recovered. In some embodiments, at least or about 80% of the HA is recovered. In some embodiments, at least or about 85% of the HA is recovered. In some embodiments, at least or about 85% of the HA is recovered. In some embodiments, at least or about 95% of the HA is recovered. In some embodiments, at least or about 99% of the HA is recovered. In some embodiments, at least or about 99% or more of the HA is recovered. In some embodiments, the HA is HMW HA. In some embodiments, the methods result in preservation of nHC-HA/PTX3. In some embodiments, the potency of nHC-HA/PTX3 is preserved by at least or about 75% 80%, 85%, 90%, 95%, 99%, or more than 99% of the HC-HA/PTX3 is recovered. In some embodiments, the potency of nHC-HA/PTX3 is preserved by at least or about 75% of the HC-HA/PTX3 is recovered. In some embodiments, the potency of nHC-HA/PTX3 is preserved by at least or about 80% of the HC-HA/PTX3 is recovered. In some embodiments, the potency of nHC-HA/PTX3 is preserved by at least or about 85% of the HC-HA/PTX3 is recovered. In some embodiments, the potency of nHC-HA/PTX3 is preserved by at least or about 90% of the HC-HA/PTX3 is recovered. In some embodiments, the potency of nHC-HA/PTX3 is preserved by at least or about 95% of the HC-HA/PTX3 is recovered. In some embodiments, the potency of nHC-HA/PTX3 is preserved by at least or about 99% of the HC-HA/PTX3 is recovered. In some embodiments, the potency of nHC-HA/PTX3 is preserved by at least or about 99% or more of the HC-HA/PTX3 is recovered.

Methods as described herein, in certain embodiments, result in removal of particulates or degradants. In some embodiments, the methods described herein result in at least or about 75% 80%, 85%, 90%, 95%, 99%, or more than 99% of the particulates or degradants removed. In some embodiments, the particulates or degradants comprise chloride.

Rehydration

In some embodiments, the fetal support tissue is partially or fully rehydrated so that the powder extract becomes a liquid extract. In some embodiments, the rehydration allows the fetal support tissue that is a dry powder to be reconstituted into liquid form using water or a suitable buffer. In some embodiments, the rehydrated fetal support tissue or tissue extract further undergoes filtration for sterilization purposes. Sterilization of the rehydrated fetal support tissue extract is completed by filtration of the extract using a filter pore size of about less than or equal to 0.2 μm.

In some embodiments, the rehydrated tissue extract further undergoes filtration to control the particle sizes such as for example, the extract is further centrifuged variously to yield a different particle size for dosing or formulation of the fetal support tissue extract/composition. In some embodiments, the fetal support tissue is rehydrated by contacting the fetal support tissue with a buffer or with water. In some embodiments, the fetal support tissue is contacted with an isotonic buffer. In some embodiments, the fetal support tissue is contacted with saline. In some embodiments, the fetal support tissue is contacted with PBS. In some embodiments, the fetal support tissue is contacted with Ringer's solution. In some embodiments, the Ringer's solution is Lactate Ringer's Saline. In some embodiments, the fetal support tissue is contacted with Hartmann's solution. In some embodiments, the fetal support tissue is contacted with a TRIS-buffered saline. In some embodiments, the fetal support tissue is contacted with a HEPES-buffered saline; 50% DMEM+50% Glycerol; 10%, 20%, 30%, 40%, 50%, 60%, 70%, 80%, 90% or 100% glycerol; and/or 10%, 20%, 30%, 40%, 50%, 60%, 70%, 80%, 90% or 100% propylene glycol.

In some embodiments, the fetal support tissue is contacted with a buffer for 10 minutes, 15 minutes, 20 minutes, 25 minutes, 30 minutes, 40 minutes, 1 hour, 2 hours, 3 hours, 4 hours, 5 hours, 6 hours, 12 hours, 18 hours, 24 hours, or more than 24 hours. In some embodiments, the UC product is contacted with a buffer for 2 days, 3 days, 4 days, 5 days, 6 days, 7 days, 1 week, 2 weeks, 3 weeks, 4 weeks, or more than 4 weeks. Disclosed herein are processes for generating fetal support tissue while preserving the biological activity of the fetal support tissue, including components of the fetal support tissue, such as HC-HA/PTX3, HA, growth factors, cytokines or other active components as disclosed throughout the specification and claims. In some embodiments, the fetal support tissue is stored for later use. In some embodiments, storing the fetal support tissue does not destroy the integrity of the fetal support tissue extracellular matrix. In some embodiments, the fetal support tissue is lyophilized. In some embodiments, the fetal support tissue is stored in any suitable storage medium.

In some embodiments, the fetal support tissue is optionally contacted with a substrate (i.e., a supportive backing). In some embodiments, the fetal support tissue is not contacted with a substrate. In some embodiments, the fetal support tissue is orientated such that the fetal support tissue is in contact with the substrate. In some embodiments, the fetal support tissue is orientated such that the stroma is in contact with the substrate. In some embodiments the fetal support tissue is orientated such that the epithelial side is in contact with the substrate.

In some embodiments, the fetal support tissue is attached to the substrate. In some embodiments, the substrate is nitrocellulose paper (NC). In some embodiments, the substrate is nylon membrane (NM). In some embodiments, the substrate is polyethersulfone membrane (PES).

Native HC-HA/PTX3 (nHC-HA/PTX3) Compositions

In some embodiments, the isolated nHC-HA/PTX3 complex is isolated from an amniotic tissue. In some embodiments, the isolated nHC-HA/PTX3 complex is isolated from an amniotic membrane or an umbilical cord. In some embodiments, the isolated nHC-HA/PTX3 complex is isolated from fresh, frozen or previously frozen placental amniotic membrane (PAM), fresh, frozen or previously frozen umbilical cord amniotic membrane (UCAM), fresh, frozen or previously frozen placenta, fresh, frozen or previously frozen umbilical cord, fresh, frozen or previously frozen chorion, fresh, frozen or previously frozen amnion-chorion, or any combinations thereof Such tissues can be obtained from any mammal, such as, for example, but not limited to a human, nonhuman primate, cow or pig or a combination thereof.

In some embodiments, the nHC-HA/PTX3 is purified by any suitable method. In some embodiments, the nHC-HA/PTX3 complex is purified by centrifugation (e.g., ultracentrifugation, gradient centrifugation), chromatography (e.g., ion exchange, affinity, size exclusion, and hydroxyapatite chromatography), gel filtration, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference).

In some embodiments, the nHC-HA/PTX3 is isolated from an extract. In some embodiments, the extract is prepared from an amniotic membrane extract. In some embodiments, the extract is prepared from an umbilical cord extract. In some embodiments, the umbilical cord extract comprises umbilical cord stroma and/or Wharton's jelly. In some embodiments, the nHC-HA/PTX3 complex is contained in an extract that is prepared by ultracentrifugation. In some embodiments, the nHC-HA/PTX3 complex is contained in an extract that is prepared by ultracentrifugation using a CsC1/4-6M guanidine HC1 gradient.

In some embodiments, the extract is prepared by at least 2 rounds of ultracentrifugation. In some embodiments, the extract is prepared by more than 2 rounds of ultracentrifugation (i.e., nHC-HA/PTX3$^{rd}$). In some embodiments, the extract is prepared by at least 4 rounds of ultracentrifugation (i.e., nHC-HA/PTX3 4$^{th}$). In some embodiments, the nHC-HA/PTX3 complex comprises a small leucine-rich proteoglycan. In some embodiments, the nHC-HA/PTX3 complex comprises HC1, HA, PTX3 and/or a small leucine-rich proteoglycan (SLRP).

In some embodiments, the fetal support tissue comprises nHC-HA/PTX3 and pharmaceutical excipient. In some embodiments, the fetal support tissue consists essentially of an nHC-HA/PTX3 complex. In some embodiments, the fetal support tissue comprises a pharmaceutically acceptable diluent, excipient, vehicle, or carrier. In some embodiments, proper formulation is dependent upon the route of administration selected.

In some embodiments, the nHC-HA/PTX3 complex is purified by immunoaffinity chromatography, affinity chromatography, or a combination thereof. In some embodiments, anti HC1 antibodies, anti-HC2 antibodies, or both are generated and affixed to a stationary support. In some embodiments, the HC-HA complex binds to the antibodies (e.g., via interaction of (a) an anti-HC1 antibody and HC1, (b) an anti-HC2 antibody and HC2, (c) an anti-PTX antibody and PTX3, (d) an anti-SLRP antibody and the SLRP, or (e) any combination thereof). In some embodiments, HABP is generated and affixed to a stationary support.

In some embodiments, the nHC-HA/PTX3 complex is purified from the insoluble fraction as described herein using one or more antibodies. In some embodiments, the nHC-HA/PTX3 complex is purified from the insoluble fraction as described herein using anti-SLRP antibodies.

In some embodiments, the nHC-HA/PTX3 complex is purified from the soluble fraction as described herein. In some embodiments, the nHC-HA/PTX3 complex is purified from the soluble fraction as described herein using anti-PTX3 antibodies.

In some embodiments, the fetal support tissue may contain components such as extracellular matrices, growth factors, cytokines, and the nHC-HA/PTX3 complex. In some embodiments, one extracellular matrix is a small leucine rich proteoglycan (SLRP). In some embodiments, the nHC-HA/PTX3 complex comprises a class I, class II, or class II SLRP. In some embodiments, the small leucine-rich proteoglycan is selected from among class I SLRPs, such as decorin and biglycan. In some embodiments, the small leucine-rich proteoglycan is selected from among class II SLRPs, such as fibromodulin, lumican, PRELP (proline arginine rich end leucine-rich protein), keratocan, and osteoadherin. In some embodiments, the small leucine-rich proteoglycan is selected from among class III SLRPs, such as epipycan and osteoglycin. In some embodiments, the small leucine-rich proteoglycan is selected from among bikunin, decorin, biglycan, and osteoadherin. In some embodiments, the small leucine-rich protein comprises a glycosaminoglycan. In some embodiments, the small leucine-rich proteoglycan comprises keratan sulfate.

In some embodiments, the pharmaceutical composition further comprises at least one pharmaceutically acceptable carrier. In some embodiments, the pharmaceutical composition further comprises an adjuvant, excipient, preservative, agent for delaying absorption, filler, binder, adsorbent, buffer, and/or solubilizing agent. Exemplary pharmaceutical compositions that are formulated to comprise an nHC-HA/PTX3 complex provided herein include, but are not limited to, a gel, solution, suspension, emulsion, syrup, granule, powder, homogenate, ointment, tablet, capsule, pill, paste, cream, lotion, a patch, sticks, film, paint, an aerosol, or a combination thereof. In some embodiments, the fetal support tissue comprising nHC-HA/PTX3 is a graft or a sheet.

Exemplary Biological Factors in Fetal Support Tissues

Disclosed herewith are fetal support tissues that contain bioactive factors that can be preserved and utilized in various applications as disclosed herein. Fetal support tissue disclosed herein, for example, amniotic membrane and umbilical cord contain several innate biological factors with numerous significant clinical efficacies disclosed herein. For example, nHC-HA/PTX3 complex—high molecular weight (HMW) hyaluronan (HA) covalently linked with heavy chain (HC) 1 from inter-α-trypsin inhibitor and further complexed with pentraxin3 (PTX3)—as exemplary key active components of umbilical cord and amniotic membrane responsible for the wound healing effects, other extracellular matrices, growth factors and cytokines and several other therapeutic effects (components) of fetal support tissue. Accordingly, production of a fetal support tissue product (e.g., an amniotic membrane and umbilical cord extract for use in wound healing) with a high yield of HC-HA/

PTX3, HA, and other proteins of interest is critical. Production of a fetal support tissue product using a process that reduces or prevents the degradation of the HC-HA/PTX3 complex and other proteins of interest, while concentrating these biomolecules is a critical factor when processing fetal support tissue compositions. Preventing degradation of HA and other proteins of interest is important because the degradation of such proteins can render a fetal support tissue product unsuitable for use.

Disclosed herein, in certain embodiments, are methods of preparing a fetal support tissue product comprising: (a) lyophilizing a pooled or not pooled fetal support tissue to generate a micronized, cryopulverized, (dry or wet), devitalized, decellularized (frozen), or a combination thereof, or in (b) extracting the processed fetal support tissue in an excipient to generate an extract; and (c) in sterilizing the fetal support tissue by filtration the extract using a membrane having a pore size of less than to about 0.2 μm. In some embodiments, the fetal support tissue is placental amniotic membrane (PAM), or substantially isolated PAM, umbilical cord amniotic membrane (UCAM) or substantially isolated UCAM, chorion or substantially isolated chorion, amnion-chorion or substantially isolated amnion-chorion, placenta or substantially isolated placenta, umbilical cord or substantially isolated umbilical cord, or any combinations thereof.

In some embodiments, diluted fetal support tissue comprises from about 1 μg/mL to about 1 mg/mL of HA, of which some is present as HC-HA/PTX3.

Described herein, in certain embodiments, are compositions comprising a therapeutically effective amount of a pooled composition comprising fetal support tissue. In some embodiments, the fetal support tissue comprises micronized fetal support tissue. In some embodiments, a pooled composition comprises fetal support tissue pooled from multiple donors. In some embodiments, the composition comprises fetal support tissue pooled from at least 15 donors. In some embodiments, the composition comprises fetal support tissue pooled from at least 30 donors. In some embodiments, the composition comprises fetal support tissue pooled from at least 45 donors. In some embodiments, the composition comprises fetal support tissue pooled from at least 10, 15, 20, 25, 30, 35, 40, 45, 50, 55, 60, 65, 70, 75, 80, 85, 90, 95, 100, or more than 100 donors. In some embodiments, a composition is not pooled if it comprises tissue from at most 5 donors. In some embodiments, a composition is not pooled if it comprises tissue from at most 9, 8, 7, 6, 5, 4, 3, or 2 donors.

Pooling Fetal Support Tissue Reduces Sample Variability and Improves Sample Consistency Described herein, in certain embodiments, are compositions comprising a pooled fetal support tissue or fetal support tissue extract or composition comprising reduced donor to donor (or subject to subject) variability as compared as to a non-pooled (individual donor) fetal support tissue extract composition. In some embodiments, the pooled composition comprises reduced variability as compared to a composition comprising fetal support tissue from at most 9, 8, 7, 6, 5, 4, 3, or 2 donors. In some embodiments, the pooled composition comprises reduced variability as compared to a composition comprising fetal support tissue from at most 5 donors. In some embodiments, the pooled composition comprises reduced variability as compared to a composition comprising fetal support tissue from one donor. Disclosed herein is a pooled fetal support tissue extract (in any form herein disclosed) may comprise reduced pooled sample-to-pooled sample variability, when compared to sample-to-sample variability of a non-pooled (individual) fetal support tissue extract. For example, when the percent coefficient of variation (CV %), on average, is computed for a pooled fetal support tissue product or extract, the CV % of pooled may be at least 2, 3, 4, or more-fold lower than the CV % of a non-pooled fetal support tissue product. Disclosed herein is a pooled fetal support tissue extract in any form herein disclosed) that comprises a pooled product which displays increased uniformity and improved sample consistency over the uniformity or sample consistency of a non-pooled fetal support tissue extract. For example, the pooled fetal support tissue extract (in any form e.g., composition, kits etcetera) may indicate improved consistency wherein the pooled extract exhibit reduced variation of activity of native HC-HA/PTX3 complex when compared to a non-pooled fetal support tissue extract (product, composition etcetera) as determined by an ODI-TRAP assay, BCA assay or HA quantitative assay. For example, the improvement in consistency of the pooled extract may be exhibited by reduced coefficient of variation of at least 10%. In some embodiments, the reduced coefficient of variation for pooled fetal support tissue extract when compared to non-pooled fetal support tissue extract may be 5% or less. In some embodiments, the reduced coefficient of variation for pooled fetal support tissue extract when compared to non-pooled fetal support tissue extract may be 4% or less. In some embodiments, the reduced coefficient of variation for pooled fetal support tissue extract when compared to non-pooled fetal support tissue extract may be about 3% or less. In some embodiments, the reduced coefficient of variation for pooled fetal support tissue extract when compared to non-pooled fetal support tissue extract may be about 2% or less.

Nonetheless, the present disclosure whether pooled fetal support donor samples, or single donor samples as well as any derived pooled and non-pooled fetal support tissue extracts (compositions, kits, products etcetera) retain the HA molecular weight (MW); there pooling does not alter both the HA MW nor HC-HA bond. The pooled fetal support tissue disclosed herein, and derived extracts or products provides for a higher yield product that also has more uniformity, such that there is less pooled sample-to-sample variability. As disclosed above and throughout the disclosure, pooling of samples improves consistency of the product even as it increases the protein yield (e.g., HA protein content) due to the reduction in variability as measured by reduction in coefficient of variation when compared to that obtained from non-pooled, single donor samples and/or extracts. As disclosed herein, the present disclosure produced by the pooling process fully retains the potency of the fetal support tissue extract (product/composition etcetera), e.g., fully retains the potency of the native HC-HA/PTX3 complex, while improving on the yield, uniformity, and consistency of the pooled extract. As such, the findings of the present disclosure argue for pooling of the fetal support tissue and/or fetal support tissue product.

In some embodiments, the fetal support tissue is a placental amniotic membrane, umbilical cord, umbilical cord amniotic membrane, chorion, amnion-chorion, placenta, amniotic stroma, amniotic jelly, or any combination thereof. In some embodiments, the fetal support tissue comprises extracellular matrix (ECM) of amniotic membrane (AM) and umbilical cord (UC). The fetal support tissue, for example, the ECM of AM/UC contain several innate biological factors useful for a number of purposes, including wound healing and reducing inflammation and scarring. Characterization data show that the fetal support tissue such as for example, the extracellular matrix (ECM) of AM and UC are enriched in hyaluronic acid (HA) having a critical or key matrix component called, the HC-HA/PTX3 complex (Heavy Chain 1-Hyaluronic Acid-Pentraxin 3). In some embodiments, the fetal support tissue comprises AM and UC wherein HC-HA/PTX3 is isolated and wherein the HC-HA/PTX3 is native (nHC-HA/PTX3). In some embodiments, the fetal support tissue comprises micronized fetal support tissue.

In some embodiments, the variability is determined by average particle size in the pooled composition. In some embodiments, the pooled composition comprises no more than about 10000 particles comprising a diameter more than about 10 μm. In some embodiments, the pooled composition comprises no more than about 10000, 9000, 8000, 7000, 6000, 5000, 4000, 3000, 2000, 1000, 500, 250, or 100 particles comprising a diameter more than about 10 μm or less than 10 μm, less than 5 μm, less than 1 μm or about 1 μm, about 1 μm to about 5 μm or about 5 μm to about 10 μm or a combination thereof. In some embodiments, the pooled composition comprises no more than about 10000, 9000, 8000, 7000, 6000, 5000, 4000, 3000, 2000, 1000, 500, 250, or 100 particles comprising a diameter more than about 10 μm or less than 10 μm, less than 5 μm, less than 1 μm or about 1 μm, about 1 μm to about 5 μm or about 5 μm to about 10 μm or a combination thereof. In some embodiments, the pooled composition comprises no more than about 1000 particles comprising a diameter more than about 25 μm. In some embodiments, the pooled composition comprises no more than about 1000, 900, 800, 700, 600, 500, 400, 300, 200, 100, or 100 particles comprising a diameter more than about 10, 15, 20, 25, 30, 35, 40, 45, or 50 μm. In some embodiments, the pooled composition comprises no more than about 10000, 9000, 8000, 7000, 6000, 5000, 4000, 3000, 2000, 1000, 500, 250, or 100 particles comprising a diameter more than about 10, 15, 20, 25, 30, 35, 40, 45, or 50 μm.

Described herein, in certain embodiments, are compositions comprising a therapeutically effective amount of a pooled composition comprising fetal support tissue, wherein the fetal support tissue comprises a particle size of a certain diameter. Further described herein, in certain embodiments, are compositions comprising a therapeutically effective amount of a pooled composition comprising fetal support tissue, wherein the fetal support tissue comprises a particle size of about 20 μm to about 240 μm in diameter. In some embodiments, the fetal support tissue comprises micronized fetal support tissue.

In some embodiments, the fetal support tissue comprises an average particle size of about 10 μm to about 300 μm, about 10 μm to about 250 μm, about 10 μm to about 200 μm, about 10 μm to about 150 μm, about 10 μm to about 100 μm, or about 10 μm to about 50 μm. In some embodiments, the fetal support tissue comprises an average particle of about 20 μm to about 200 μm in diameter. In some embodiments, the fetal support tissue comprises an average particle size of about 20 to about 40 μm in diameter. In some embodiments, the fetal support tissue comprises an average particle of about 20 μm to about 300 μm, about 20 μm to about 250 μm, about 20 μm to about 200 μm, about 20 μm to about 150 μm, about 20 μm to about 100 μm, about 20 μm to about 50 μm, about 50 μm to about 300 μm, about 50 μm to about 250 μm, about 50 μm to about 200 μm, about 50 μm to about 150 μm, or about 50 μm to about 100 μm. In some embodiments, the fetal support tissue comprises an average particle size of about 60 μm to about 120 μm in diameter. In some embodiments, the fetal support tissue comprises an average particle size of about 140 μm to about 240 μm in diameter. In some embodiments, the fetal support tissue comprises an average particle size of at least or about 10, 15, 20, 25, 30, 35, 40, 45, 50, 55, 60, 65, 70, 80, 90, 100, 120, 140, 160, 180, 200, 220, 240, 260, 280, or 300 μm in diameter. In some embodiments, the fetal support tissue comprises an average particle size of about 100 μm in diameter.

In some embodiments, the fetal support tissue comprises an average particle size of about 0.010 μm to about 0.3 μm, about 0.01 μm to about 0.25 μm, about 0.01 μm to about 0.2 μm, about 0.01 μm to about 0.15 μm, about 0.01 μm to about 0.1 μm, about 0.01 μm to about 0.5 μm, 0.10 μm to about 0.3 μm, about 0.1 μm to about 0.25 μm, about 0.1 μm to about 0.2 μm, about 0.1 μm to about 0.15 μm, about 0.1 μm to about 0.25 μm, or about 0.1 μm to about 0.5 μm. In some embodiments, the fetal support tissue comprises an average particle of about 0.20 μm to about 2.0 μm in diameter. In some embodiments, the fetal support tissue comprises an average particle size of about 0.20 μm to about 4.0 μm in diameter. In some embodiments, the fetal support tissue comprises an average particle of about 0.20 μm to about 3.0 μm, about 0.20 μm to about 2.5 μm, about 0.20 μm to about 2.0 μm, about 0.20 μm to about 1.5 μm, about 0.20 μm to about 1.0 μm, about 0.20 μm to about 5.0 μm, about 0.50 μm to about 3.0 μm, about 0.50 μm to about 2.5 μm, about 0.50 μm to about 2.0 μm, about 0.50 μm to about 1.5 μm, or about 0.50 μm to about 1.0 μm. In some embodiments, the fetal support tissue comprises an average particle size of about 0.60 μm to about 1.2 μm in diameter. In some embodiments, the fetal support tissue comprises an average particle size of at least or about 0.01, 0.02, 0.03, 0.04, 0.05, 0.06, 0.07, 0.08, 0.09, 0.10, 0.15, 0.20, 0.25, 0.3, 0.35, 0.40, 0.45, 0.50, 0.55, 0.60, 0.65, 0.70, 0.75, 0.80, 0.85, 0.90, 1.0, 1.5, 2.0, 2.5, 3.0, or more than 3.0 μm in diameter. In some embodiments, the fetal support tissue comprises an average particle size of about 0.50 μm in diameter. Disclosed herein are processes for generating fetal support tissue while preserving the biological activity of the fetal support tissue, including components of the fetal support tissue, such as for example, HA, (which exists as nHC-HA/PTX3 in AM/UC) whose potency is preserved as disclosed throughout the specification and claims.

Dosage Forms

Provided below are dosage forms of the compositions described herein comprising pooled composition comprising fetal support tissue.

In some embodiments, a pooled composition described herein is administered as an aqueous suspension. In some embodiments, an aqueous suspension comprises water, Ringer's solution and/or isotonic sodium chloride solution. In some embodiments, the Ringer's solution is Lactate Ringer's Saline. In some embodiments, an aqueous suspension comprises a sweetening or flavoring agent, coloring matters or dyes and, if desired, emulsifying agents or suspending agents, together with diluents water, ethanol, propylene glycol, glycerin, or combinations thereof. In some embodiments, an aqueous suspension comprises a suspending agent. In some embodiments, an aqueous suspension comprises sodium carboxymethylcellulose, methylcellulose, hydroxypropylmethyl-cellulose, sodium alginate, polyvinyl-pyrrolidone, gum tragacanth and/or gum acacia. In some embodiments, an aqueous suspension comprises a dispersing or wetting agent. In some embodiments, an aqueous suspension comprises a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. In some embodiments, an aqueous suspension comprises a preservative. In some embodiments, an aqueous suspension comprises ethyl, or n-propyl p-hydroxybenzoate. In some embodiments, an aqueous suspension comprises a sweetening agent. In some embodiments, an aqueous suspension comprises sucrose, saccharin, or aspartame.

In some embodiments, a pooled composition described herein is administered as an oily suspension. In some embodiments, an oily suspension is formulated by suspending the active ingredient in a vegetable oil (e.g., arachis oil, olive oil, sesame oil or coconut oil), or in mineral oil (e.g., liquid paraffin). In some embodiments, an oily suspension comprises a thickening agent (e.g., beeswax, hard paraffin or acetyl alcohol). In some embodiments, an oily suspension comprises sweetening agents (e.g., those set forth above). In some embodiments, an oily suspension comprises an antioxidant (e.g., butylated hydroxyanisol or alpha-tocopherol).

In some embodiments, a pooled composition described herein is formulated for administration by injection, such as, for example, parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered by intraarticular injection. In some embodiments, the pooled composition is administered as a sterile solution, suspension, or emulsion. In some embodiments, the pooled composition is formulated for topical administration, local administration, or inhalation. In some embodiments, bioactive components in the pooled composition disclosed herein, such as for example, HA, nHC-HA/PTX3 and other bioactive components disclosed, diffuse out of the pooled composition and into the surrounding tissue. In some embodiments, the pooled fetal support tissue product formulated for topical administration further comprises a penetration enhancer, a gelling agent, a patch, an adhesive, an emollient, or a combination thereof.

In some embodiments, a formulation for injection is presented in unit dosage form, e.g., in ampoules or in multi-dose containers, with an added preservative.

In some embodiments, a pooled composition described herein is formulated for topical administration. Topical formulations include, but are not limited to, ointments, creams, lotions, solutions, pastes, gels, films, sticks, liposomes, microparticles, microspheres, lipid complexes, nanoparticles. In some embodiments, a topical formulation is administered by use of a patch, bandage, or wound dressing. In some embodiments, the pooled fetal tissue products, compositions, extracts, methods, or devices are formulated for use to treat or prevent, a tissue injury such as for example, an ulcer, wound, perforation, burn, surgery, injury, or fistula. In some embodiments, the method or composition etcetera as disclosed herein prevents or treats, necrosis of the tissue or ischemic conditions. In some embodiments, the ischemic conditions comprise cardiac ischemia, ischemic colitis, mesenteric ischemia, brain ischemia, acute limb ischemia, cyanosis, and gangrene, wherein, the method of treating may comprise contacting an ischemic tissue with a pooled fetal support tissue product disclosed herein. Further provided herein, in some embodiments, are methods of treating a neuropathic condition in an individual in need thereof, comprising contacting an ischemic tissue with a pooled fetal support tissue product.

In some embodiments, a pooled composition described herein is formulated as a composition in the form of a solid, a cross-linked gel, or a liposome. In some embodiments, the fetal tissue support product comprising an nHC-HA/PTX3 complex is formulated as an insoluble cross-linked hydrogel. In some embodiments, the pooled fetal support tissue composition is formulated as a gel or a topical formulation.

In some embodiments, a topical formulation comprises a gelling (or thickening) agent. Suitable gelling agents include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, acacia (gum arabic), agar, aluminum magnesium silicate, sodium alginate, sodium stearate, bladderwrack, bentonite, carbomer, carrageenan, carbopol, xanthan, cellulose, microcrystalline cellulose (MCC), ceratonia, chondrus, dextrose, furcellaran, gelatin, ghatti gum, guar gum, hectorite, lactose, sucrose, maltodextrin, nimannitol, sorbitol, honey, maize starch, wheat starch, rice starch, potato starch, gelatin, sterculia gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), or combinations thereof.

In some embodiments, a topical formulation disclosed herein comprises an emollient. Emollients include, but are not limited to, castor oil esters, cocoa butter esters, safflower oil esters, cottonseed oil esters, corn oil esters, olive oil esters, cod liver oil esters, almond oil esters, avocado oil esters, palm oil esters, sesame oil esters, squalene esters, kikui oil esters, soybean oil esters, acetylated monoglycerides, ethoxylated glyceryl monostearate, hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate, oleyl myristate, oleyl stearate, and oleyl oleate, pelargonic acid, lauric acid, myristic acid, palmitic acid, stearic acid, isostearic acid, hydroxystearic acid, oleic acid, linoleic acid, ricinoleic acid, arachidic acid, behenic acid, erucic acid, lauryl alcohol, myristyl alcohol, cetyl alcohol, hexadecyl alcohol, stearyl alcohol, isostearyl alcohol, hydroxystearyl alcohol, oleyl alcohol, ricinoleyl alcohol, behenyl alcohol, erucyl alcohol, 2-octyl dodecanyl alcohol, lanolin and lanolin derivatives, beeswax, spermaceti, myristyl myristate, stearyl stearate, carnauba wax, candelilla wax, lecithin, and cholesterol.

In some embodiments, a pooled composition described herein is formulated with one or more natural polymers. In some embodiments, a pooled composition described herein is formulated with a natural polymer that is fibronectin, collagen, laminin, keratin, fibrin, fibrinogen, hyaluronic acid, heparan sulfate, chondroitin sulfate. In some embodiments, a pooled composition described herein is formulated with a polymer gel formulated from a natural polymer. In some embodiments, a pooled composition described herein is formulated with a polymer gel formulated from a natural polymer, such as, but not limited to, fibronectin, collagen, laminin, keratin, fibrin, fibrinogen, hyaluronic acid, heparan sulfate, chondroitin sulfate, and combinations thereof.

In some embodiments, pooled fetal support tissue comprises a pharmaceutically acceptable excipient, carrier, or combination thereof. In some embodiments, pooled fetal support tissue is formulated as a non-solid dosage form. In some embodiments, pooled fetal support tissue is formulated as a solid dosage form.

In some embodiments, a pooled composition described herein is formulated for administration to an eye or a tissue related thereto. Formulations suitable for administration to an eye include, but are not limited to, solutions, suspensions (e.g., an aqueous suspension), ointments, gels, creams, liposomes, niosomes, pharmacosomes, nanoparticles, or combinations thereof. In some embodiments, a pooled composition described herein for topical administration to an eye is administered spraying, washing, or combinations thereof. In some embodiments, a pooled composition described herein is administered to an eye via an injectable depot preparation.

As used herein, a "depot preparation" is a controlled-release formulation that is implanted in an eye or a tissue related thereto (e.g., the sclera) (for example subcutaneously, intramuscularly, intravitreally, or within the subconjunctiva). In some embodiments, a depot preparation is formulated by forming microencapsulated matrices (also known as microencapsulated matrices) of a pooled composition described herein in biodegradable polymers. In some embodiments, a depot preparation is formulated by entrapping a pooled composition described herein in liposomes or microemulsions.

A formulation for administration to an eye has an ophthalmologically acceptable tonicity. In certain instances, lacrimal fluid has an isotonicity value equivalent to that of a 0.9% sodium chloride solution. In some embodiments, an isotonicity value from about 0.6% to about 1.8% sodium chloride equivalency is suitable for topical administration to an eye. In some embodiments, a formulation for administration to an eye disclosed herein has an osmolarity from about 200 to about 600 mOsm/L. In some embodiments, a formulation for administration to an eye disclosed herein is hypotonic and thus requires the addition of any suitable substance to attain the proper tonicity range. Ophthalmically acceptable substances that modulate tonicity include, but are not limited to, sodium chloride, potassium chloride, sodium thiosulfate, sodium bisulfite and ammonium sulfate.

A formulation for administration to an eye has an ophthalmologically acceptable clarity. Examples of ophthalmologically-acceptable clarifying agents include, but are not limited to, polysorbate 20, polysorbate 80, or combinations thereof.

In some embodiments, a formulation for administration to an eye comprises an ophthalmologically acceptable viscosity enhancer. In some embodiments, a viscosity enhancer increases the time a formulation disclosed herein remains in an eye. In some embodiments, increasing the time a formulation disclosed herein remains in the eye allows for greater drug absorption and effect. Non-limiting examples of mucoadhesive polymers include carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the composition is formulated for injection into the eye, for example, by injection into a deeper tissue or join space or into a tumor or around a tumor in tissues near the eye and surrounding region. In some embodiments, the composition is administered by intravitreal injection into the eye. In some embodiments, the composition is administered by intraocular injection, subretinal injection, intravitreal injection, periocular administration, subconjunctival injections, retrobulbar injections, intracameral injections (including into the anterior or vitreous chamber), or sub-Tenon's injections. some embodiments, a formulation for administration to an eye is administered or delivered to the posterior segments of an eye (e.g., to the retina, choroid, vitreous and optic nerve). In some embodiments, a topical formulation for administration to an eye disclosed herein for delivery to the posterior of the eye comprises a solubilizing agent, for example, a glucan sulfate and/or a cyclodextrin. Glucan sulfates which are used in some embodiments include, but are not limited to, dextran sulfate, cyclodextrin sulfate and β-1,3-glucan sulfate, both natural and derivatives thereof, or any compound which temporarily binds to and can be retained at tissues which contain fibroblast growth factor (FGF), which improves the stability and/or solubility of a drug, and/or which improves penetration and ophthalmic absorption of a topical formulation for administration to an eye disclosed herein. Cyclodextrin derivatives which are used in some embodiments as a solubilizing agent include, but are not limited to, α-cyclodextrin, β-cyclodextrin, γ-cyclodextrin, hydroxyethyl β-cyclodextrin, hydroxypropyl γ-cyclodextrin, hydroxypropyl β-cyclodextrin, sulfated α-cyclodextrin, sulfated β-cyclodextrin, sulfobutyl ether β-cyclodextrin.

Dosages

The amount of the compositions administered is dependent in part on the individual being treated. In instances where compositions are administered to a human subject, the daily dosage will normally be determined by the prescribing physician with the dosage generally varying according to the age, sex, diet, weight, general health and response of the individual, the severity of the individual's symptoms, the precise disease or condition being treated, the severity of the disease or condition being treated, time of administration, route of administration, the disposition of the composition, rate of excretion, drug combination, and the discretion of the prescribing physician.

In some embodiments, lyophilized and water-soluble forms of the fetal support tissue. Both the powder and liquid forms of the fetal support tissue contain nHC-HA/PTX3 complex. To prepare powder form, fresh or frozen fetal support tissue that has undergone donor eligibility screening is cleaned, cut, soaked, and become a Regulatory Starting Material (RSM). Subsequently, under aseptic, room temperature conditions, the RSM undergoes the processes of lyophilization and micronization, to grind to fine particles (FIG. 1A). In some embodiments, micronization can be performed with or without lyophilization into liquid or powder forms. For powder forms, the micronized fetal support tissue is sieved for particle sizing and following the in-process controls and quality control assessments, become a bulk drug substance that can be packaged, and undergo various terminal sterilization processes to become a finished drug product (FIG. 1B). In some embodiments, the powdered tissue containing nHC-HA/PTX3 can be reconstituted in a suitable excipient, or the powder can be stored frozen at −80° C. In some embodiments, a liquid form of the fetal support tissue is prepared by rehydration after micronization processes. A liquid form of the fetal support tissue can be prepared also following cryopulverization. For example, in order to cryopulverize the fetal support tissue to liquid form, the tissue is processed aseptically at 4° C. conditions (FIG. 2A-2C). The fetal support tissue undergoes cryopulverization, extraction, centrifugation, and filtration. In some embodiments, centrifugation, and filtration of the cryopulverized tissue extract under different various centrifugation and filtration parameters controls particle sizes. In some embodiments, filtration is performed to sterilize the extract (filter pore size of equal to about to less than 0.2 um). Following cryopulverization of the tissue, it is processed as indicated in FIGS. 2A-2C; the tissue composition can be pooled, diluted variously and after in-processing controls are completed, the extract containing nHC-HA/PTX3 is packaged as a finished drug product. In some embodiments, the dosage of an HC-HA/PTX3 complex is between about 0.001 to about 1000 mg/kg body weight/day. In some embodiments, the amount of HC-HA/PTX3 complex disclosed herein is in the range of about 0.5 to about 50 mg/kg/day. In some embodiments, the amount of HC-HA/PTX3 complex disclosed herein is about 0.0001 to about 7 g/day. In some embodiments, the amount of HC-HA/PTX3 complex disclosed herein is about 0.01 to about 7 g/day. In some embodiments, the amount of HC-HA/PTX3 complex disclosed herein is about 0.02 to about 5 g/day. In some embodiments, the amount of HC-HA/PTX3 complex disclosed herein is about 0.05 to about 2.5 g/day. In some embodiments, the amount of HC-HA/PTX3 complex disclosed herein is about 0.1 to about 1 g/day.

In some embodiments, the composition comprising an nHC-HA/PTX3 complex disclosed herein is administered, before, during or after the occurrence of unwanted changes in a tissue. In some embodiments, the nHC-HA/PTX3 composition described herein is administered with a combination therapy before, during or after the occurrence of a disease or condition. In some embodiments, the timing of administering the nHC-HA/PTX3 composition disclosed herein varies. Thus, in some examples, the nHC-HA/PTX3 composition described herein is used as a prophylactic and is administered continuously to subjects with a propensity to develop unwanted changes in a tissue in order to prevent the occurrence of unwanted changes in the tissue. In some embodiments, the nHC-HA/PTX3 composition described herein is administered to a subject during or as soon as possible after the onset of the unwanted changes. In some embodiments, the administration of the nHC-HA/PTX3 composition described herein is initiated within the first 48 hours of the onset of the unwanted changes, preferably within the first 48 hours of the onset of the symptoms, more preferably within the first 6 hours of the onset of the symptoms, and most preferably within 3 hours of the onset of the symptoms. In some embodiments, the initial administration is via any route practical, such as, for example, an intravenous injection, a bolus injection, infusion over 5 minutes to about 5 hours, a pill, a capsule, transdermal patch, buccal delivery, or combination thereof. The nHC-HA/ PTX3 composition described herein is preferably administered as soon as is practicable after the onset of unwanted changes is detected or suspected, and for a length of time necessary for the treatment, such as, for example, from about 1 month to about 3 months. In some embodiments, the length of treatment varies for each subject, and the length is determined using the known criteria. In some embodiments, the composition described herein is administered for at least 2 weeks, preferably about 1 month to about 5 years, and more preferably from about 1 month to about 3 years.

In some embodiments, the nHC-HA/PTX3 composition described herein is administered in a single dose, once daily. In some embodiments, the composition described herein is administered in multiple doses, more than once per day. In some embodiments, the composition described herein is administered twice daily. In some embodiments, the composition described herein is administered three times per day. In some embodiments, the composition described herein is administered four times per day. In some embodiments, the composition described herein comprising nHC-HA/PTX3 complex is administered more than four times per day.

In the case wherein the individual's condition does not improve, upon the doctor's discretion the nHC-HA/PTX3 composition described herein is administered chronically, that is, for an extended period of time, including throughout the duration of the individual's life in order to ameliorate or otherwise control or limit the symptoms of the individual's disease or condition.

In some embodiments, in cases where the individual's status does improve, upon the doctor's discretion, an nHC-HA/PTX3 complex disclosed herein is administered continuously or the dose of drug being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. In some embodiments the dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the individual's condition has occurred, a maintenance dose is administered if necessary. In some embodiments, subsequently, the dosage or the frequency of administration, or both, is reduced, as a function of the symptoms, to a level at which the improved disease, disorder or condition is retained. In some embodiments, individuals require intermittent treatment on a long-term basis upon any recurrence of symptoms.

In some embodiments, the pharmaceutical composition described herein is in unit dosage forms suitable for single administration of precise dosages. In unit dosage form, the formulation is divided into unit doses containing appropriate quantities of an nHC-HA/PTX3 complex disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In some embodiments, multiple dose reclosable containers are used, in which case it is typical to include a preservative in the composition. In some embodiments, formulations for parenteral injection are presented in unit dosage form, which include, but are not limited to ampoules, or in multi dose containers, with an added preservative.

The daily dosages appropriate for an nHC-HA/PTX3 complex disclosed herein are, for example, from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended-release form. Suitable unit dosage forms for oral administration include from about 1 to 50 mg active ingredient. The foregoing ranges are merely suggestive, as the number of variables in regard to an individual treatment regime is large, and considerable excursions from these recommended values are not uncommon. In some embodiments, the dosages are altered depending on a number of variables, not limited to the activity of an nHC-HA/PTX3 complex used, the disease or condition to be treated, the mode of administration, the requirements of the individual subject, the severity of the disease or condition being treated, and the judgment of the practitioner.

In some embodiments, the composition described herein is packaged as articles of manufacture containing packaging material, a pharmaceutical composition which is effective for prophylaxis and/or treating a disease or condition, and a label that indicates that the pharmaceutical composition is to be used for reprogramming a fibroblastic cell in a tissue having unwanted changes due to a disease or condition. In some embodiments, the pharmaceutical compositions are packaged in unit dosage forms contain an amount of the pharmaceutical composition for a single dose or multiple doses. In some embodiments, the packaged compositions contain a lyophilized powder of the pharmaceutical compositions, which is reconstituted (e.g., with water or saline) prior to administration.

Medical Device and Biomaterials Compositions

In some embodiments, the composition described herein is assembled directly on a surface of or formulated as a coating for an implantable medical device. In some embodiments, the composition described herein is assembled directly on a surface of an implantable medical device or a portion thereof.

Exemplary implantable medical devices include, but are not limited to an artificial joint, orthopedic device, bone implant, contact lenses, suture, surgical staple, surgical clip, catheter, angioplasty balloon, sensor, surgical instrument, electrode, needle, syringe, wound drain, shunt, urethral insert, metal or plastic implant, heart valve, artificial organ, lap band, annuloplasty ring, guide wire, K-wire or Denham pin, stent, stent graft, vascular graft, pacemaker, pellets, wafers, medical tubing, infusion sleeve, implantable defibrillator, neurostimulator, glucose sensor, cerebrospinal fluid shunt, implantable drug pump, spinal cage, artificial disc, ocular implant, cochlear implant, breast implant, replacement device for nucleus pulposus, ear tube, intraocular lens, drug delivery system, microparticle, nanoparticle, and microcapsule.

In some embodiments, method of using the composition, product or extract or the composition, product or extract described herein comprising various forms of pooled fetal support tissue reduces pain, reduces bodily inflammation, and reduces scarring. In certain embodiments, such a method of using or such a composition, product or extracts promote regenerative healing. In some embodiments, the regenerative healing includes for example, nerve regeneration, or regeneration of articular cartilage and various bodily regenerative healing. In some embodiments, the nerve regeneration dampens sensitization/stimuli. In some embodiments, disclosed herein can be a method of using a composition, or the composition, product or extract comprising for example, particulate from cryopreserved amniotic membrane (AM) and umbilical cord (UC), wherein the pooled fetal support product, composition, or extract can be used in a variety of clinical applications including for example, knee osteoarthritis, facet osteoarthritis, planter fasciitis, chronic wound healing, complex wound healing, foot pad injury healing.

In some embodiments, a complex wound may be a wound with a chronic bodily ulcer, ischemic wound, or comprise exposed bones, muscle, tendon, join capsule, bone loss (e.g., due to necrosis of soft tissue, bone etc.) and may be difficult to heal increasing susceptible to infection of the skin, muscle, tendon. In some embodiments, the patient with the complex wound may be prone to bone infection including osteomyelitis. In some embodiments, the pooled fetal support tissue extract of the present disclosure may be useful treatment for a complex wound to bring about healing through re-vascularization, re-epithelialization, re-keratinization from the peripheral margins of the wound to the granulation tissue. In some embodiments, the complex wound may be to correct birth defects, such as for example, use of the present disclosure in conducting in-utero spina bifida repair. In still other embodiments, the present disclosure can be useful for the treatment of complex wounds due to diabetes, diabetic neuropathy, e.g., complex gangrene wounds that may require amputation, and, wherein the use of the present disclosure following sharp debridement, bone resection, bone biopsy and/or open cortex etcetera, may eliminate the process of amputation altogether (e.g., amputation of gangrene feet, toes, limbs etcetera).

In some embodiments, the method of using a composition or product or the composition or product comprising for example the particulate from cryopreserved amniotic membrane (AM) and umbilical cord (UC) from pooled fetal support tissue, including for example, clarix flo and cryopreserved AM composition can lead to faster recovery of mechanical hypersensitivity and less heat hypersensitivity. In certain embodiments, a combination of micronized and lyophilized AM and UC can be a pooled fetal support tissue product, composition or extract comprising any sheet and non-sheet form of a fetal support tissue product disclosed herein, and wherein, such a composition or method of using the composition can be used as a medicament, a treatment or any clinical indication disclosed herein. In some embodiments, such a medicament, treatment, or method of using such can be administered for relief of bodily pain, injury, inflammation, scarring, infection, or disease using any method of administering such as disclosed herein. In some embodiments, the composition described herein is assembled directly on a scaffold, a microparticle, a microcapsule or microcarrier employed for the delivery of a biomaterial, such as a stem cell or an insulin producing cell. In some embodiments, the composition described herein is attached to the microcapsule or assembled directly on a microcapsule.

Methods of Use

Disclosed herein, in certain embodiments, are methods of using the compositions described herein by the methods described herein. In some embodiments, the composition comprises a therapeutically effective amount of a pooled composition comprising fetal support tissue. In some embodiments, the composition comprises a therapeutically effective amount of a pooled composition comprising micronized fetal support tissue. In some embodiments, the composition comprises a therapeutically effective amount of a pooled composition comprising morselized fetal support tissue. In some embodiments, the composition comprises a therapeutically effective amount of a pooled composition comprising micronized fetal support tissue. In some embodiments, the fetal support tissue is placental amniotic membrane (PAM), or substantially isolated PAM, umbilical cord amniotic membrane (UCAM) or substantially isolated UCAM, chorion or substantially isolated chorion, amnion-chorion or substantially isolated amnion-chorion, placenta or substantially isolated placenta, umbilical cord or substantially isolated umbilical cord, or any combinations thereof. In some embodiments, the fetal support tissues produced by the methods disclosed herein comprise the fetal support tissue and a pharmaceutically acceptable carrier. In some embodiments, the fetal support tissue products disclosed herein are formulated for administration by topical administration or injection. In some embodiments, the fetal support tissue products disclosed herein are formulated as a solution, suspension, or emulsion.

In some embodiments, a pooled composition disclosed herein is used to inhibit at least one of the following: scarring, inflammation, adhesion, and angiogenesis but promote vasculogenesis. In some embodiments, the pooled fetal support tissue products, such as for example, a product containing isolated nHC-HA/PTX3 composition is used in inhibiting cancer cell regrowth of a tumor, comprising contacting an area surrounding the tumor after a surgical procedure with an isolated nHC-HA/PTX3 complex, thereby inhibiting cancer cell regrowth at the area surrounding the tumor. In some instances, the method of killing cancer cells of a tumor comprises contacting a tumor or an area surrounding the tumor prior to, during or after a surgical procedure with an isolated nHC-HA/PTX3 complex, thereby killing the cancer cells. In some embodiments, pooled composition, product or extract comprising isolated nHC-HA/PTX3 can be utilized to inhibit, treat or as a method for treating or reducing proliferation, cell migration, or epithelial-mesenchymal transition (EMT) of epithelial cells in an individual in need thereof, wherein such a composition or method of treating comprises administering to the individual a therapeutically effective amount the pooled composition or product and a pharmaceutically acceptable diluent, excipient, vehicle, or carrier, thereby preventing or reducing the proliferation, cell migration, or EMT of epithelial cells. In some embodiments, the pooled composition, extract, or product as disclosed, herein in any form, can be administered as treatment, medicament or as a method of inhibiting cancer cell regrowth of a tumor in an individual in need thereof, wherein such treatment, medicament or method of treating comprises contacting an area surrounding the tumor after a surgical procedure with an isolated nHC-HA/PTX3 complex, thereby inhibiting cancer cell regrowth at the area surrounding the tumor.

A method of killing cancer cells of a tumor in an individual in need thereof, comprising contacting a tumor or an area surrounding the tumor prior to, during or after a surgical procedure with an isolated nHC-HA/PTX3 complex, thereby killing the cancer cells.

In some embodiments, the fetal tissue product, composition such as for example, nHC-HA/PTX3 can be used as a bone implant, comprising an outside surface coated with substantially isolated nHC-HA/PTX3 complex.

In some embodiments, a pooled composition disclosed herein can be used to promote wound healing. In some embodiments, the pooled fetal support tissue product, such as for example nHC-HA/PTX3 composition is used to promote vasculogenesis of a tissue comprising endothelial cells and pericytes, comprising reprogramming the pericytes to a first progenitor phenotype by contacting the tissue with a fetal support tissue product and reprogramming the endothelial cells to a second progenitor phenotype by contacting the tissue with the fetal support tissue product. In some embodiments, such healing promoting vasculogenesis involves treating an ischemic tissue comprising endothelial cells and pericytes, comprising reprogramming the pericytes to a first progenitor phenotype by contacting the tissue with a fetal support tissue product and reprogramming the endothelial cells to a second progenitor phenotype by contacting the tissue with the fetal support tissue product. In some embodiments, the use is a pooled use. In some embodiments, the pooled fetal composition disclosed herein can be used to promote nerve regeneration. In some embodiments, the methods disclosed herein comprising use of pooled compositions, extracts or products promote, repair, reconstruct, replace, augment or supplement damaged, or receding soft tissue in a n individual in need thereof. In some embodiment, contacting the damaged or receding soft tissue with said product, extract or composition reduce, or prevent epidural fibrosis, adhesion or scarring following spinal surgery in an individual in need thereof. In some embodiments, the fetal support tissue product can be used in treating a condition or disease, comprising: contacting a fibroblastic cell within a tissue affected by the condition in the subject in need thereof with a composition comprising soluble nHC-HA/PTX3 for a period of time sufficient to reprogram the fibroblastic cell to a cell with a different phenotype, thereby treating the condition or disease. In some embodiments, methods and/or compositions comprising pooled fetal support tissue product disclosed herein inhibit osteoclast differentiation, bone resorption, bone formation, bone remodeling, treatment of alveolar bone degradations, treatment of Paget's disease. In some embodiments, the methods or compositions, devices formulated from pooled fetal support tissue comprising formulations of pooled tissue extracts, products comprising nHC-HA/PTX3 as disclosed herein are formulated and administered for the treatment bone tumor, or for treating a disease disorder or condition defined by deficient or defective bone formation, or for the treatment of osteoporosis, or administration of treatment as an implant, or a patch wherein the patch or implant is placed on an osteolytic bone or an osteolytic joint for an individual in need thereof. In some embodiments, the composition is formulated into an orthopedic prosthesis. In some embodiments, the pooled fetal support tissue products, extracts, compositions, or methods can be administered to promote bone healing, or to inhibit diseases or disorders characterized by bone injury, bone defect, bone deficiency. In some embodiments, a pooled composition disclosed herein is minimally manipulated. In some embodiments, a pooled composition disclosed herein does not comprise another article, except for water, crystalloids, or a sterilizing, preserving, or storage agent. In some embodiments, a pooled composition disclosed herein does not have a systemic effect and is not dependent upon the metabolic activity of living cells for its primary function.

In some embodiments, a pooled composition or product comprises pooled fetal support tissue such as umbilical cord amniotic membrane (UCAM) obtained from fresh, or frozen or previously frozen umbilical cord, and a preservation medium, wherein substantially all of the cells of the UCAM are dead, wherein the UCAM is not dehydrated. In some embodiments, the pooled composition or product from pooled fetal support tissue comprises a method of repairing, reconstructing, replacing, augmenting, or supplementing damaged or receding soft tissue in an individual in need thereof, comprises contacting damaged or receding soft tissue the individual with an umbilical cord product from which water has not been removed.

In some embodiments, pooled fetal support tissue product or composition can be utilized as a method of reducing or preventing epidural fibrosis, adhesion, or scarring following spinal surgery in an individual in need thereof, wherein such a method comprises contacting a spinal surgical site with an umbilical cord product.

In some embodiments, pooled fetal support tissue product can be used as a composition or product or a method for treating an ocular wound or repairing damaged ocular tissue in an individual in need thereof. In some embodiments, the pooled composition, product or extract disclosed herein can be used a medicament, a treatment or a method for treating or preventing Proliferative Vitreoretinopathy (PVR) in an individual having PVR or preventing PVR in an individual who has experienced retinal detachment, comprising administering to the individual having PVR or who has experienced retinal detachment wherein treatment can comprise administering using methods disclosed herein, a substantially isolated native heavy chain-hyaluronic acid/pentraxin 3 complex (HC-HA/PTX3), reconstituted HC-HA/PTX3, or a combination thereof.

In some embodiments, the pooled composition, product, extract disclosed herein can be a medicament, treatment or a method for treating or preventing Proliferative Vitreo-retinopathy (PVR) in an individual having PVR or preventing PVR in an individual who has experienced retinal detachment, where in the pooled product is administered as disclosed herein, to an individual having PVR or who has experienced retinal detachment, wherein a substantially isolated native HC-HA/PTX3 product and an additional therapeutic agent for treating or preventing PVR are provided. In the present disclosure, providing a therapeutically effective amount should be taken to mean any dosage or treatment that will alleviate the condition, provide relief or cure according to any and prevailing procedures or dosages deemed effective for such the treatment, prevention, or relief out of suffering, pain, or condition for which the treatment or prophylaxis is provided.

In some embodiments, a pooled composition disclosed herein is used as a covering (e.g., a wound covering). In some embodiments, the use is a pooled use. In some embodiments, the pooled composition is minimally manipulated. In some embodiments, the pooled composition does not comprise another article, except for water, crystalloids, or a sterilizing, preserving, or storage agent. In some embodiments, the pooled composition does not have a systemic effect and is not dependent upon the metabolic activity of living cells for its primary function.

In some embodiments, a pooled composition disclosed herein is used to promote wound repair. In some embodiments, the use is a pooled use. In some embodiments, the pooled composition is minimally manipulated. In some embodiments, the pooled composition does not comprise another article, except for water, crystalloids, or a sterilizing, preserving, or storage agent. In some embodiments, the pooled composition does not have a systemic effect and is not dependent upon the metabolic activity of living cells for its primary function.

In some embodiments, a pooled composition disclosed herein is used as a barrier to adhesion. In some embodiments, the pooled composition is minimally manipulated. In some embodiments, the pooled composition does not comprise another article, except for water, crystalloids, or a sterilizing, preserving, or storage agent. In some embodiments, the pooled composition does not have a systemic effect and is not dependent upon the metabolic activity of living cells for its primary function.

Injured Tissue Repair and Supplementation

In some embodiments, a pooled composition disclosed herein is used as a wound covering or is used to facilitate wound repair. In some embodiments, the pooled composition is minimally manipulated. In some embodiments, the pooled composition does not comprise another article, except for water, crystalloids, or a sterilizing, preserving, or storage agent. In some embodiments, the pooled composition does not have a systemic effect and is not dependent upon the metabolic activity of living cells for its primary function.

In some embodiments, the tissue was damaged, compromised, or lost due to an injury (e.g., a burn; a surgical incision; an area of necrosis resulting from an infection, trauma, or a toxin; a laceration). In some embodiments, the tissue was damaged, compromised, or lost due to a burn. In some embodiments, the tissue was damaged, compromised, or lost due to a wound (e.g., an incision, laceration, abrasion). In some embodiments, the tissue was damaged, compromised, or lost due to necrosis. In some embodiments, the tissue was damaged, compromised, or lost due to ulceration. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

In some embodiments, a pooled composition disclosed herein comprises HA, nHC-HA/PTX3 complex and a variety of bioactive factors that promote tissue repair, which are found in for example, in the stroma of AM/UC and contain anti-angiogenic and anti-inflammatory proteins. In some embodiments, said HA, nHC-HA/PTX3 complex in a pooled composition disclosed herein diffuse out of the pooled composition and into the surrounding tissue.

Burns

In some embodiments, a pooled composition disclosed herein is applied to a burn. In some embodiments, a pooled composition disclosed herein is applied to a first-degree burn. In some embodiments, a pooled composition disclosed herein is applied to a second-degree burn. In some embodiments, a pooled composition disclosed herein is applied to a third-degree burn. In some embodiments, the pooled composition is applied to a substrate prior to be placed on the burn.

Wounds

In some embodiments, a pooled composition disclosed herein is applied to a wound in the skin (e.g., an incision, laceration, abrasion, ulcer, puncture, penetration). In some embodiments, the pooled composition is applied to a substrate prior to being placed on the wound. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravesical, subconjunctival, intravitreal, epidural, and/or subcutaneous). In some embodiments, the pooled composition is administered epidurally, intrathecally, through inhalation, intravenously, or a combination thereof.

In some embodiments, a pooled composition disclosed herein is applied to an incision in an organ (e.g., the skin, brain, stomach, kidneys, liver, intestines, lungs, bladder, trachea, esophagus, vagina, ureter, and blood vessel walls). In some embodiments, a pooled composition disclosed herein is applied to a surgical incision. In some embodiments, a pooled composition disclosed herein is applied to the site of a colon resection. In some embodiments, a pooled composition disclosed herein is applied to the site of a gastrectomy. In some embodiments, a pooled composition disclosed herein is applied to the site of a breast surgery (e.g., breast reduction surgery, breast augmentation surgery, and mastectomy). In some embodiments, the pooled composition is applied to a substrate prior to being placed on the wound.

In some embodiments, a pooled composition disclosed herein is used as a covering over an incision in the skin (e.g., an incision to the epidermis, dermis, and/or hypodermis). In some embodiments, a pooled composition disclosed herein is used to repair or supplement the skin following hemorrhoid surgery. In some embodiments, the pooled composition is applied to a substrate prior to being placed on the wound.

Necrosis

In some embodiments, a pooled composition disclosed herein is used as a protective graft over an area of necrotic tissue (e.g., from an infection). In some embodiments, a pooled composition disclosed herein is used as a protective graft over an area of necrotic skin. In some embodiments, a pooled composition disclosed herein is placed on an area of necrotic tissue. In some embodiments, the pooled composition is applied to a substrate prior to being placed on the necrotic tissue. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

Ulcer

In some embodiments, a pooled composition disclosed herein is used as a protective covering over an ulcer. In some embodiments, the pooled composition is applied to a substrate prior to being placed on the ulcer. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

In some embodiments, the ulcer is a foot ulcer (e.g., a diabetic foot ulcer or an arterial insufficiency ulcer). In some embodiments, treating a foot ulcer comprises (a) preparing the wound (e.g., debriding the wound); and (b) placing a pooled composition disclosed herein on the wound. In some embodiments, treating a foot ulcer comprises (a) preparing the wound (e.g., debriding the wound); (b) placing a pooled composition disclosed herein on the wound; and (c) covering the pooled composition with a protective barrier (e.g., a silvercell dressing, metipel, gauze, or a bandage). In some embodiments, the pooled composition is applied to a substrate prior to be placed on the ulcer.

In some embodiments, the ulcer is a venous stasis (VS) ulcer. In some embodiments, treating a VS ulcer comprises (a) preparing the wound (e.g., debriding the wound); and (b) placing a pooled composition disclosed herein on the wound. In some embodiments, treating a VS ulcer comprises (a) preparing the wound (e.g., debriding the wound); (b)

placing a pooled composition disclosed herein on the wound; and (c) covering the pooled composition with a protective barrier (e.g., a wound veil, antimicrobial dressing, gauze, or a bandage). In some embodiments, the pooled composition is applied to a substrate prior to being placed on the wound.

In some embodiments, the ulcer is a corneal ulcer (i.e., ulcerative keratitis). In some embodiments, treating a corneal ulcer comprises (a) preparing the wound (e.g., debriding the wound); and (b) placing a pooled composition disclosed herein on the wound. In some embodiments, treating a corneal ulcer comprises (a) preparing the wound (e.g., debriding the wound); (b) placing a pooled composition disclosed herein on the wound; and (c) covering the pooled composition or pooled composition with a protective barrier (e.g., a contact lens or a bandage). In some embodiments, the pooled composition is applied to a substrate prior to being placed on the wound.

Soft Tissue Uses

Disclosed herein, in certain embodiments, is the use of a pooled composition disclosed herein for repairing, reconstructing, replacing, or supplementing a recipient's damaged, compromised, or missing soft tissue (e.g., tendons). In certain embodiments, the pooled composition, product, or extract disclosed herein in a sheet form or non-sheet form, can be used to treat or as a method for reprogramming a cell having a first phenotype, that comprises contacting the cell having the first phenotype with a composition comprising soluble nHC-HA/PTX3 for a time sufficient to reprogram the cell having the first phenotype to a second cell having a second phenotype. In some embodiments, the pooled composition can be used to treat or can be used as a method for treating a condition or disease in a subject in need thereof, that comprises contacting a fibroblastic cell within a tissue affected by the condition in the subject in need thereof with a composition comprising soluble nHC-HA/PTX3 for a period of time sufficient to reprogram the fibroblastic cell to a cell with a different phenotype, thereby treating the condition or disease. In certain embodiments, the pooled composition, extract or product in any form as disclosed herein can be used as a treatment, medicament or as a method for regenerating a tissue that comprises contacting a cell having a first differentiated phenotype with a composition comprising soluble nHC-HA/PTX3 for a time sufficient to reprogram the cell having the first differentiated phenotype to a progenitor cell having a progenitor cell phenotype and differentiating the progenitor cell into a cell having a second differentiated phenotype, thereby regenerating the tissue.

In some embodiments, the use is a pooled use. In some embodiments, the pooled composition is minimally manipulated. In some embodiments, the pooled composition does not comprise another article, except for water, crystalloids, or a sterilizing, preserving, or storage agent. In some embodiments, the pooled composition does not have a systemic effect and is not dependent upon the metabolic activity of living cells for its primary function.

In some embodiments, a pooled composition disclosed herein comprises HA, nHC-HA/PTX3 complex and a variety of bioactive factors that promote tissue repair, which are found in for example, in the stroma of AM/UC and contain anti-angiogenic and anti-inflammatory proteins. In some embodiments, said HA, nHC-HA/PTX3 complex in a pooled composition disclosed herein diffuse out of the pooled composition and into the surrounding tissue.

In some embodiments, a pooled composition disclosed herein described herein is used as a covering over an incision in soft tissue (e.g., eyelids form the tissue plane between different layers of soft tissue). In some embodiments, the pooled composition is applied to a substrate and then used as a covering over an incision in soft tissue (e.g., eyelids form the tissue plane between different layers of soft tissue). In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

In some embodiments, the pooled fetal support tissue composition/extract, methods, kits, devices etcetera disclosed herein is useful treatment or therapeutic for a bladder disorder. In some embodiments, the bladder disorder may be a bladder condition, syndrome, disease, and/or infection. For example, the bladder disorder may be e.g., urinary incontinence. For example, the bladder disorder may be e.g., bladder cancer. In some embodiments, the bladder condition may be associated with cancer or tumor therapy, e.g., therapy for cancer of lower bowel or urinary tract. In some embodiments, the present disclosure may be administered in the bladder soft tissue in patients with interstitial cystitis, overactive bladder, or other neuro-urological dysfunction of the lower urinary tract.

In some embodiments, a pooled composition disclosed herein is used as structural (tectonic) support for soft tissue.

In some embodiments, a pooled composition disclosed herein prevents adhesion in joint or tendon repairs.

In some embodiments, a pooled composition disclosed herein is used in the repair of a tendon or joint (such as rotator cuff repairs, Achilles tendinopathy, and hand tendon repairs). In some embodiments, a pooled composition disclosed herein is used to reinforce a tendon or joint. In some embodiments, a pooled composition disclosed herein is used to prevent adhesion of a healing tendon to surrounding tissue, tendons, or joints. In some embodiments, a pooled composition disclosed herein is used to prevent the formation of scar tissue on a tendon.

In some embodiments, a pooled composition disclosed herein is applied to a substrate and the substrate/pooled composition is used to augment smaller tendons and ligaments of the foot and ankle, including the posterior tibial tendon, the peroneal tendons, the flexor and extensor tendons, and the ligaments of the lateral ankle complex. In some embodiments, a pooled composition disclosed herein is applied to a substrate and the substrate/pooled composition is used to reinforce primary repair of the quadriceps and patellar tendons surrounding the knee. In some embodiments, a pooled composition disclosed herein is applied to a substrate and the substrate/pooled composition is used as a periosteal patch for bone graft in joint replacement. In some embodiments, a pooled composition disclosed herein is applied to a substrate and the substrate/pooled composition is used to augment deficient hip and knee capsular tissue following total joint revision surgery.

In some embodiments, a pooled composition disclosed herein is applied to a substrate and the substrate/pooled composition is used in the repair of a torn rotator cuff. In some embodiments, a pooled composition disclosed herein is applied to a substrate and the substrate/pooled composition is used as a patch over a rotator cuff muscle or tendon (e.g., the supraspinatus tendon). In some embodiments, a pooled composition disclosed herein is applied to a substrate and the substrate/pooled composition is used to reconstruct a rotator cuff muscle or tendon (e.g., the supraspinatus tendon). In some embodiments, a pooled composition disclosed herein is applied to a substrate and the substrate/pooled composition is used to augment a rotator cuff muscle or tendon (e.g., the supraspinatus tendon). In some embodiments, a pooled composition disclosed herein is applied to a substrate and the substrate/pooled composition is used to reinforce a rotator cuff muscle or tendon (e.g., the supraspinatus tendon). In some embodiments, a pooled composition disclosed herein is applied to a substrate and the substrate/pooled composition is used to prevent adhesion of soft tissue to a rotator cuff muscle or tendon (e.g., the supraspinatus tendon).

In some embodiments, a pooled composition disclosed herein is used in the repair gingiva. In some embodiments, a pooled composition disclosed herein is used in the repair gingival recession. In some embodiments, a pooled composition disclosed herein is applied to a substrate and used as a patch over gingiva. In some embodiments, a pooled composition disclosed herein is applied to substrate and used as a patch over an exposed tooth root surface. In some embodiments, a pooled composition disclosed herein is used to reconstruct gingiva. In some embodiments, a pooled composition disclosed herein is used to augment gingiva. In some embodiments, a pooled composition disclosed herein is used to reinforce gingiva. In some embodiments, a pooled composition disclosed herein is used to prevent adhesion of soft tissue to gingiva.

In some embodiments, a pooled composition described herein is applied to a substrate and the substrate/pooled composition is used as a protective graft over an incision or tear in the fascia. In some embodiments, a pooled composition disclosed herein is applied to a substrate and the substrate/pooled composition is used as structural (tectonic) support for the fascia. In some embodiments, a pooled composition disclosed herein is applied to a substrate and the substrate/pooled composition is used as a replacement or supplement for the fascia. In some embodiments, a pooled composition disclosed herein is applied to a substrate and the substrate/pooled composition is used to repair a hernia (e.g., to repair the fascia). In some embodiments, a pooled composition disclosed herein is applied to a substrate and the substrate/pooled composition is used to repair an inguinal hernia. In some embodiments, a pooled composition disclosed herein is applied to a substrate and the substrate/pooled composition is used to repair a femoral hernia. In some embodiments, a pooled composition disclosed herein is applied to a substrate and the substrate/pooled composition is used to repair an umbilical hernia. In some embodiments, a pooled composition disclosed herein is applied to a substrate and the substrate/pooled composition is used to repair an incisional hernia. In some embodiments, a pooled composition disclosed herein is applied to a substrate and the substrate/pooled composition is used to repair a diaphragmatic hernia. In some embodiments, a pooled composition disclosed herein is applied to a substrate and the substrate/pooled composition is used to repair a Cooper's hernia, an epigastric hernia, an hiatal hernia, a Littre's hernia, a lumbar hernia, a maydl hernia, an obturator hernia, a pantaloon hernia, a paraesophageal hernia, a paraumbilical hernia, a perineal hernia, a properitoneal hernia, a Richter's hernia, a sliding hernia, a sciatic hernia, a spigelian hernia, a sports hernia, a Velpeau hernia, or a Amyand's hernia.

In some embodiments, a pooled composition disclosed herein is applied to a substrate and the substrate/pooled composition is used to repair a spinal disc herniation. In some embodiments, a pooled composition disclosed herein is applied to a substrate and the substrate/pooled composition is used as a protective graft over an incision or tear in a spinal disc. In some embodiments, a pooled composition disclosed herein is applied to a substrate and the substrate/pooled composition is used as a protective graft over an incision or tear in an annulus fibrosis. In some embodiments, a pooled composition disclosed herein is applied to a substrate and the substrate/pooled composition is used as structural (tectonic) support for a spinal disc. In some embodiments, a pooled composition disclosed herein is applied to a substrate and the substrate/pooled composition is used as structural (tectonic) support an annulus fibrosis. In some embodiments, a pooled composition disclosed herein is applied to a substrate and the substrate/pooled composition is used as a replacement or supplement for a spinal disc. In some embodiments, a pooled composition disclosed herein is applied to a substrate and the substrate/pooled composition is used as structural (tectonic) support a spinal disc. In some embodiments, a pooled composition disclosed herein is applied to a substrate and the substrate/pooled composition is used as a replacement or supplement for an annulus fibrosis.

In some embodiments, a pooled composition disclosed herein is applied to a substrate and the substrate/pooled composition is used over an incision in the brain, or in one (or all) of the meninges (i.e., the dura mater, the pia mater, and/or the arachnoid mater). In some embodiments, a pooled composition disclosed herein is applied to a substrate and the substrate/pooled composition is used as structural (tectonic) support for one (or all) of the meninges (i.e., the dura mater, the pia mater, and/or the arachnoid mater). In some embodiments, a pooled composition disclosed herein is applied to a substrate and the substrate/pooled composition is used as a replacement for one (or all) of the meninges (i.e., the dura mater, the pia mater, and/or the arachnoid mater).

In some embodiments, a pooled composition disclosed herein is applied to a substrate and the substrate/pooled composition is used over an incision in a lung or in the pleura. In some embodiments, a pooled composition disclosed herein is applied to a substrate and the substrate/pooled composition is used as structural (tectonic) support for the pleura. In some embodiments, a pooled composition disclosed herein is applied to a substrate and the substrate/pooled composition is used as a replacement for the pleura.

In some embodiments, a pooled composition disclosed herein is applied to a substrate and the substrate/pooled composition is used over an incision in a tympanic membrane. In some embodiments, a pooled composition disclosed herein is applied to a substrate and the substrate/pooled composition is used as structural (tectonic) support for a tympanic membrane. In some embodiments, a pooled composition disclosed herein is applied to a substrate and the substrate/pooled composition is used as a replacement for a tympanic membrane.

In some embodiments, a pooled composition disclosed herein is applied to a substrate and the substrate/pooled composition is used as a protective graft over an incision in the heart or the pericardium. In some embodiments, a pooled composition disclosed herein is applied to a substrate and the substrate/pooled composition is used as structural (tectonic) support for the pericardium. In some embodiments, a pooled composition disclosed herein is applied to a substrate and the substrate/pooled composition is used as a replacement for the pericardium.

In some embodiments, a pooled composition disclosed herein is applied to a substrate and the substrate/pooled composition is used as a protective graft over an incision in the peritoneum. In some embodiments, a pooled composition disclosed herein is applied to a substrate and the substrate/pooled composition is used as structural (tectonic) support for the peritoneum. In some embodiments, a pooled composition disclosed herein is applied to a substrate and the substrate/pooled composition is used as a replacement for the peritoneum.

Ophthalmic Uses

Disclosed herein, in certain embodiments, is the use of a pooled composition disclosed herein for repairing, reconstructing, replacing, or supplementing a recipient's damaged, compromised, or missing ocular tissue. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

In some embodiments, the use is a pooled use. In some embodiments, the pooled composition is minimally manipulated. In some embodiments, the pooled composition does not comprise another article, except for water, crystalloids, or a sterilizing, preserving, or storage agent. In some embodiments, the pooled composition disclosed herein does not have a systemic effect and is not dependent upon the metabolic activity of living cells for its primary function.

In some embodiments, a pooled composition disclosed herein comprises HA, nHC-HA/PTX3 complex and a variety of bioactive factors that promote tissue repair, which are found in for example, in the stroma of AM/UC and contain anti-angiogenic and anti-inflammatory proteins. In some embodiments, said HA, nHC-HA/PTX3 complex in a pooled composition disclosed herein diffuse out of the pooled composition and into the surrounding tissue.

Treatment of Glaucoma

As used herein, "Glaucoma" means a disorder characterized by the loss of retinal ganglion cells in the optic nerve. In certain instances, glaucoma partially or fully results from an increase in intraocular pressure in the anterior chamber (AC). Intraocular pressure varies depending on the production of liquid aqueous humor by the ciliary processes of the eye and the drainage of the aqueous humor through the trabecular meshwork.

Glaucoma Drainage Devices (GDD) are medical devices that are implanted into an eye to relieve intraocular pressure by providing an alternative pathway for the aqueous humor to drain. If left uncovered, a GDD tube will erode and leave the eye susceptible to intraocular infection. Thus, the GDD tube needs to be covered. Currently, patches used to cover GDD tubes are made from pericardium, sclera, and cornea. These patches are about 400-550 microns thick. The thinness of these patches results in their melting by 25% in 2 years potentially leaving the shunt tube exposed again.

In some embodiments, a pooled composition disclosed herein is applied to a substrate and the substrate/pooled composition is used to cover GDD tubes. In some embodiments, the substrate/pooled composition is 300-600 microns thick. In some embodiments, the substrate/pooled composition does not melt by 25% in 2 years. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

Treatment of Ocular Ulcers

In some embodiments, a pooled nHC-HA/PTX3 (complex) composition disclosed herein is applied to a substrate and the substrate/pooled composition is used to cover epithelial defects and/or ulcers in eyes. In some embodiments, the pooled composition is administered in patients with defects or ulcers caused by Dry eye, Graft-versus-host disease, Graves' disease, traumatic corneal injuries, corneal surgery, or neurotrophic keratopathy. The present disclosure may be administered in conjunction with a, contact lens such as for example and without limitations, bandage contact lens (BCL) or a scleral lens. The usefulness of combination therapies has been demonstrated, for example, by administration of Clarix/Neox Flo product in conjunction with a BCL has been useful in the treatment of a subject with mild to moderate dry eye disease or in cases where the subject is recalcitrant to standard of care. In such a case, the Flo-BCL combination may be administered for 2 to 3 days. In some embodiments, the present disclosure may be reconstituted in saline and applied within a concave surface of a BCL, this is further administered or applied to the corneal surface of a subject with mild to moderate dry eye disease (e.g., graded as DEWS 1-2 (DEWS—international dry eye workshop) that may manifest superficial corneal epithelial keratopathy and/or remains symptomatic despite standard of care. In some embodiments, the present disclosure may be administered in conjunction with a BCL wherein the BCL can be of a brand that has been approved by an internationally recognized authority such as the United States Federal Drug Administration (FDA). For example, the BCL may be any brand such as for example, ACUVUE OASYS®, AIR OPTIX® NIGHT and DAY® AQUA, Bausch and Lomb PureVision®, Bausch and Lomb PureVision® 2 among other brands. In certain embodiments, the present disclosure reconstituted in saline and applied to the concave surface of the BCL may remain on the corneal surface of the subject for an extended period of not less than 3, 4, 5 days. In certain embodiments, the length of period may be 5 or more days. In some embodiments, the treatment is placed on the corneal of the subject for at least 1, 2, 3, 4 or 5 days. In some embodiments, the fetal support tissue product may comprise morselized product that may be a product or composition comprising pooled or non-pooled fetal support tissue. For example, the morselized product may comprise, for example, a pooled fetal support tissue comprising amniotic membrane and umbilical cord tissue which has been morselized, centrifuges, sterile filtered fetal support tissue product/extract or composition (morselized product or TTBT01 drug product, hereinafter). In some embodiments, the TTBT01 drug product may comprise fetal support tissue from a plurality of donors and/or donor lots. In some embodiments, the TTBT01 drug product may comprise fetal support tissue from multiple donors and/or donor lots. In some embodiments, the TTB01 drug product or morselized product may be packaged in a single use unit dose vial. In some embodiments, the TTBT01 drug product or morselized product may be topically applied to the ocular surface in the concave bowl of a PROSE or BostonSight SCLERAL lens in subjects with DEWS grade 3-4 severe dry eye. The PROSE and BostonSight SCLERAL lens are class II FDA 510(k)-cleared medical devices. Such a product that combines TTBT01 with a scleral lens of choice may be administered to a subject as prescribed in the user guide. For example, TTBT01 may be filled within the scleral lens on a daily-basis and applied to the eye for at least 4 hours. In some embodiments, the TTBT01 drug product may be filled within the scleral lens every 1, 2 or more days and applied within the eye for the length of time as prescribed by a trained ophthalmologist or trained medical personnel (physician). Administration of the TTBT01 drug product to the scleral lens and application to the eye may be performed consistently for best results, for the duration of treatment, e.g., may be administered daily for 5-7 days. In other cases, the administration may be for less than 5 days or more than 7 days. In general, the drug product in the sclera lens may be reconstituted daily and administered as such or as determined by the physician and the response of the subject being treated. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof. In some embodiments, the substrate is a bandage contact lens or scleral lens.

In some embodiments, the base of the ulcer is debrided with surgical sponges and the poorly adherent epithelium adjacent to the edge of the ulcer is removed (e.g., to the section of the eye where the epithelium becomes quite adherent). In some embodiments, a pooled composition disclosed herein is applied to a substrate and the substrate/pooled composition is transferred to the recipient eye. In some embodiments, a pooled composition disclosed herein is applied to a substrate and the substrate/pooled composition is then secured to the eye by sutures (e.g., interrupted 10-0 nylon sutures or running 10-0 nylon sutures) with the suture knots being buried. In some embodiments, a pooled composition disclosed herein is applied to a substrate and the substrate/pooled composition is secured to the eye by use of fibrin glue. In some embodiments, a protective layer is applied over the pooled composition/substrate or the entire eye (e.g., a contact lens). In some embodiments, the substrate/pooled composition further comprises an antibiotic (e.g., neomycin, polymyxin b sulfate and dexamethasone).

In some embodiments, a pooled composition disclosed herein is applied to a substrate and the substrate/pooled composition is used in conjunctival, scleral, lid, and orbital rim surface reconstruction. In some embodiments, damage to the conjunctival surface results from symblepharon lysis; surgical removal of tumor, lesion, and/or scar tissue; excimer laser photorefractive keratectomy and therapeutic keratectomy; or combinations thereof.

Coronary Uses

Disclosed herein, in certain embodiments, is the use of a pooled nHC-HA/PTX3 (complex) composition disclosed herein for repairing, reconstructing, replacing, or supplementing a recipient's damaged, compromised, or missing coronary tissue. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

In some embodiments, the use is a pooled use. In some embodiments, the pooled composition is minimally manipulated. In some embodiments, the AM does not comprise another article, except for water, crystalloids, or a sterilizing, preserving, or storage agent. In some embodiments, the pooled composition does not have a systemic effect and is not dependent upon the metabolic activity of living cells for its primary function.

In some embodiments, a pooled composition disclosed herein comprises HA, nHC-HA/PTX3 complex and a variety of bioactive factors that promote tissue repair, which are found in for example, in the stroma of AM/UC and contain anti-angiogenic and anti-inflammatory proteins. In some embodiments, said HA, nHC-HA/PTX3 complex in a pooled composition disclosed herein diffuse out of the pooled composition and into the surrounding tissue.

Coronary Artery Bypass

Disclosed herein, is the use of a pooled nHC-HA/PTX3 (complex) composition described herein in coronary artery bypass surgery. In some embodiments, a pooled composition disclosed herein is applied to a substrate and the substrate/pooled composition is grafted onto a coronary artery to bypass a section of the artery that is characterized by atherosclerosis. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

Heart Valves

In some embodiments, a pooled nHC-HA/PTX3 (complex) composition disclosed herein is applied to a substrate and the substrate/pooled composition is applied over a heart valve. In some embodiments, a pooled composition disclosed herein is applied to a substrate and the substrate/pooled composition is used as structural (tectonic) support for a heart valve. In some embodiments, a pooled composition disclosed herein is applied to a substrate and the substrate/pooled composition is used as a replacement for a heart valve. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

Veins and Arteries

In some embodiments, a pooled nHC-HA/PTX3 (complex) composition disclosed herein is applied to a vein or artery. In some embodiments, a pooled nHC-HA/PTX3 (complex) composition disclosed herein is applied to a substrate and the substrate/pooled composition is applied to a vein or artery. In some embodiments, a pooled composition disclosed herein is applied to a substrate and the substrate/pooled composition is used as structural (tectonic) support for a vein or artery. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

Nerve Uses

In some embodiments, a pooled nHC-HA/PTX3 (complex) composition disclosed herein is applied to a nerve or nerve tissue. In some embodiments, a pooled nHC-HA/PTX3 (complex) composition disclosed herein is applied to a substrate and the substrate/pooled composition is used as a covering over a nerve (e.g., a peripheral nerve). In some embodiments, a pooled composition disclosed herein is applied to a substrate and the substrate/pooled composition is used as a covering over a nerve graft, nerve transfer, or a repaired nerve. In some embodiments, a pooled composition disclosed herein is applied to a substrate and the substrate/pooled composition is used as a covering over an incision in a nerve (e.g., a peripheral nerve). In some embodiments, a pooled composition disclosed herein is applied to a substrate and the substrate/pooled composition is used as structural (tectonic) support for a nerve (e.g., a peripheral nerve). In some embodiments, a pooled composition disclosed herein prevents adhesion in nerve repair.

Disclosed herein, in certain embodiments, is the use of a pooled nHC-HA/PTX3 (complex) composition for repairing, reconstructing, replacing, or supplementing a recipient's damaged, compromised, or missing nerve tissue. Various diseases are associated with nerve pain or injury to the nerve. Not in any way limiting, exemplary conditions associated with nerve pain include pain to the musculoskeletal system, or pain to the locomotor system of mammals which may comprise bones, muscles, and connective tissues, can include tendons, cartilage, ligaments. Musculoskeletal pain can result from injuries that are short lived or lifelong conditions or conditions that may cause ongoing functioning limitations, disability, and pain from for example, strains, repetitive overuse, sprains, dislocations, fractures or malformations of the bones, or joints that may comprise scoliosis, a curvature of the spine or a combination thereof. In some embodiments, musculoskeletal conditions can affect joints to include conditions such as for example, conditions comprising osteoarthritis, rheumatoid arthritis, psoriatic arthritis, gout, ankylosing spondylitis. In some embodiments, musculoskeletal conditions may affect bones to include conditions for example, such as osteoporosis, osteopenia and associated fragility fractures, traumatic fractures, amputations. In some embodiments, musculoskeletal conditions may affect muscles, for example, sarcopenia, or the spin such as for example, back and neck pain. In some embodiments, musculoskeletal pain or conditions may affect multiple body areas, or body systems and may result in for example, regional bodily or system pain, widespread pain disorders, inflammatory diseases comprising connective tissue diseases and vasculitis comprising systemic lupus erythematosus, bursitis among other conditions that may results from pain, infection, or injury to the musculoskeletal system. In some embodiments, the pooled composition is administered to treat the condition comprising nerve pain such as musculoskeletal pain.

In some embodiments, the pooled nHC-HA/PTX3 (complex) composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

In some embodiments, the use is a pooled use. In some embodiments, the pooled composition is minimally manipulated. In some embodiments, the pooled composition does not comprise another article, except for water, crystalloids, or a sterilizing, preserving, or storage agent. In some embodiments, the pooled composition does not have a systemic effect and is not dependent upon the metabolic activity of living cells for its primary function.

Disclosed herein are processes for generating fetal support tissue while preserving the biological activity of the fetal support tissue, including components of the fetal support tissue, such as for example, HA, HC-HA/PTX3 growth factors, cytokines, and other active biological components, of which the potency of HC-HA/PTX3 can be monitored to ensure its adequate preservation as disclosed throughout the specification and claims. In some embodiments, the nHC-HC/PTX3 and other biologically active components found in a pooled composition disclosed herein diffuse out of the pooled composition and into the surrounding tissue.

In some embodiments, a pooled nHC-HA/PTX3 (complex) composition disclosed herein is applied to a substrate and the substrate/pooled composition is used as a non-constricting encasement for injured nerves. In some embodiments, a pooled composition described herein prevents or minimizes scar formation, encapsulation, chronic compression, tethering of a nerve, and nerve entrapment. In some embodiments, a pooled composition described herein prevents or minimizes neuroma formation. In some embodiments, a pooled composition described herein prevents or minimizes the migration of endogenous growth factors (e.g., Nerve Growth Factor) present during nerve repair.

Spinal Uses

Disclosed herein, in certain embodiments, is the use of a pooled composition described herein during spinal surgery.

In some embodiments, a pooled composition described herein is used during a laminectomy. In some embodiments, the use is a pooled use. In some embodiments, the pooled composition is minimally manipulated. In some embodiments, the pooled composition does not comprise another article, except for water, crystalloids, or a sterilizing, preserving, or storage agent. In some embodiments, the pooled composition does not have a systemic effect and is not dependent upon the metabolic activity of living cells for its primary function.

In some embodiments, a pooled composition disclosed herein comprises HA, nHC-HA/PTX3 complex and a variety of bioactive factors that promote tissue repair, which are found in for example, in the stroma of AM/UC and contain anti-angiogenic and anti-inflammatory proteins. In some embodiments, said HA, nHC-HA/PTX3 complex in a pooled composition disclosed herein diffuse out of the pooled composition and into the surrounding tissue. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

In some embodiments, a pooled composition described herein is used to reduce or prevent epidural fibrosis and/or scar adhesions following spinal surgery (e.g., laminectomy). In some embodiments, a pooled composition described herein is implanted between dura mater and overlying tissue following spinal surgery (e.g., laminectomy). In some embodiments, implanting a pooled composition described herein between dura mater and overlying tissue following spinal surgery (e.g., laminectomy) reduces or prevents migration of fibroblasts to the dura mater and collagen deposition on the dura mater.

In some embodiments, a pooled composition described herein is used to reduce or prevent the development of proliferative scarring following spinal surgery (e.g., laminectomy). In some embodiments, a pooled composition described herein is used to reduce or prevent the development of a postoperative (e.g., post-laminectomy) epidural/peridural/perineural scar. In some embodiments, a pooled composition described herein is used to reduce or prevent the development of proliferative scarring following spinal surgery (e.g., laminectomy). In some embodiments, a pooled composition disclosed herein is used to reduce or prevent the development of a postlaminectomy membrane.

In some embodiments, a pooled composition described herein is used to reduce or prevent the development of extradural compression or dural tethering following spinal surgery (e.g., laminectomy). In some embodiments, a pooled composition described herein is used to reduce or prevent the development of tethered nerve roots following spinal surgery (e.g., laminectomy). In some embodiments, a pooled composition described herein is used to reduce or prevent the development of arachnoiditis following spinal surgery (e.g., laminectomy).

In some embodiments, a pooled composition disclosed herein further comprises morselized bone tissue. In some embodiments, a pooled composition disclosed herein comprising morselized bone tissue is used during a spinal fusion procedure. In some embodiments, a pooled composition disclosed herein comprising morselized bone tissue is implanted between adjacent vertebrae. In some embodiments, implantation of a pooled composition disclosed herein comprising morselized bone tissue between two adjacent vertebrae promotes fusion of the vertebrae.

In some embodiments, a pooled composition disclosed herein is used as a protective graft over an incision in the dura mater. In some embodiments, a pooled composition disclosed herein is applied to a substrate and the substrate/pooled composition is used as structural (tectonic) support for the dura mater. In some embodiments, a pooled composition disclosed herein is applied to a substrate and the substrate/pooled composition is used as a replacement for the dura mater.

Other Uses of a Pooled Composition

In some embodiments, a pooled nHC-HA/PTX3 (complex) composition disclosed herein is applied to a patch or wound dressing. In some embodiments, the pooled composition is administered by parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural, and/or subcutaneous). In some embodiments, the pooled composition is administered epidurally, intrathecally, through inhalation, intravenously, or a combination thereof.

In some embodiments, a pooled composition disclosed herein is used as a dermal filler. In some embodiments, a pooled composition disclosed herein is injected into subdermal facial tissues. In some embodiments, a pooled composition disclosed herein is injected under wrinkles and aging lines of the face (e.g., nasolabial folds, melomental folds, "crow's feet" and forehead wrinkles). In some embodiments, a pooled composition disclosed herein is used for lip augmentation. In some embodiments, a pooled composition disclosed herein is injected into the lips. In some embodiments, a pooled composition disclosed herein is applied after or in conjunction with skin rejuvenation therapy such as laser ablation therapy.

In some embodiments, a pooled composition disclosed herein is used to treat arthritis (e.g., osteoarthritis, rheumatoid arthritis, septic arthritis, ankylosing spondylitis, spondylosis). In some embodiments, a pooled composition disclosed herein is injected into an arthritic joint (e.g., a knee).

In some embodiments, a pooled nHC-HA/PTX3 (complex) composition disclosed herein is used to inhibit bone resorption in an individual in need thereof. In some embodiments, the individual has arthritis, osteoporosis, alveolar bone degradation, Paget's disease, or a bone tumor. In some embodiments, the pooled composition is injected into a joint. In some embodiments, the pooled composition is contacted with a bone (e.g., by use of a wound dressing or bandage). In some embodiments, the pooled composition coats a bone stent, bone implant, or bone prosthesis (e.g., an osseointegrated implant). As used herein, an "osseointegrated implant" means a three-dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pooled composition disclosed herein is used to promote or induce bone formation in an individual in need thereof in an individual in need thereof. In some embodiments, the individual has arthritis, osteoporosis, alveolar bone degradation, Paget's disease, or a bone tumor. In some embodiments, the pooled composition is injected into a joint. In some embodiments, the pooled composition is contacted with a bone (e.g., by use of a wound dressing or bandage). In some embodiments, the pooled composition coats a bone stent, bone implant, or bone prosthesis (e.g., an osseointegrated implant). As used herein, an "osseointegrated implant" means a three-dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pooled composition disclosed herein is used to inhibit osteoclast differentiation. In some embodiments, the individual has arthritis, osteoporosis, alveolar bone degradation, Paget's disease, or a bone tumor. In some embodiments, the pooled composition is injected into a joint. In some embodiments, the pooled composition is contacted with a bone (e.g., by use of a wound dressing or bandage). In some embodiments, the pooled composition coats a bone stent, bone implant, or bone prosthesis (e.g., an osseointegrated implant). As used herein, an "osseointegrated implant" means a three-dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent is in placed in a knee or joint. In some embodiments, the bone stent is placed in a bone fracture. In some embodiments, the bone stent is expandable or contractible.

In some embodiments, a pooled composition disclosed herein is used to promote mineralization by osteoblasts in an individual in need thereof. In some embodiments, the individual has arthritis, osteoporosis, alveolar bone degradation, Paget's disease, or a bone tumor. In some embodiments, the pooled composition is injected into a joint. In some embodiments, the pooled composition is contacted with a bone (e.g., by use of a wound dressing or bandage). In some embodiments, the pooled composition coats a bone stent, bone implant, or bone prosthesis (e.g., an osseointegrated implant). As used herein, an "osseointegrated implant" means a three-dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pooled composition disclosed herein is used to balance bone resorption and bone formation in an individual in need thereof. In some embodiments, the individual has arthritis, osteoporosis, alveolar bone degradation, Paget's disease, or a bone tumor. In some embodiments, the pooled composition is injected into a joint. In some embodiments, the pooled composition is contacted with a bone (e.g., by use of a wound dressing or bandage). In some embodiments, the pooled composition coats a bone stent, bone implant, or bone prosthesis (e.g., an osseointegrated implant). As used herein, an "osseointegrated implant" means a three-dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pooled composition disclosed herein is used to treat an orthodontic or a periodontal condition. In some embodiments, the periodontal condition is selected from gingivitis, gingival recession, or periodontitis. In some embodiments, a pooled composition disclosed herein is used as an anti-inflammatory or used to promote osteointegration or healing. In some embodiments, a pooled composition disclosed herein is used in combination with a dental implant to promote implant osteointegration, anti-inflammation, and healing.

In some embodiments, a pooled composition disclosed herein to treat hoarseness or voice disorders. In some embodiments, a pooled composition disclosed herein is used for injection laryngoplasty to repair vocal cords.

In some embodiments, a pooled composition disclosed herein is coated onto a medical implant (e.g., a stent). In some embodiments, a medical implant/pooled composition disclosed herein is implanted into an individual in need thereof, wherein the pooled composition is partially or fully released into the individual. In some embodiments, the medical implant is a stent (e.g., a bone stent or a coronary stent). In some embodiments, the medical implant is a bone stent. In some embodiments, the medical implant is a coronary stent.

Combination Treatments

In some embodiments, the nHC-HA/PTX3 (complex) compositions and methods described herein are used in conjunction with other well-known therapeutic reagents that are selected for their particular usefulness against the condition that is being treated. In general, the compositions described herein and, in embodiments where combinational therapy is employed, other agents do not have to be administered in the same composition, and may, because of different physical and chemical characteristics, have to be administered by different routes. The determination of the mode of administration and the advisability of administration, where possible, in the same composition, is well within the knowledge of the skilled clinician. The initial administration can be made according to established protocols known in the art, and then, based upon the observed effects, the dosage, modes of administration and times of administration can be modified by the skilled clinician.

The particular choice of the nHC-HA/PTX3 (complex) compounds used will depend upon the diagnosis of the attending physicians and their judgment of the condition of the patient and the appropriate treatment protocol. In some embodiments, the compounds are administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically effective dosages can vary when the drugs are used in treatment combinations. Methods for experimentally determining therapeutically effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, in some embodiments, when co-administered with one or more biologically active agents, the compound provided herein is administered either simultaneously with the biologically active agent(s), or sequentially. If administered sequentially, the attending physician will decide on the appropriate sequence of administering protein in combination with the biologically active agent(s).

In some embodiments, multiple therapeutic agents are administered in any order, or even simultaneously. If simultaneously, in some embodiments, the multiple therapeutic agents are provided in a single, unified form, or in multiple forms (by way of example only, either as a single pill or as two separate pills). In some embodiments, one of the therapeutic agents is given in multiple doses, or both are given as multiple doses. If not simultaneous, in some embodiments, the timing between the multiple doses varies from more than zero weeks to less than four weeks. In addition, the combination methods, compositions, and formulations are not to be limited to the use of only two agents; the use of multiple therapeutic combinations are also envisioned.

It is understood that the dosage regimen to treat or ameliorate the condition(s) for which relief is sought, can be modified in accordance with a variety of factors. These factors include the disorder from which the subject suffers, as well as the age, weight, sex, diet, and medical condition of the subject. Thus, the dosage regimen employed can vary widely and therefore can deviate from the dosage regimens set forth herein.

Kits/Articles of Manufacture

For use in the therapeutic applications of nHC-HA/PTX3 (complex) described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, bottles, and any packaging material suitable for a selected formulation and intended mode of administration and treatment. A wide array of formulations of the compounds and compositions provided herein are contemplated as are a variety of treatments for any disease, disorder, or condition.

For example, the container(s) can include one or more UCAM, or nHC-HA/PTX3 (complex) compositions described herein, optionally in a composition or in combination with another agent as disclosed herein. The container(s) optionally has a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of the compositions described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded, or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the nHC-HA/PTX3 (complex) compositions can be presented in a pack or dispenser device which can contain one or more-unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible 1 carrier can also be prepared, placed in an appropriate container, and labeled for treatment of an indicated condition.

EMBODIMENTS

Embodiment 1. A composition comprising, pooled fetal support tissue, wherein the pooled fetal support tissue comprises a therapeutically effective amount of native HC-HA/PTX3 complex.

Embodiment 2. The composition of embodiment 1, wherein the pooled fetal support tissue increases uniformity of the native HC-HA/PTX3 complex in the composition.

Embodiment 3. The composition of embodiment 1 or 2, wherein the pooled fetal support tissue comprises fetal support tissue from a plurality of donors.

Embodiment 4. The composition of embodiment 1 or 2, wherein the pooled fetal support tissue comprises fetal support tissue from at least three donors.

Embodiment 5. The composition of embodiment 1 or 2, wherein the pooled fetal support tissue comprises fetal support tissue from at least five donors.

Embodiment 6. The composition of embodiment 1 or 2, wherein the pooled fetal support tissue comprises fetal support tissue from at least ten donors.

Embodiment 7. The composition of any one of embodiment 1 to 6, wherein the composition exhibits a therapeutic potency as determined by an assay comprising one or more of an HA content assay, PTX3 content assay, BCA total protein assay, an ODI-TRAP assay, an M2 polarization assay, or a WST-1 assay.

Embodiment 8. The composition of embodiment 7, wherein the therapeutic potency is determined by the ODI-TRAP assay.

Embodiment 9. The composition of embodiment 8, wherein the composition exhibits a statistically significant inhibition of TRAP activity compared to a positive control in the ODI-TRAP assay when an HA content of the composition is at least 200 µg/ml, 250 µg/ml, 300 µg/ml, 400 µg/ml, 500 µg/ml, 600 µg/ml, 700 µg/ml, 800 µg/ml, 900 µg/ml, 1,000 µg/ml.

Embodiment 10. The composition of embodiment 9, wherein the significant inhibition of TRAP activity is at least 70% inhibition of TRAP activity.

Embodiment 11. The composition of embodiment 9, wherein the significant inhibition of TRAP activity is at least 80% inhibition of TRAP activity.

Embodiment 12. The composition of embodiment 9, wherein the significant inhibition of TRAP activity is at least 85% inhibition of TRAP activity.

Embodiment 13. The composition of any one of embodiments 9 to 12, wherein the HA content of the composition is at least 200 µg/ml Embodiment 14. The composition of any one of embodiments 9 to 12, wherein the HA content of the composition is at least 250 µg/ml.

Embodiment 15. The composition of any one of embodiments 9 to 12, wherein the HA content of the composition is at least 300 µg/ml.

Embodiment 16. The composition of any one of embodiments 9 to 12, wherein the HA content of the composition is at least 350 µg/ml.

Embodiment 17. The composition of any one of embodiments 9 to 12, wherein the HA content of the composition is about 300 µg/ml.

Embodiment 18. The composition of embodiment 9, wherein the positive control is RANKL treatment.

Embodiment 19. The composition of embodiment 7, wherein the therapeutic potency is determined by the M2 assay.

Embodiment 20. The composition of embodiment 7, wherein the therapeutic potency is determined by the NO assay.

Embodiment 21. The composition of embodiment 7, wherein the therapeutic potency is determined by the WST-1 assay.

Embodiment 22. The composition of embodiment 7, wherein the therapeutic potency is determined by the BCA protein assay.

Embodiment 23. The composition of embodiment 7, wherein the therapeutic potency is determined by the HA content assay.

Embodiment 24. The composition of any one of embodiments 1 to 23, wherein an HA content of the composition is at least 75 µg/ml.

Embodiment 25. The composition of any one of embodiments 1 to 24, wherein an HA content of the composition is at least 90 µg/ml.

Embodiment 26. The composition of any one of embodiments 1 to 25, wherein a total protein content of the composition is at least 250 µg/ml.

Embodiment 27. The composition of any one of embodiments 1 to 26, wherein the pooled fetal support tissue is lyophilized.

Embodiment 28. The composition of any one of embodiments 1 to 27, wherein the pooled fetal support tissue is lyophilized prior to pooling the fetal support tissue.

Embodiment 29. The composition of any one of embodiments 1 to 28, wherein the pooled fetal support tissue is lyophilized after pooling the fetal support tissue.

Embodiment 30. The composition of any one of embodiments 1 to 29, wherein the pooled fetal support tissue composition is previously frozen or cryopreserved.

Embodiment 31. The composition of any one of embodiments 1 to 30, wherein the pooled fetal support tissue comprises a particle size of about 0.01 micrometer (µm) to about 240 µm in diameter.

Embodiment 32. The composition of any one of embodiments 1 to 30, wherein the pooled fetal support tissue comprises an average particle size of about 0.5 µm.

Embodiment 33. The composition of any one of embodiments 1 to 32, wherein the pooled fetal support tissue comprises placenta, umbilical cord, placental amniotic membrane umbilical cord amniotic membrane, Wharton's jelly, chorion, or amnion-chorion, or any combination thereof.

Embodiment 34. The composition of any one of embodiments 1 to 32, wherein the pooled fetal support tissue comprises placental amniotic membrane, umbilical cord, or both.

Embodiment 35. The composition of any one of embodiments 1 to 34, wherein the pooled fetal support tissue is pulverized before pooling.

Embodiment 36. The composition of any one of embodiments 1 to 34, wherein the pooled fetal support tissue is pulverized after pooling.

Embodiment 37. The composition of any one of embodiments 1 to 34, wherein the pooled fetal support tissue is morselized.

Embodiment 38. The composition of any one of embodiments 1 to 34, wherein the pooled composition is filtered or ultra-filtered.

Embodiment 39. The composition of any one of embodiments 1 to 34, wherein the pooled fetal support tissue is decellularized.

Embodiment 40. The composition of any one of embodiments 1 to 38, wherein the pooled fetal support tissue is devitalized.

Embodiment 41. The composition of any one of embodiments 1 to 40, wherein the pooled fetal support tissue is a gel extract.

Embodiment 42. The composition of any one of embodiments 1 to 40, wherein the pooled fetal support tissue is powdered.

Embodiment 43. The composition of any one of embodiments 1 to 42, wherein the pooled fetal support tissue comprises 5% water by weight or more.

Embodiment 44. The composition of any one of embodiments 1 to 43, wherein the pooled fetal support tissue comprises at most 15% water by weight.

Embodiment 45. The composition of any one of embodiments 1 to 44, wherein the pooled fetal support tissue is obtained from a frozen or previously frozen fetal support tissue.

Embodiment 46. The composition of any one of embodiments 1 to 45, wherein the pooled fetal support tissue is substantially free of a vein or artery.

Embodiment 47. The composition of any one of embodiments 1 to 46, wherein substantially all cells of the pooled fetal support tissue are dead.

Embodiment 48. The composition of any one of embodiments 1 to 47, wherein the pooled fetal support tissue is terminally sterilized, gamma irradiated, filtered, electron beam sterilized or a combination thereof.

Embodiment 49. The composition of any one of embodiments 1 to 48, wherein the composition is provided as a pharmaceutical composition and further comprises a pharmaceutically acceptable excipient.

Embodiment 50. The composition of embodiment 49, wherein the pharmaceutically acceptable excipient is normal saline.

Embodiment 51. The composition of any one of embodiments 1 to 50, wherein the pooled fetal support tissue composition exhibits reduced variation of activity of native HC-HA/PTX3 complex compared to a non-pooled fetal support tissue composition as determined by an ODI-TRAP assay, BCA assay or HA quantitative assay.

Embodiment 52. The composition of embodiment 51, wherein the reduced variation is a coefficient of variation of 10% or less.

Embodiment 53. The composition of embodiment 51, wherein the reduced variation is a coefficient of variation of 5% or less.

Embodiment 54. The composition of embodiment 51, wherein the reduced variation is a coefficient of variation of 4% or less.

Embodiment 55. The composition of embodiment 51, wherein the reduced variation is a coefficient of variation of about 3%.

Embodiment 56. The composition of embodiment 51, wherein the reduced variation is a coefficient of variation of about 2% or less.

Embodiment 57. A method of treating a degenerative disease in an individual, the method comprising administering the pooled fetal support tissue of any one of embodiments 1 to 56 to the individual.

Embodiment 58. A method of treating inflammation in an individual, the method comprising administering the pooled fetal support tissue of any one of embodiments 1 to 56 to the individual.

Embodiment 59. A method of promoting wound healing in an individual, the method comprising administering the pooled fetal support tissue of any one of embodiments 1 to 56 to the individual.

Embodiment 60. A method of treating osteoarthritis in an individual, the method comprising administering the pooled fetal support tissue of any one of embodiments 1 to 56 to the individual.

Embodiment 61. The method of embodiment 60, wherein the osteoarthritis is of the knee.

Embodiment 62. A method of making the composition of any one of embodiments 1 to 56, comprising obtaining fetal support tissue from a plurality of donors and pooling the fetal support tissue from the plurality of donors.

Embodiment 63. The method of embodiment 62, wherein the fetal support tissue from the plurality of donors is lyophilized prior to the pooling.

Embodiment 64. The method of embodiment 63 wherein the fetal support tissue from the plurality of donors is lyophilized after the pooling.

Embodiment 65. The method of any one of embodiments 62 to 64, further comprising processing the fetal support tissue from the plurality of donors by morselizing, pulverizing, micronizing, or a combination thereof.

Embodiment 66. The method of any one of embodiments 62 to 65, further comprising devitalizing the fetal support tissue from the plurality of donors.

Embodiment 67. The method of any one of embodiments 62 to 65, further comprising decellularizing the fetal support tissue from the plurality of donors.

Embodiment 68. The method of any one of embodiments 62 to 67, wherein the fetal support tissue from the plurality of donors is not dehydrated.

Embodiment 69. The method of any one of embodiments 62 to 68, wherein the fetal support tissue from the plurality of donors is not dehydrated to comprise less than 20% water by weight.

Embodiment 70. The method of any one of embodiments 62 to 68, wherein the fetal support tissue from the plurality of donors is not dehydrated to comprise less than 15% water by weight.

Embodiment 71. A method of validating a pooled fetal support tissue product the method comprising conducting a validation assay on the pooled fetal support tissue, wherein the validation assay determines an amount and/or therapeutic potency of native HC-HA/PTX3 complex.

Embodiment 72. The method of embodiment 71, wherein the native HC-HA/PTX3 is therapeutically active.

Embodiment 73. The method of embodiment 71, wherein the validation assay comprises one or more of an HA content assay, a PTX3 content assay, an ODI-TRAP assay, BCA protein assay, an M2 polarization assay, NO assay, or a WST-1 assay.

Embodiment 74. The method of embodiment 71 or 73, wherein the validation assay comprises the ODI-TRAP assay.

Embodiment 75. The method of embodiment 74, wherein the pooled fetal support tissue product exhibits a statistically significant inhibition of TRAP activity compared to a positive control in the ODI-TRAP assay when an HA content of the composition is at least 200 μg/ml, 250 μg/ml, 300 μg/ml, 400 μg/ml, 500 μg/ml, 600 μg/ml, 700 μg/ml, 800 μg/ml, 900 μg/ml, 1,000 μg/ml.

Embodiment 76 comprises the method of embodiment 75, wherein the positive control is RANKL treatment.

Embodiment 77. The method of embodiment 71, wherein the therapeutic potency is determined by the M2 assay.

Embodiment 78. The method of embodiment 71, wherein the therapeutic potency is determined by the NO assay.

Embodiment 79. The method of embodiment 71, wherein the therapeutic potency is determined by the WST-1 assay.

Embodiment 80. The method of embodiment 71, wherein the therapeutic potency is determined by the BCA protein assay.

Embodiment 81. The method of embodiment 71, wherein the therapeutic potency is determined by the HA content assay.

Embodiment 82. The method of embodiment 71, wherein the therapeutic potency is determined by the PTX3 content assay.

Embodiment 83. The method of embodiment 75, wherein an HA content of the composition is at least 75 μg/ml.

Embodiment 84. The method of embodiment 75, wherein an HA content of the composition is at least 90 μg/ml.

Embodiment 85. The method of any one of embodiments 62 to 75, wherein a total protein content of the composition is at least 250 μg/ml.

EXAMPLES

The following examples are provided to further illustrate some embodiments of the present disclosure but are not intended to limit the scope of the disclosure; it will be understood by their exemplary nature that other procedures, methodologies, or techniques known to those skilled in the art may alternatively be used.

Example 1. Preparation of Pooled Compositions

Objective: A comparability study was undertaken to evaluate the equivalency of fetal support tissue lots obtained from individual donor sample lots which contains single donor (not pooled fetal support tissue/product/extract or compound) and pooled samples which contains pooled fetal support tissue/product/extract or compound) in terms of their identity, functionality and to determine whether there are differences resulting from the pooling process.

Example of a preparation of extract: An injectable composition is prepared by mixing 10 mg each of the fetal support tissue product containing 100 mg of a preparation comprising: pooled fetal support tissue extract in a suitable form (e.g., micronized, morselized, cryopulverized, powder, sheet form that may be ground up or not, pulverized, etcetera) as disclosed herein containing pooled or unpooled placental tissue/umbilical cord tissue/amniotic membrane tissue/amniotic fluid/chorion tissue and/or combinations thereof. The extract may be mixed e.g., 10 mg of powder form mixed with 10 mL of 0.9% sterile saline (preservative-free saline). The composition or extract kits or methods, formulations as disclosed can contain extract of various particle sizes as desired and such a composition, for example, can be processed while fresh, frozen, or previously frozen, processed before or after pooling, or before/after being lyophilized, decellularized, devitalized (any other processing, e.g., sterilization, filtration, centrifugation etcetera as disclosed in the present application in a form most suitable). The mixture is incorporated into a dosage unit form suitable for administration by injection or any other administration route.

Background: The comparability study evaluated samples that were collected from single or individual donors versus a collection or pooled samples from a plurality of donors or multiple donors. Samples obtained from single or pooled donors were processed and manufactured following the sample protocol and methodology. An assessment to determine the equivalency in potency, stability, uniformity of particles, identity, functionality, efficacy, and sample-to-sample variability that may have occurred due to processing of single versus multiple pooled samples was investigated if there were any advantages of using pooled donor samples, and if so, to obtain evidence to support the process of pooling fetal support tissue, pooling fetal support tissue drug substance, pooling biologics isolated from the pooled fetal support tissue product.

In FIG. 7 to FIG. 11, data is provided showing example assays conducted on individual or single donor lots and pooled lots. The source material for the single donor lots versus pooled samples was the same (before pooling and after pooling) the sample. Experiments disclosed in the present application that compared individual sample lots versus pooled samples that evaluated in individualized experiments, were conducted to evaluate equivalency of non-pooled sample and pooled sample from their identify, functionality and efficacy using various established assay matrix disclosed herein (e.g., Table 6). The findings of these studies provide evidence to support the pooling process for pooled fetal support tissue drug product or extract and/or its manufacturing and processing.

Studies Overview: Pooling Characterization Study

A process characterization study was carried out to evaluate the initial pooling process at small scale (4 donors; see Table 7). To demonstrate the comparability between pooled lots and single donor lots regarding identity and potency, a comparability study was conducted. For the study, pooling was implemented using a container installed into an orbital shaker/mixer operated at 46 revolutions per minute (rpm) up to 15 minutes. Prior to pooling, micronized drug substance of each of the four donor lots (single or individual donor samples (before pooling) was analyzed for hyaluronic acid content, total protein, and ODI-TRAP. These results were combined to give a weighted average of each result prior to pooling. The micronized drug substance for 4 donor lots of conditions were each loaded into a 50 ml conical tube, mixed for two 5 minutes periods, and sampled after each mixing period.

Results: This study assessed the HA, total protein, and ODI-TRAP characteristics of the four donor samples before and after pooling. The study demonstrated that the pooling process was able to produce acceptable protein, HA, and residual moisture results. The variability of HA content, Total Protein, and ODI-TRAP was within the range expected due to variability among different donors. From the characterization study data, it is concluded that the pooling up to 15 minutes at 46 rpm is sufficient.

Comparability study: After confirming the comparability between single donor and pooled from 4 different donors, a scale-up multiple donor batch was prepared by pooling of 47 donors and evaluated the comparability between pooled (n=47), pooled (n=4) and single donor lots by testing identity, quality and potency using the assay matrix approach.

Results: This study demonstrated that pooled (n=47), pooled (n=4), and single donor lots all met the release criteria based on the HA and total protein (BCA) and ODI-TRAP assays (Table 3). These results collectively support the notion that upscaling the pooling process does not product significant differences in identity, quality, and potency between pooled sample lots and single or individual donor lots. Because the pooling process actually results in lower variability as indicated by the lower coefficient of variation (see Table 8) for pooled samples in all three assays when compared to the variability of individual npFST units, it was also concluded that the pooling process reduces variability among different donors (e.g., see Table 8, Table 11, Table 12).

This study also shows that pooling results in more uniform pooled donor bulk drug substance to mitigate variability among different donors and facilitate proficiency of further qualification, sampling, and clinical testing. Additionally, a scale-up batch, which pooled 47 donors, was produced for the purposes of generating stability data for pooled samples. Pooling of tissues for this stability lot was performed using mixer parameter settings developed during the characterization study and other early studies. This batch was shown to be comparable to the batch utilized in the characterization study and batches of single donor products.

A pooled native HC-HA/PTX3 complex (nHC-HA/PTX3) or composition was prepared by pooling fetal support tissue from multiple donors (n=3, or n=4 donors or n=6 or 47 donors, or as specified) and compared to a non-pooled composition. Prior to pooling, micronized drug substance of each of the individual pools was analyzed for hyaluronic acid content, total protein, and ODI-TRAP. These results were combined to give a weighted average of each result prior to pooling. FIGS. 1A-1B depict the pooling process from multiple donors.

Results: Because these data are aligned with requirements of the US FDA, the data obtained necessarily allow for adaptation of the pooling strategy during the processing and manufacturing steps of pooled fetal support tissue sample, extracts, devices, methods, kits, compositions (e.g., sheet, micronized, morselized, cryopulverized, powdered, sieved, ultrafiltered etcetera), products, or pooled bulk drug substance. Manufacturing of bulk drug substance for example, can be adopted to create sub-pools e.g., sub-pools of up to 15 donors prior to pooling to a larger batch e.g., a larger batch of up to 45 donors or even a larger batch of over 45 donor samples.

Viral testing on the sub-pooled drug substance and evaluations to test method suitability studies implemented enhance the ability to detect any safety concerns and enable traceability of donors for investigation of actual or suspected transmission of communicable disease at the drug substance level.

Sampling and processing fetal support tissues: Results from the single donor samples (n=4) from four different donor lots listed in Table 2 were prepared by pooling samples (per WI-0221 protocol) following established, standardized, in-house manufacturing and processing protocol. Table 2 summarizes the pooling effort and the sampling plan. A stability study was conducted with a composition manufactured through the pooling of 47 donors. All results met acceptance criteria for T=0, 1, 3 and 6 months. The critical quality attributes and in-process steps are shown in Table 1 and Table 2. The data demonstrates that the pooling process was able to produce acceptable protein, HA, and residual moisture results. The variability of HA content, total protein, and ODI-TRAP was within the range expected due to variability among different donors. The results also demonstrated that the pooled composition with 47 donors, the pooled composition with 4 donors, and data from single donor samples all met the release criteria based on the HA and total protein (BCA) and ODI-TRAP assays. These results collectively support the notion that upscaling the pooling process does not produce significant differences in identity, quality, and potency between the pooled lots and single donor sample lots. Moreover, because the pooling process resulted in lower variability as indicated by the lower coefficient of variation for pooled samples in all three assays (e.g., see Table 8, Table 11, Table 12).

TABLE 1

Exemplary Critical Quality Attributes

| Critical Quality Attribute Types | Critical Quality Attributes | Relevant Process Step(s) | In-process Controls | Test Material |
|---|---|---|---|---|
| Identity, Potency, Purity | Identity, Potency and Purity (Assay Matrix) | Lyophilization through Sieving | HA Content Testing | Pooled composition |
| | | | Total Protein by BCA Testing | Pooled composition |
| | | | ODI-TRAP Testing | Pooled composition |
| Quality | Tissue Appearance | Micronization | Tissue Appearance Verification | Pooled composition |
| | Water Content | Lyophilization | Water Content Testing by USP <921> | Pooled composition |
| | Particle Size | Micronization, Sieving | Particle Size Distribution Testing | Pooled composition |

TABLE 2

Exemplary Critical Quality Attributes

| Critical Quality Attribute Type | Critical Quality Attributes | Relevant Process Step(s) | In-process Controls | Test Material |
|---|---|---|---|---|
| Safety | Bioburden | DS and DP manufacturing steps prior to terminal sterilization | Pre-Sterilization Bioburden Testing | Filled and Crimped Drug Product |
| | Sterility | Terminal Sterilization | Sterility Testing per USP <71> | Pooled composition |
| | Endotoxin | DS and DP manufacturing steps | Endotoxin Testing per USP <85> | Pooled composition |
| Identity, Potency, Purity | Identity, Potency and Purity (Assay Matrix) | DS and DP manufacturing steps | HA Content Testing | Pooled composition |
| | | | Total Protein by BCA Testing | Pooled composition |
| | | | ODI-TRAP Testing | Pooled composition |
| Quality | Tissue Appearance | Micronization | Visual Inspection | Pooled composition |
| | Water Content | Lyophilization | Water Content Testing by USP <921> | Pooled composition |
| | Particle Size | Micronization, Sieving | Particle Size Distribution Testing | Pooled composition |
| | Dose | Filling and Crimping | Fill Weight Check | Filled Drug Product |
| | Container Closure Integrity | Filling and Crimping | Vial Inspection Leak Testing | Filled and Crimped Drug Product |

Example 2: Scale Up of Manufacturing of Fetal
Support Tissue Product

Umbilical cord/amniotic membrane fetal support tissue
product ("MAU") was manufactured using the following
process described below and illustrated in FIGS. 2A-2C.

Step 1: Raw Material to Regulatory Starting Material.
This step covers from the acquisition of tissue raw material
(i.e., human birth tissue) to the production of the Regulatory
Starting Material (RSM), which consists of human amniotic
membrane (AM) and umbilical cord (UC) tissue from an
individual donor. This step consists of donor screening,
procurement, receipt and inspection, donor eligibility deter-
mination, tissue cleaning, cutting, and soaking, to generate
the RSM.

Step 2: Drug Substance. Single Donor Processes and
Multiple Donor Processes. This step consists of the cryopul-
verization, extraction, centrifugation, and target fill volume
for individual donors. After sufficient number of donors are
achieved, multiple donors are pooled together in a mixer to
generate a pooled drug substance which can be further
diluted into different formulation to generate the drug sub-
stance (DS) or bulk drug substance (BDS).

Step 3: Drug Product. Sterile filtration with filling and
sealing in a blow fill seal (BFS) equipment. This step starts
with sterile filtration, filling and sealing of DS, into vials. DS
is filled into vials at a target fill weight of 2.0 mL per vial.
All sealed vials are visually inspected for defects and
sampled for container closure integrity by leak testing before
labeling. Representative vials are sampled and tested for
release.

TABLE 3

| Exemplary results from the Assay Matrix Experiments | |
| --- | --- |
| Attribute | Method Description |
| Identity | HA Content |
| Potency | ODI-TRAP |
| (Matrix) | M2 (NO) |
| Safety | Endotoxin |
| | Sterility |
| Purity | Agarose Gel |
| | Electrophoresis |
| | Western Blot |
| | Analysis |
| Quality | Total Fill Volume** |
| | Total Dispensing |
| | Volume** |
| | Appearance |
| | Particle Size |
| | Analysis |
| | Primary Container |
| | Closure System |
| | Integrity** |
| | Secondary Container |
| | Closure System |
| | Integrity |

Example 3: Assay Matrix (Multiple Assays)
Evaluation of Pooled Biological Samples Fetal support tissue from multiple donors has been shown
to display the advantage of having decreased sample vari-
ability compared to single donor samples (Table 8). Char-
acterization of the amniotic membrane and umbilical cord
have shown the extracellular matrix (ECM) of AM and UC,
are enriched in hyaluronic acid (HA). HA present in AM/UC
exists as nHC-HA/PTX3. Pooling of donor samples increases this enrichment. The methods disclosed describe
assessing preservation of the structural and biological activ-
ity of signaling molecules of AM and UC or fetal support
tissue that has been cryopreserved and therefore retains the
potency, stability of tissue bioactive factors, including the
compositions for example, preservation of potency and
stability of HA (which exists in AM/UC as native HC-HA/
PTX3). Dehydration of fetal support tissue by heat drying
ECM HA alters or destroys the nHC-HA/PTX3 complex, by
potentially dissociating HC1 from HA and degrading and
removing PTX3, a critical HC-HA stabilizing protein,
thereby degrading the HA biological factor from the high
molecular weight HA to an unbound low molecular weight
HA (Cooke et al., 2014). Degradation by dehydration (using
heat) of the high molecular weight HA and therefore the
nHC-HA/PTX3 complex, results in compositions with dis-
tinctly less anti-therapeutic biochemical and biological fac-
tors causing decreased potency and reduced clinical efficacy
of the fetal support tissue compositions in general (Cooke et
al, 2014).

The present methods offer improvements and methods to
prevent the degradation of nHC-HA/PTX3, which are not
routinely applied. The methods specifically include
improvements in the process of dehydrating fetal support
tissue while retaining and preserving the HA and all bio-
logical factors of the fetal support tissue, including but not
limited to HC-HA/PTX3. Additionally, improvements in the
methods to lyophilize fetal support tissue, to provide for
higher concentrations of HA with reduced variability have
been achieved herein. These methods include the processing
of fetal support tissue and or compositions, or products in
such a way as to perform lyophilization under low-tempera-
ture conditions that leads to stable compositions/extracts or
products e.g., stable HC-HA complex e.g., nHC-HA/PTX3
complex.

The potency and preservation of fetal support tissues are
evaluated using multiple assays, or the Assay Matrix (e.g.,
Table 1, Table 3, Table 5, Table 6). Following guidelines
described in the "*FDA Guidance—Potency Tests for Cellu-
lar and Gene Therapy Products*, January 2011," multiple
assays (Assay Matrix) were adopted to evaluate product
potency in cases where a single biological or analytical
assay may not provide an adequate measure of potency
because the product is complex and/or does not have a fully
characterized mechanism of action (MOA) or has multiple
active ingredients and/or multiple biological activities. The
potency evaluation to evaluate the product preservation and
potency of the nHC-HA/PTX3 complex was determined
using various assay matrix. These data can be seen in e.g.,
Table 3, Table 5, Table 6, Table 11, Table 12. The assay
matrix may include assays that provide a quantitative read-
out (e.g., units of activity) and/or qualitative readout (e.g.,
pass/fail) and might consist of a combination of biological
assays, biological and analytical assays, or analytical assays
alone.

An established stability-indicating profile that provides
assurance that changes in the identity, purity, and potency of
the fetal support tissue product, such as HA or nHC-HA/
PTRX3 product that are detected based on the assay matrix.
This assay matrix includes biochemical assays include 1)
HA Assay, 2) Bicinchoninic Acid (BCA) Protein Assay, 3)
Western Blot HC1 and PTX3 and 4) Agarose Gel for HA as
well as 5) cell based potency assays which comprise of (i)
optical density of immunoreactivity-tartrate-resistant acid
phosphate activity (ODI-TRAP) Assay, (ii) Nitric Oxide
(NO) Assay, (iii) M2 IL-12 Assay and (iv) Western blot
(WST-1) Assay (e.g., Table 3, Table 5, Table 6, Table 11, Table 12). An example of the output or results, including test parameters or attributes, method description and test methods from the assay matrix experiments can be seen in Table 3.

Example 4. Lyophilization and Micronization of the Fetal Support Tissue

Lyophilization

Lyophilization of fetal support tissue process continues throughout the various stages of development of the tissue processing and manufacturing exercise including processing of tissues, compositions, extracts, products etcetera. The lyophilization process commences for example, at the preliminary stage in development of a particular lot in a drug substance processing step. For example, such a process can start at and include freezing the (pooled or single donor) fetal support tissue at a range of $-45°$ C. to $-25°$ C. for 1-5 hours (Table 4). Thereafter, a primary and secondary dry process is completed. The primary dry process for example, includes incubating the samples at a temperature range of $-24°$ C. to $0°$ C. under 10 mTorr to 750 mTorr Pressure (abs.) for about 10-60 hours. The primary dry is followed by the secondary dry procedure, which is performed at a temperature range of $15°$ C. to $40°$ C. under 10 mTorr to 300 mTorr Pressure (abs.) for 1-48 hours. Following the primary/secondary dry periods, there is a hold period which follows the secondary dry procedures. At the hold period, the samples are held at $15°$ C. to $40°$ C. under 10 mTorr to 300 mTorr Pressure (abs.) for 1-48 hours. After the "hold" stage, this completes the lyophilization process that occurs at the preliminary stage in development.

Plates loaded with tissue that is processed and packaged from each individual donor are lyophilized under controlled temperature and pressure with primary drying settings based on a differential pressure endpoint and pre-determined lyophilization cycle parameters. After lyophilization, the lyophilized tissue is stored in a desiccator cabinet at room temperature for up to 14 days prior to micronization. Following the low temperature lyophilization process, the step of micronization also preserves the components of the fetal support tissue.

TABLE 4

| Process Comparison for Lyophilization over Stages of Development | |
|---|---|
| Drug Substance Process Step | Preliminary Development Lot |
| Lyophilization | Freeze: <br> $-45°$ C. to $-25°$ C. <br> 1-5 hours <br> Primary Dry: <br> $-24°$ C. to $0°$ C. <br> 10 mTorr to 750 mTorr Pressure (abs.) <br> Time Endpoint 10-60 hours <br> Secondary Dry <br> $15°$ C. to $40°$ C. <br> 10 mTorr to 300 mTorr Pressure (abs.) <br> 1-48 hours <br> Hold: <br> $15°$ C. to $40°$ C. <br> 10 mTorr to 300 mTorr Pressure (abs.) <br> 1-48 hours |

Micronization

Lyophilized tissue from each donor is micronized separately by a stainless-steel ball mill at pre-determined micronization parameters that include frequency and duration. The ball mill is cleaned, and steam sterilized prior to micronization of each batch. Once complete, micronized tissue from each donor is stored in separate sterile container that is placed in a sealed foil pouch and stored in a desiccator cabinet at room temperature for up to 21 days.

Micronization parameters are the following: Ball mill, 25 Hz; AM: 6 min; and UC: 7 min.

Although micronization has produced consistent particle size distribution results, larger particles potentially could block the injection needle. For this reason, a sieving process step, was added to the manufacturing process after the pooling step.

The process of lyophilization described is used to obtain a higher concentration of HA. Both the powder and liquid forms of the fetal support tissue contain nHC-HA/PTX3 complex. To prepare powder form, fresh or frozen fetal support tissue that has undergone donor eligibility screening is cleaned, cut, soaked, and become a Regulatory Starting Material (RSM). Subsequently, under aseptic, room temperature conditions, the RMS undergoes the processes of lyophilization and micronization to grind to fine particles (FIG. 1A). Micronization is performed with or without lyophilization into liquid or powder forms. For powder forms, the micronized fetal support tissue is sieved for particle sizing and following the in-process controls and quality control assessments, the sieved tissue become a bulk drug substance (BDS) that is packaged and undergo various terminal sterilization processes to become a finished drug product (FIG. 1B).

The powdered tissue containing native HC-HA/PTX3 is reconstituted in a suitable buffer and used immediately, or the powder is stored frozen at $-80°$ C. A liquid form of the fetal support tissue is prepared by rehydration after the micronization processes. A liquid form of the fetal support tissue is prepared following cryopulverization wherein the tissue is processed aseptically at $4°$ C. conditions (FIGS. 2A-2C) and is extracted, centrifuged and/or filtered at various centrifugation and/or filtration parameters to control particle sizes. Filtration is performed to sterilize the extract (filter pore size of equal to about to less than 0.2 um). Following cryopulverization of the tissue, it is processed as indicated in FIGS. 2A-2C; the tissue composition is pooled, diluted at various concentrations as needed, and after in-processing controls (involving various assays as shown e.g., in Table 5, Table 6) are completed, the extract or composition containing nHC-HA/PTX3 is packaged as a finished drug product.

TABLE 5

| Additional assays developed for HC-HA/PTX3 release in clinical trial experience | | | | |
|---|---|---|---|---|
| Attribute | Assay Description | Assay Type | Assay Category | Release Criteria |
| Identity, Potency | ODI-TRAP Assay | Quantitative | Biological | Numerical |
| | WST-1 (cell metabolic activity) Assay | Quantitative | Biological | Numerical |
| | HA Assay | Quantitative | Analytical | Numerical |
| | BCA Protein Assay | Quantitative | Analytical | Numerical |
| | M2 Polarization Assay based on NO measurement | Quantitative | Biological | Numerical |

TABLE 6

Analytical Test Matrix

| Potency Assay Characteristics | | BCA Protein Assay | HA Assay | Western Blot Assay | Agarose Gel | ODI-TRAP Assay | M2 Assay* |
|---|---|---|---|---|---|---|---|
| Demonstration of Bioactivity Based on Mechanism of Action | | Bioactivity mediated by proteins (growth factors, cytokines, etc) including HC-HAPTX3 | Bioactivity mediated by HA including HC-HAPTX3 | Qualitative characteristic of HC1 and PTX3 in HC-HA/PTX3 responsible for bioactivity | Qualitative characteristics, e.g., molecular mass of HA | Bioactivity of HC-HA/PTX3 in inhibiting osteoclast differentiation | Bioactivity of HC-HAPTX3 in polarizing M2 macrophages |
| Appropriate for Lot Release | | X | X | | | X | X |
| Specific to the Product | | | | X | X | X | X |
| Quantitative | | X | X | | | X | X |
| Can demonstrate lot-to-lot consistency | | X | X | X | X | X | X |
| Validated: to meet pre-defined acceptance/rejection | Method | X (V-GLP-14-001) | X (V-GLP-15-001) | | | | X (V-GLP-14-006, V-GLP-16-002) |
| Compared to reference control | | Protein standards | HA standards | Purified HC1, PTX3, and Purified HC-HA/PTX3 | HA size markers. Healon HA and Purified HC-HA/PTX3 | Purified HC-HA/PTX3 | Purified HC-HA/PTX3 |

TABLE 7

Sampling Plan

| Group | Sample | Total Weight (mg) |
|---|---|---|
| A (Single donor fetal support tissue samples) | donor 1 | 200 |
| | donor 2 | 200 |
| | donor 3 | 200 |
| | donor 4 | 200 |
| B (Pooled fetal support tissue samples) | donor 1 + donor 2 + donor 3 + donor 4 | (100 + 100 + 100 + 100) = 400 |
| | donor 1 + donor 2 + donor 3 + donor 4 | (100 + 100 + 100 + 100) = 400 |
| | donor 1 + donor 2 + donor 3 + donor 4 | (100 + 100 + 100 + 100) = 400 |

Example 5. Assay Matrix: Identity and Potency Using Biochemical Assays

Hyaluronic Acid (HA) Quantitation Assay: The pooled composition of fetal support tissue comprises hyaluronic acid (HA). HA quantitation was performed in triplicate (n=3) per sample and the identity and potency was determined by the HA assay, a quantitative and analytical assay to evaluate HA content, a major extracellular matrix in both AM and UC (which exists in these tissues as nHC-HA/PTX3 complex). The HA assay as one of the initial product release tests, is used for identity, purity, and potency evaluations. The HA assay performance and suitability as measured by studying accuracy, precision (repeatability, intermediate precision), specificity, linearity, range, system suitability and robustness was determined.

Results:

Hyaluronic Acid (HA) quantitative assay (HA assay): Quantitation was performed according to WI-0212 in-house sample processing protocol in triplicate (n=3) per sample. The standard linearity $R^2$ value was 0.989 for the range of 0.05-0.80 µg/ml.

Figure 7:
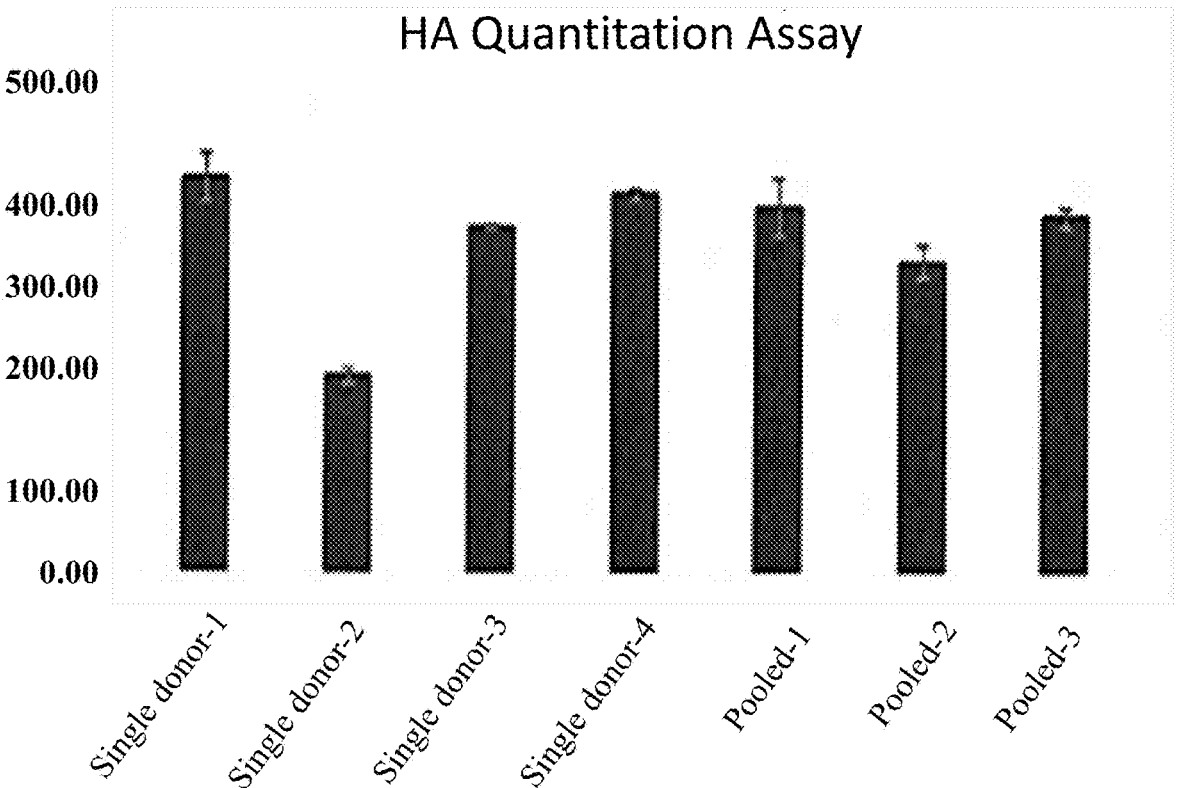
FIG. 7 shows an example of a hyaluronic acid (HA) quantification (µg/ml HA) for samples obtained from individual or single donor lots and pooled lots.

A dilution of 1:1000 was used for all samples. The HA levels of all samples met the HA minimum criteria (i.e., >90 µg/ml). Overall, the HA quantity remained high in single or pooled sample lots (FIG. 7). The mean HA level was 329.4 µg/mL for four single donor fetal support tissue sample lots (single donor samples) and 344.7 µg/mL for three pooled donor fetal support tissue sample lots (pooled samples; Table 8, p>0.05 using Student's t-test). The Standard Deviation (SD) of HA level was 90.2 µg/mL (CV: 27.4%) among four single donor lots (range 197-395 µg/ml) while 28.8 µg/mL (CV: 8.4%) among three pooled sample lots (range 311-365 µg/ml; Table 8), indicating that pooled samples is more uniform and representative, which supports the effectiveness of pooling.

TABLE 8

Individual donor samples and pooled fetal tissue samples HA Data Analysis

| Group | Donor ID | Average OD | HA (µg/mL) | Average (µg/mL) and CV % | P-value (A vs B) |
|---|---|---|---|---|---|
| A (Single donor fetal tissue samples) | Donor 1 | 1.13 | 395 ± 23.6 | 329.4 ± 90.2 CV: 27.4% | 0.766 |
| | Donor 2 | 1.54 | 197 ± 8.0 | | |
| | Donor 3 | 0.61 | 346 ± 1.5 | | |
| | Donor 4 | 1.02 | 378 ± 6.0 | | |
| B (Pooled donor fetal tissue samples) | Pooled-1 | 1.01 | 365 ± 28.1 | 344.7 ± 28.8 CV: 8.4% | |
| | Pooled-2 | 1.54 | 311 ± 15.8 | | |
| | Pooled-3 | 1.09 | 356 ± 9.1 | | |

HA Quantities Using an HA Test Kit:

An HA Test Kit measures HA levels and was performed as an enzyme-linked binding protein assay that used a capture molecule known as the hyaluronic acid binding protein (HABP) a receptor for HA. An enzyme-conjugated version of HABP was also used to measure the HA captured from test samples by the HABP coated microwells, in an ELISA-based assay set up. HA concentrations of samples were determined from a reference curve resulting from OD units of five HA reference samples of known HA concentration and 0 ng/mL (reagent blank). An assay acceptance criterion is a numerical range, such as, "no less than" (NLT), that was applied throughout the product development stages to reflect manufacturing and clinical experience. The pooled fetal support tissue extract possesses adequate potency at an NLT of at least 1 µg/ml to 3000 µg/ml.

Bicinchoninic Acid (BCA) Protein Assay: The BCA assay is a quantitative and analytical assay to measure total protein content in the tissue matrix i.e., HC-HA/PTX3, extracellular matrices, growth factors/cytokines and other bioactive factors found in tissue including the drug substance. The BCA assay is one of the initial product release tests to identity and potency. BCA Total Protein quantitation was performed according to established, in-house processing protocol (WI-0211) in triplicate (n=3) per sample. Dilution of samples was not performed. The standard linearity $R^2$ value was 0.989 for the range of 25-2000 µg/ml.

BCA assay performance and suitability as measured by studying accuracy, precision (repeatability, intermediate precision), specificity, linearity, range, system suitability and robustness was determined. Total protein content determined by the BCA assay is an effective measure to identify protein content in the HC-HA/PTX3 complex, assess tissue preservation and integrity of the matrix and the inherent cytokines. The total protein content is evaluated by the BCA colorimetric assay; a protein in an alkaline medium that reduces Cu+2 to Cu+1 is detected using a reagent containing bicinchoninic acid. A purple color proportional to the protein content in the sample is produced following the chelation of two BCA molecules to one cuprous ion; absorbance at 526 nm is proportionate to the protein concentration in the sample. An assay acceptance criterion can be a numerical range, such as, "no less than" (NLT) that is applied throughout the product development stages to reflect manufacturing and clinical experience. For the BCA assay, NLT was determined that the fetal support tissue extract possessed potency at an NTL of at least 1 µg/ml to 5000 µg/ml.

Results: The mean protein level was 717.5 µg/mL for four single donor lots and 816.4 µg/mL for three pooled donor sample lots, showing there was more total protein obtained when the single donor samples were pooled prior to the BCA protein quantification assay was conducted (p<0.05 using Student's t-test), Table 9 and FIG. 11. The values of all samples met the protein minimum criteria (i.e., >250 µg/ml). The SD of protein level was 39.4 µg/mL (CV: 5.5%) between four single donor sample lots (range 659-745 µg/mL) while it was 10.3 µg/mL (CV: 1.3%) between three pooled donor sample lots (range 804-823 µg/mL). However, there was more variability detected in among the single donor lots as compared to the pooled sample lots (Table 9). These data demonstrate that there is higher variability in the protein quantities when single donor samples lots are processed than in from the pooled donor samples These data also suggests that the pooled donor (tissue samples/product) is more uniform and representative than the individual or single donor samples.

TABLE 9

BCA assessment of total protein content in single
donor samples and pooled donor samples

| Group | Donor ID | Average OD | Protein (µg/mL) | Average (µg/ml) & CV % | P-value (A vs B) |
|---|---|---|---|---|---|
| A (Single donor fetal tissue samples) | Donor sample 1 | 1.66 | 659 ± 5.8 | 717.5 ± 39.4 CV: 5.5% | 0.009 |
| | Donor sample 2 | 1.86 | 745 ± 42.1 | | |

TABLE 9-continued

BCA assessment of total protein content in single
donor samples and pooled donor samples

| Group | Donor ID | Average OD | Protein (µg/mL) | Average (µg/ml) & CV % | P-value (A vs B) |
|---|---|---|---|---|---|
| | Donor sample 3 | 1.82 | 730 ± 11.1 | | |
| | Donor sample 4 | 1.84 | 735 ± 10.1 | | |
| B (Pooled donor fetal tissue samples) | Pooled sample 1 | 2.03 | 823 ± 4.3 | 816.4 + 10.3 CV: 1.3% | |
| | Pooled sample 2 | 1.99 | 804 ± 17.2 | | |
| | Pooled sample 3 | 2.03 | 821 ± 50.7 | | |

Western Blot Analysis

Western blot analysis was conducted to detect qualitative changes in HC-HA/PTX3 complex.

Figure 8A:
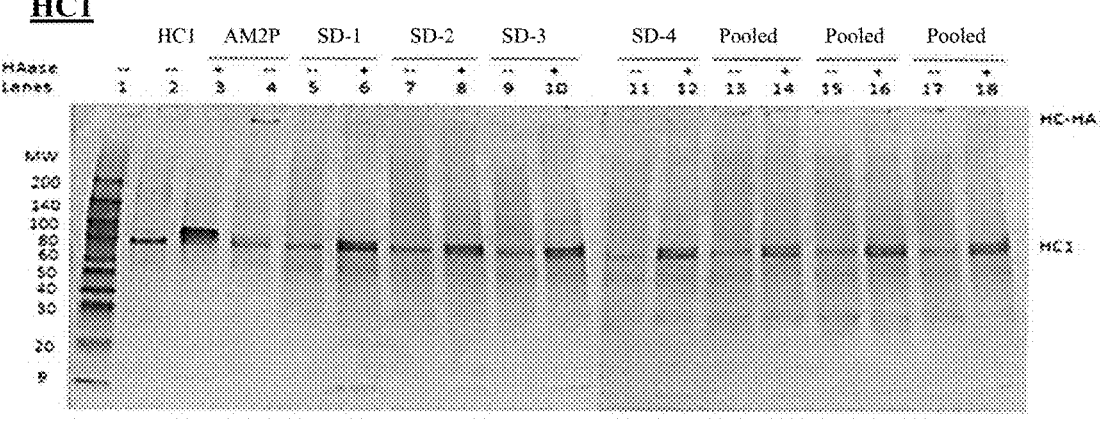
FIGS. 8A-8B show an example of a Western blot analysis of fetal support tissue product. Sample lots obtained from single donor lots and pooled donor lots were evaluate in a Western blot assay to qualitative assess changes in heavy chain 1 (HC1.

Heavy Chain 1 (HC1): The HC1 positive control (Iα1 treated with 100 mM NaOH) was detected at 80 kDa band. All samples including Reference Material (RM), a total of 10 µg hyaluronic acid (HA) was loaded into each loading well. The presence of HC1 (in HC-HA) was detected using hyaluronidase (HAase) digestion. The Reference Material (having e.g., amniotic membrane purified HC-HA/PTX3) showed a hyaluronic acid-hyaluronan (HC-HA complex) band in the top part of the loading well, which disappeared with the 80 kDa HC1 band intensity following HAase digestion (FIG. 8A in lanes 3, 6, 8 and 10 for single donor lots and lanes 12, 14, 16 and 16 for pooled samples), confirming the presence of HC-HA complex. Lanes 5-10 of FIG. 8A denote samples from single donor lots (lane 5/6 single donor 1; lanes 7/8 single donor 2; lanes 8/9 single donor 3) while lanes 13/14 pooled sample lot 1; lanes 15/16 pooled sample lot 2; lanes 17/18 pooled samples 3). One of each pair of donor sample lot was subjected to HAse digestion. Although there was no clear HC-HA band in the top part of loading well without HAase digestion for individual single donor sample lots and pooled donor sample (FIG. 8A in lanes 4, 5, 7 and 9), there was a similar increase of the intensity of the HC1 band with HAase digestion (FIG. 8A).

Figure 8B:
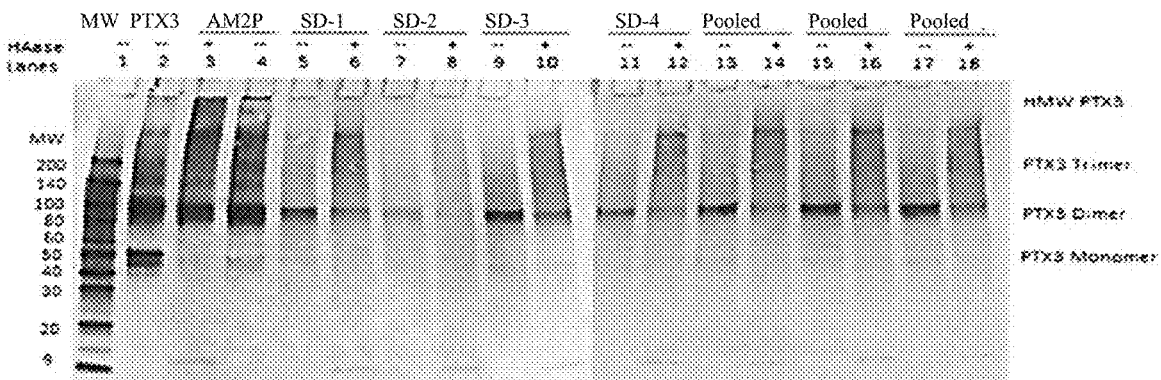

Pentraxin 3 (PTX3): The same gel used for HC1 was striped and used for western blotting of PTX3. The PTX3 control (i.e., recombinant human PTX3) was detected as PTX3 monomer (~50 kDa doublet due to glycosylation), dimer (~100 kDa), trimer and high molecular weight (HMW) PTX3 (FIG. 8B). Without HAase digestion, the Reference Material showed HC-HA/PTX3 complex in the top of the loading well, PTX3 dimer, and various PTX3 species larger than dimer. With HAase digestion, the intensity of HMW PTX3 species was increased (FIG. 8B in lanes 6, 8, 10 and 12) for single donor samples and lanes 14, 16 and 18 for pooled samples). All single donor sample and pooled samples showed a major PTX3 dimer without HAase digestion (lanes 5, 7, 9, 11 for single donor samples and 13, 15 and 17 for pooled samples) and HMW PTX3 smear pattern with HAase digestion (FIG. 8B). However, single donor-2 (FIG. 7), which showed a lower HA level, had a relatively weaker detection of PTX3 (lanes 7 and 8) compared to all other samples.

Collectively, the above data indicated that the pooling process in pooled sample lots did not generate qualitative difference in preserving the HC-HA/PTX3 complex. The pattern after pooling donor sample was more uniform and representative than that from individual single donor lot.

Agarose Gel Electrophoresis

Agarose gel electrophoresis was used to perform qualitative analysis of HA according to its molecular weight. For each lane, the same amount of 10 µg HA was loaded for each sample. Lane 1 contains the molecular marker/ladder. The high molecular weight (HMW) HA standard (Healon) which reached >3000 kDa while the Reference Material, HC-HA (which is part of HC-HA/PTX3 complex) isolated and purified from AM, also reached the same level of HMW (FIG. 9, Lane 2 and 3, respectively). It should be noted that the agarose gel electrophoresis data of pooled sample before gamma-irradiation also exhibited similar HMW HA. Compared to this data, the agarose gel data obtained from each single donor sample lots and pooled sample lot showed HA at molecular weight (MW) of <600 kDa (FIG. 9), indicating that such MW change of HA was due to gamma-irradiation. Because there was no visible difference in MW among different single donor and pooled samples, we also concluded that both single donor samples and pooled samples preserve the same MW HA, supporting the notion that the pooling process did not cause any damage to HA isolated/purified from the fetal support tissue disclosed herein.

ODI-TRAP Assay

Each sample of single donor lots and pooled sample lot was tested per WI-0319 protocol by measuring percent TRAP inhibition at the concentration of 100 and 300 µg/mL HA, n=6 per sample. The negative and positive control are significantly different in TRAP expression (p<0.05) and the Reference Material (e.g., drug product containing HC-HA/PTX3 isolated and purified from AM) at 5 µg/mL HA exhibited significant TRAP inhibition (p<0.05).

Under the same condition, all single donor lots and pooled samples significantly (p<0.05) inhibited TRAP activity at 300 µg/mL and 100 µg/mL HA (FIG. 10A-10B). The mean TRAP inhibition was 91.8% for four single donor lots (FIG. 10A) and 88.9% for pooled samples (FIG. 10B) at 300 µg/mL HA (Table 5, p=0.307 using Student's t-test). The SD of percent (%) inhibition was 4.4 (CV: 4.8%) among four single donor lots but was 2.0 (CV: 2.2%) among three pooled sample lots (Table 11 and FIG. 10A-10B). This data suggests that both single donor lots and pooled samples exerted potent TRAP inhibitory effect. However, pooled sample lot exhibited more uniformity than single donor samples as evidenced by much less CV, again demonstrating that sample-to-sample variability was much higher among single donor sample lots than for pooled sample lots.

An assay acceptance criterion can be a numerical range, that is applied throughout the product development stages to reflect manufacturing and clinical experience. For the ODI-TRAP testing, pooled fetal support tissue drug product possessed potency and significantly inhibits TRAP activity (p<0.05) compared to positive control when loaded between 1 µg/ml and 1000 µg/ml HA.

References: comparability Study Protocol FDA: Guidance for Industry: Comparability Protocols—Chemistry, Manufacturing and Controls Information (Draft) February 2003

WI-0211: Total Protein Quantitation by BCA Assay
WI-0212: Hyaluronic Acid Quantitation Assay
WI-0214: Protein Analysis by Western Blot
WI-0230: Preparation of Buffers for SDS-PAGE and Western Blot
WI-0319: In situ ODI-TRAP Assay
WI-0282: Preparation of AMUCM Extract by Centrifuge

Example 6. Assay Matrix: Potency Using Cell-Based Assays

Optical density of immunoreactivity-tartrate-resistant acid phosphate activity (ODI-TRAP) Assay: In one aspect, described herein, the pooled composition of fetal support tissue comprises a potency as determined by ODI-TRAP. Osteoclast Differentiation Inhibition by Tartrate Resistant Acid Phosphatase (ODI-TRAP) method uses the TRAP enzyme that is highly expressed by osteoclasts, which can be differentiated from monocytes-macrophages (e.g., RAW cells). The cell-based ODI-TRAP assay is a quantitative biological test that measures the specific activity of HC-HA/PTX3 in pooled fetal support tissue based on its activity in inhibiting TRAP activity. The assay includes negative control, positive control, and in-house (internal) reference material (IRM), which is HC-HA/PTX3 highly purified from human AM tissue. A statistically significant difference (p<0.05) between the positive control (RANKL treatment to induce TRAP activity) and pooled fetal support tissue with RANKL-treated cells indicates that the pooled fetal support tissue has sufficient potency to inhibit TRAP activity. Inhibition of TRAP activity by pooled fetal support tissue varies relative to HA content measured in pooled fetal support tissue. In certain embodiments, the pooled fetal support tissue possesses adequate potency if a statistically significant difference compared to positive control is exhibited for fetal support tissue with an HA content of at least 50 µg/mL, 100 µg/mL, 150 µg/mL, 200 µg/mL, 250 µg/mL, 300 µg/mL, 350 µg/mL, 400 µg/mL, 450 µg/mL, 500 µg/ml, 600 µg/ml, 700 µg/ml, 800 µg/ml, 900 µg/ml, 1,000 µg/ml.

Regarding the ODI-TRAP assay (FIG. 3), IRM (HC-HA/PTX3) (25 µg/ml) inhibited TRAP activity with inducing cell death. Additionally, samples (t=0) from all 3 donors inhibited TRAP activity at 500 µg/ml with cell death.

To further measure the potency of pooled fetal support tissue, extract or compound, the percent (%) inhibition of TRAP was measured by ODI-TRAP assay. Undialyzed fetal support tissue composition in saline with or without dilution showed inhibition of TRAP activity at 50 µg/ml (all p<0.05) and both dialyzed fetal support tissue composition in saline and fetal support tissue composition in water-for-injection with or without dilution dose-dependently inhibit TRAP activity from 300 to 500 µg/ml (all p<0.05 vs positive control) (FIG. 631). As shown in Table 10, fetal support tissue used at a concentration of 1 µg/ml to 1000 µg/ml significantly inhibited TRAP by at least 25%-98% when compared to positive control (similar concentration).

TABLE 10

| Shows the typical acceptance criterion used to determine effectiveness of the assays | | |
| --- | --- | --- |
| Assay | Typical acceptance criterion | Range |
| TRAP | Inhibit TRAP p < 0.05 compared to positive control when loaded between 1 µg/ml and 1000 µg/ml HA | % Inhibition Min: 25% % Inhibition Max: 98% |
| WST-1 | Inhibit cell metabolic activity p < 0.05 compared to positive control when loaded between 1 µg/ml and 1500 µg/ml HA | |
| HA | NLT 90 µg/mL HA | Min: 226 µg/mL HA Max: 508 µg/mL HA |
| BCA | NLT 120 µg/mL Protein | Min: 313.06 µg/mL Protein Max: 840 µg/mL Protein |
| M2 | Inhibit IL12 p < 0.05 compared to positive control when loaded between 1 µg/ml and 1000 µg/ml HA | |
| NO | Inhibit NO p < 0.05 compared to positive control when loaded between 1 µg/ml and 1000 µg/ml HA | |

TABLE 11

| | HA Results | | | Protein Results | | | % TRAP Inhibition | | |
|---|---|---|---|---|---|---|---|---|---|
| Sample | Range | SD | CV % | Range | SD | CV % | Range | SD | CV % |
| Single donor (n = 4) | 197-395 µg/mL Average: 329.4 µg/mL | 90.2 µg/mL | 27.4% | 659-745 µg/mL Average: 717.5 µg/mL | 9.4 µg/mL | 5.5% | 88.1-96.8% Average: 91.9% | 4.43 µg/mL | 4.8% |
| Pooled donor sample (n = 3) | 311-365 µg/mL Average: 344.7 µg/mL | 28.8 µg/mL | 8.4% | 804-823 µg/mL Average: 816.4 µg/mL | 10.3 µg/mL | 1.3% | 88.5-91.1% Average: 88.9% | 2.0 µg/mL | 2.2% |

*Shows that pooling reduces variability and reduced percent CV*

TABLE 12

*Single donor sample and pooled fetal support tissue sample ODI-TRAP Data Analysis (at 300 µg/ml HA)*

| Group | Donor ID | Average OD (540-670 nm) | P-Value vs. Pos CTRL | % Inhibition | Average % Inhibition | P-Value (A vs B inhibition) |
|---|---|---|---|---|---|---|
| A (single donor sample lots) | Neg Ctrl | 0.49 | 1.3E−09 | N/A | N/A | 0.307 |
| | Pos Ctrl | 4.34 | N/A | N/A | | |
| | Internal Reference Material purified/native (HC-HA/PTX3) | 1.05 | 2.9E−08 | 75.6 | | |
| | Single donor-1 | 0.51 | 1.5E−08 | 88.1 | 91.9 + 4.4 | |
| | Single donor-2 | 0.13 | 6.6E−08 | 96.8 | CV: 4.8% | |
| | Single donor-3 | 0.24 | 7.2E−08 | 94.4 | | |
| | Single donor-4 | 0.51 | 5.4E−09 | 88.1 | | |
| B (pooled donor sample lots) | Neg Ctrl | 0.34 | 2.2E−06 | N/A | N/A | |
| | Pos Ctrl | 3.6 | N/A | N/A | | |
| | Internal Reference Material purified/native (HC-HA/PTX3) | 0.74 | 2.8E−06 | 79.5 | | |
| | Pooled-01 | 0.41 | 3.6E−06 | 88.5 | 88.9 ± 2.0 | |
| | Pooled-02 | 0.32 | 4.1E−06 | 91.1 | CV: 2.2% | |
| | Pooled-03 | 0.46 | 4.4E−06 | 87.2 | | |

M2 Polarization Assay based on NO measurement: Lipopolysaccharide (LPS) and interferon gamma (IFNγ) can stimulate murine macrophage cell line RAW264.7 cells to polarize into M1 macrophages, a pro-inflammatory phenotype, and produce high nitric oxide (NO) through upregulation of inducible NO synthase (iNOS), a pro-inflammatory mediator, while M2 macrophages, an anti-inflammatory phenotype, produce low NO. Thus, inhibition of NO production indicates an anti-inflammatory efficacy via downregulation of M1 macrophages. The production of NO in culture cells or culture supernatants can be determined by NO assay, which quantifies nitrite, the stable NO metabolites, using Griess reagents to generate a colored product with absorbance at 540 nm. Therefore, the anti-inflammatory effectiveness of test samples, e.g., HC-HA/PTX3 or HC-HA/PTX3-containing tissue extracts, can be demonstrated by the inhibition of NO production in LPS/IFNγ stimulated RAW264.7 macrophage cells by NO assay. In certain embodiments, the pooled fetal support tissue possesses adequate potency if a statistically significant difference compared to positive control is exhibited for fetal support tissue.

Figure 6A:
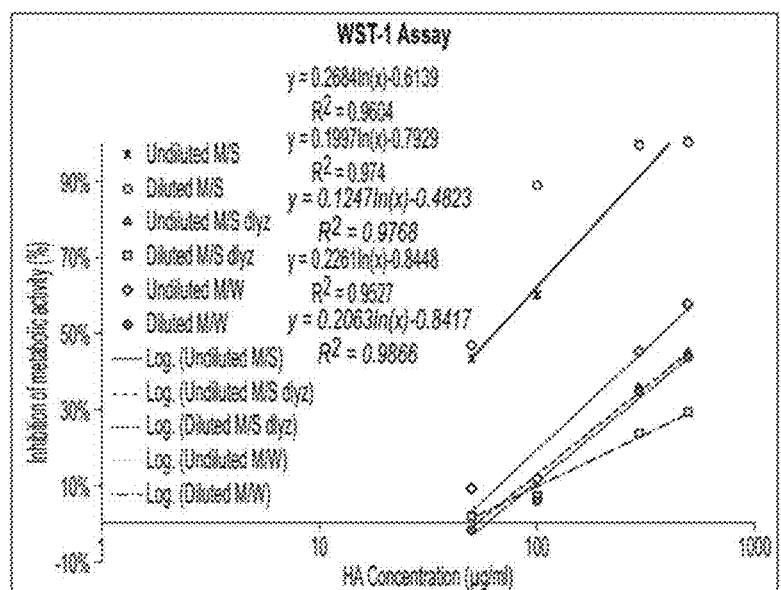
FIGS. 6A-C show an example of a dose-dependent linearity analysis of Hyaluronan ("HA") concentration in three potency assays a WST-1 assay (FIG. 6A); a TRAP assay (FIG. 6B); a M2 IL-12 assay (FIG. 6C). Abbreviations MS=MAU/saline; M/W=MAU/WFI; M/S dlyz=MAU/saline dialyzed; MAU=Morselized Amniotic Membrane and Umbilical Cord; WFI=water for injection.
Figure 6B:
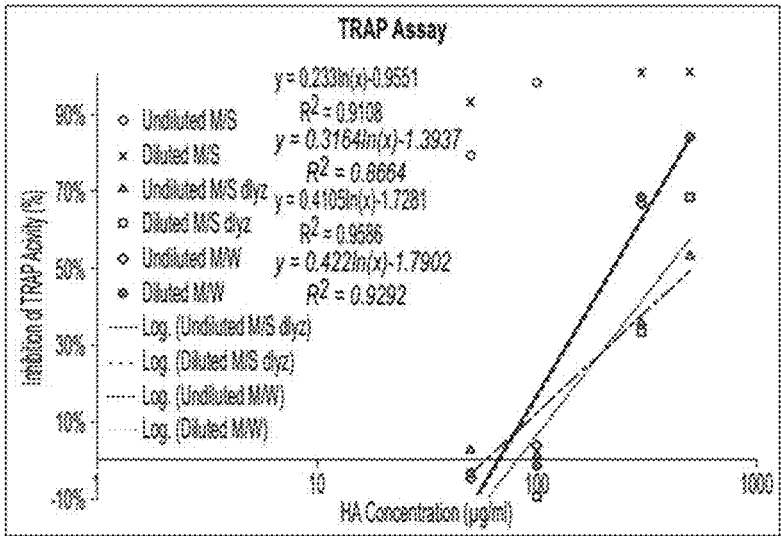
Figure 6C:
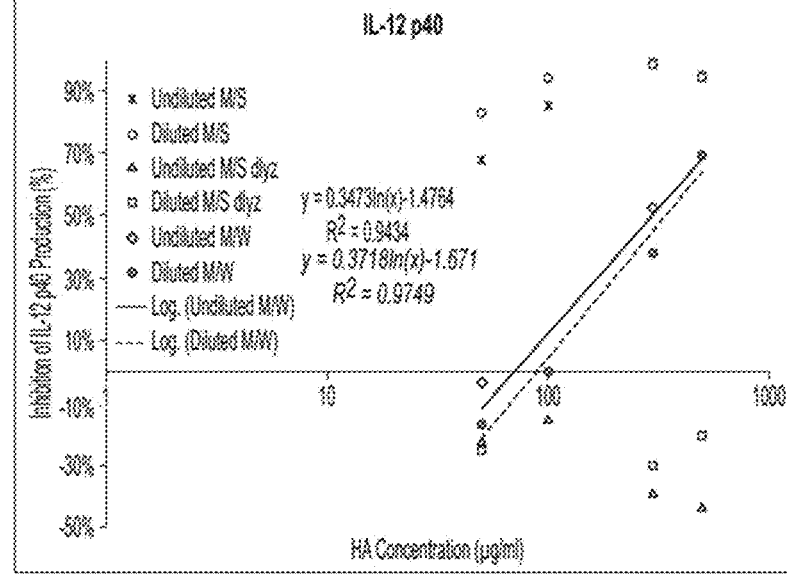

Regarding the M2 assay (FIG. 4), IRM (20 µg/ml) downregulated IL-12 p40 production, and the 3 donors downregulated IL-12 p40 production at 500 µg/ml. As shown in Table 10, fetal support tissue product/extract significantly inhibited IL-12 (p<0.05) production when loaded between 1 µg/ml to 1000 µg/ml HA. For example, undialyzed fetal support tissue composition in saline with or without dilution dose-dependently downregulated IL-12p40 from ≥50 µg/ml (all p<0.05) least (FIG. 6C).

Regarding the NO assay (FIG. 5), Internal Reference Material (20 µg/ml) inhibited NO production, and the 3 donors inhibited NO production at 500 µg/ml with Donor 2 and 3 induced cell death. As shown Table 10, fetal support tissue product/extract significantly inhibited NO (p<0.05) production when loaded between 1 µg/ml to 1000 µg/ml.

Cell Metabolic Activity WST-1 Assay: The Cell Metabolic Activity WST-1 Assay is a cell-based colorimetric assay used for quantification of cellular metabolic activity as an indicator of viability and proliferation of tumor cells. This assay is based on the reduction of a water-soluble tetrazolium (WST) salt WST-1 (4-[3-(4-Iodophenyl)-2-(4-nitrophenyl)-2H-5-tetrazolo]-1,3-benzene sulfonate) to a soluble formazan by metabolically active cells that are dependent on the glycolytic production of NAD(P)H in viable cells. Therefore, the amount of formazan dye formed directly correlates to the number of metabolically active cells and is quantified by measuring the absorbance at 450 nm using a multi-well spectrophotometer. The prostate cancer (PC) cell PC-3 is a human prostate cancer cell line, of which the metabolic activity was dose-dependently inhibited by HC-HA/PTX3 or HC-HA/PTX3-containing tissue extract, e.g., umbilical cord extract, but not by HA. Therefore, HC-HA/PTX3 or HC-HA/PTX3-containing tissue extracts can be assessed according to the killing, i.e., the inhibition of tumor cell metabolic activity (e.g., PC-3 cells) by WST-1 assay (FIG. 6A). HC-HA/PTX3-containing tissue extract inhibited cell metabolic activity p<0.05 compared to positive control when loaded between 50 μg/ml and 500 μg/ml HA.

Regarding the WST-1 assay (FIG. 6A), a dialyzed fetal support tissue composition in saline and fetal support tissue composition in water-for-injection with or without dilution dose-dependently inhibit cell metabolic activity from 100 to 500 μg/ml (all p<0.05 vs control) and undialyzed fetal support tissue composition in saline with or without dilution showed inhibition of metabolic activity from 50 μg/ml (all p<0.05) suggesting that diluted or undiluted dialyzed fetal support tissue in saline and fetal support tissue composition in water-for-injection dose-dependently kill tumor cells in WST-1 assay in a dose range from 100 to 500 HA μg/ml. As shown in Table 10, fetal support tissue at a concentration of 1 μg/ml to 1000 μg/ml HA significantly inhibited cell metabolic activity when compared to positive control (similar concentration).

Example 7. Assay Matrix: Safety Evaluation

Sterility: The safety of fetal support tissue compositions is performed for all injectables. Sterility is confirmed parametrically through minimum dose per $VD_{max}^{25}$ by ISO 11137 gamma radiation sterilization. Additionally, sterility is confirmed by acceptance criterion of "No Growth" per USP <71>.

Endotoxin: Acceptable criteria is established. It is based on maximum Endotoxin Units (EU) allowed for two injections of an adult and dilution per endotoxin method per USP <85>, with various assumptions following calculations for endotoxin limits in the sample for use in testing, such as the endotoxin limit, maximum dose to determine, for example, the HC-HA/PTX3 endotoxin limit dose.

Example 8. Assay Matrix: Quality Measurement

Water content: The maximum water content permissible in post-lyophilization tissue is established in order to prepare the fetal support tissue composition (e.g., HC-HA/PTX3) for effective micronization. Lyophilization process controls are designed to maintain water content below this limit. If water content is above this limit, the micronization process is inefficient at achieving the particle size distribution and the powder cannot be properly discharged from the micronization chamber. Thus, pooled sample water content acceptance criterion of NMT 15% is established and reflects the requirements of upstream processes.

Particle size distribution: Particle size analysis assesses the effectiveness of micronization and sieving. In addition, it detects any agglomeration of powder over time during in-process storage. The presence of large particles or agglomerate can impact the variability of drug product filling into vials. Also, large particles or agglomerates can plug the needle during injection. Particle size distribution is measured by image analysis in dry form which range from at least 10%, 50%, and 90% intercepts of the cumulative volume distribution of equivalent circular diameter. Volume distribution basis is more relevant for the detection of larger particles. In some embodiments, measurements for all samples may have particle size distribution ranging for example from about 0.05 μm to 1,000 μm.

Example 9. Assay Matrix: Reduction in Sample Variability and Improvement in Product Uniformity and Consistency The results of the present study demonstrated critical data. First, the data revealed that both the single donor samples and the pooled donor samples met the HA and protein criteria and that they exerted TRAP inhibition >80% at 300 μg HA. Secondly, the mean HA levels were comparable between the two groups (single and pooled; p>0.05) while the mean protein levels (BCA) were significantly higher in pooled samples than single donor samples (Table 9; p=0.009).

Importantly, both single donor and pooled donor samples preserve the HC-HA/PTX3 complex. The data further confirmed that the pooling process does not alter both HA molecular weight (MW) and HC-HA bond. Rather, it was confirmed that the pooling process used to generate a pooled sample produces more uniformity, meaning that there is less variability afforded by pooling samples. Pooling samples also improved the consistency of the fetal support tissue product due to the reduction in variability as measured by the reduction in coefficient of variation when samples were pooled in comparison to the coefficient of variation obtained among unpooled/single donor samples.

Data described herein demonstrate increasingly reduced variability following sample pooling. The data show a much higher opportunity of increased sample-to-sample variability or percentage coefficient of variation (% CV) and or standard deviation (SD) when single donor samples are utilized than when pooled samples are utilized. This difference in variability can be assessed by measuring CV (%), which is SD/mean (%). As summarized in Table 11, pooled samples ((n=3)) showed a lower CV (%) of HA (8.4% (pooled) vs. 27.4% (unpooled)), total protein (1.3% vs. 5.5%) and TRAP inhibition % (2.2% vs, 4.8%) than the individual, single donor sample lots ((n=4)). This notion is further exemplified by the finding that single donor lot (donor-2; FIG. 7) had a lower level of HA (>43% lower) and fainter PTX3 band (lanes 7 and 8; FIG. 8B) and another single donor lot (donor-1; FIG. 11) had a lower level of protein recovery (>9.7% lower) (Table 11, Table 9). These data confirm that such donor-to-donor sample variability is mitigated by the fetal support tissue sample pooling process. That the pooling process brings about improvement in the consistency of the fetal support tissue product, a reduction in variability while retaining product potency and high protein yield is a critical finding and a strong argument for pooling the fetal support tissue and/or fetal support tissue product.

Example 10: Use of Pooled Fetal Support Tissue Product to Treat a Simple Wound The pooled fetal support tissue product/extract (nHC-HA/PTX3) composition is applied to a patch. The patch is applied directly to the wound for a period of time sufficient to treat the wound.

Example 11: Use Pooled Fetal Support Tissue Product to Treat a Complex Wound An individual having a complex foot ulcer is identified. The pooled fetal support tissue product/extract/composition (nHC-HA/PTX3) is prepared for administration. The ulcer is debrided as necessary. Bone is resected as necessary. Optionally, an open cortex procedure is performed. The pooled extract disclosed (e.g., sheets, powder, grafts or cutting of strips of the pooled fetal support tissue product) is laid over the ulcer. A protective covering is place over the fetal support tissue product.

Example 12: Use Pooled Fetal Support Tissue Product to Repair a Gingival Wound An individual in need of repair of a gingival wound is identified. A pooled fetal support tissue extract/product is prepared for administration to the wound. The wound undergoes debridement where necessary. The fetal support tissue extract/product is placed over the wound. An appropriate wound covering is placed over the extract or product.

Example 13: Use Pooled Fetal Support Tissue Product to Repair a Damaged Joint Cavity An individual in need of repair of a damaged joint cavity is identified. A pooled fetal support tissue product/extract is prepared for administration. The joint cavity is prepared for administration of the product. The fetal support tissue product is placed over the joint cavity. A protective covering is place over the fetal support tissue product.

Example 14: Use Pooled Fetal Support Tissue Product to Treat a Herniated Disc The pooled nHC-HA/PTX3 (complex) composition is formulated as an injection. The formulation is injected at the site of the herniated disc. Treatment is continued until a therapeutic effect is observed.

Example 15: Use Pooled Fetal Support Tissue Product to Treat Osteoarthritis

The pooled nHC-HA/PTX3 (complex) composition is formulated as an injection. The formulation is injected into an arthritic joint by intra-articular injection. Treatment is continued until a therapeutic effect is observed.

What is claimed is:

1. A composition comprising a pooled umbilical cord and amniotic membrane (MAU) tissue, wherein the pooled MAU tissue comprises MAU tissue from a plurality of donors, wherein the pooled MAU tissue is lyophilized, wherein the lyophilized pooled MAU tissue comprises a native HC-HA/PTX3 (nHC-HA/PTX3) complex, wherein the nHC-HA/PTX3 complex possesses a therapeutic potency, and wherein the lyophilized pooled MAU tissue is enriched for total protein relative to non-pooled MAU tissue.

2. The composition of claim 1, wherein the composition comprises umbilical cord amniotic membrane, Wharton's jelly, or any combination thereof.

3. The composition of claim 1, wherein the composition is terminally sterilized, gamma irradiated, filtered, membrane filtered, electron beam sterilized or any combination thereof.

4. The composition of claim 1, wherein the pooled MAU tissue is cut, morselized, micronized, pulverized, ground, or any combination thereof.

5. The composition of claim 1, wherein the pooled MAU tissue is substantially free of metabolic activity.

6. The composition of claim 1, wherein the MAU tissue comprises an average particle size from about 0.01 micrometer (μm) to about 240 μm in diameter.

7. The composition of claim 1, wherein the MAU tissue comprises an average particle size of about 0.5 μm.

8. The composition of claim 1, wherein the composition is formulated as a gel, a powder, or a liquid.

9. The composition of claim 1, wherein the lyophilized pooled MAU tissue exhibits reduced variability of native HC-HA/PTX3 complex compared to non-pooled MAU tissue as determined by the ODI-TRAP assay; and wherein the pooled MAU tissue and the non-pooled MAU tissue are processed in the same manner and are obtained from the same type of tissue source.

10. The composition of claim 9, wherein the reduced variability of native HC-HA/PTX3 complex comprises a reduced variation as determined by a coefficient of variation.

11. The composition of claim 10, wherein the coefficient of variation is 3.0% or less.

12. The composition of claim 1, wherein the total protein is determined by a bicinchoninic acid (BCA) assay.

13. The composition of claim 1, wherein the composition inhibits TRAP activity by at least about 25% when compared to 50 μg/ml of RANKL.

14. The composition of claim 1, wherein the MAU tissue is cryopreserved or previously frozen.

15. A method of making the composition of claim 1, comprising obtaining MAU tissue from a plurality of donors and pooling the MAU tissue from the plurality of donors, thereby making pooled MAU tissue, wherein the pooled MAU tissue is lyophilized.

16. The method of claim 15, wherein the MAU tissue is not dehydrated.

17. The method of claim 15, wherein the MAU tissue is lyophilized before or after pooling the MAU tissue.

18. The method of claim 15, further comprising processing the MAU tissue by morselizing, pulverizing, micronizing, or a combination thereof.

19. A method of treating a condition in an individual, wherein the condition comprises an inflammatory disorder, a bladder condition, a bone disorder, a wound, an ocular disorder, a scar condition, a pain disorder, a nerve disorder, spina bifida, or any combination thereof in an individual in need thereof, the method comprising administering the composition of claim 1 to the individual, thereby treating the condition.

20. The method of claim 19, wherein the inflammatory disorder comprises dry eye.

21. The method of claim 19, where in the pain disorder comprises pain in a shoulder.

22. The method of claim 19, wherein the bone disorder comprises osteoarthritis.

23. The method of claim 19, wherein the bone disorder comprises osteoporosis.

24. The method of claim 19, wherein the ocular disorder comprises dry eye, ocular surface inflammation or ulcerative keratitis.

25. The method of claim 19, wherein the wound comprises a complex wound.

26. A method of determining the potency of the lyophilized, pooled MAU tissue composition of claim 1, wherein the method comprises:

performing a potency cell-based assay on the composition of claim 1, wherein the potency cell-based assay comprises:

(i) an osteoclast differentiation inhibition tartrate-resistant acid phosphatase (ODI-TRAP) assay;

(ii) a Nitric Oxide (NO assay); or (iii) a macrophage polarization (M2) assay; and wherein the lyophilized, pooled MAU tissue composition exhibits a statistically significant inhibition of bioactivity in the potency cell-based assays (i), (ii) or (iii) compared to a positive control assay.

* * * * *